US012723100B2

(12) United States Patent
Pei et al.

(10) Patent No.: US 12,723,100 B2
(45) Date of Patent: Sep. 1, 2026

(54) NECTIN-4 ANTIBODIES AND USES THEREOF

(71) Applicant: CSPC MEGALITH BIOPHARMACEUTICAL CO., LTD., Shijiazhuang (CN)

(72) Inventors: Yi Pei, Paoli, PA (US); Haichun Huang, Fremont, CA (US); Ming Lei, Princeton, NJ (US); Han Li, Newton, PA (US)

(73) Assignee: CSPC MEGALITH BIOPHARMACEUTICAL CO., LTD., Shijiazhuang (CN)

( * ) Notice: Subject to any disclaimer, the term of this patent is extended or adjusted under 35 U.S.C. 154(b) by 700 days.

(21) Appl. No.: 18/024,465

(22) PCT Filed: Sep. 3, 2021

(86) PCT No.: PCT/US2021/049014

§ 371 (c)(1),
(2) Date: Mar. 2, 2023

(87) PCT Pub. No.: WO2022/051591

PCT Pub. Date: Mar. 10, 2022

(65) Prior Publication Data

US 2023/0331867 A1 Oct. 19, 2023

Related U.S. Application Data

(60) Provisional application No. 63/166,622, filed on Mar. 26, 2021, provisional application No. 63/074,864, filed on Sep. 4, 2020.

(51) Int. Cl.
*C07K 16/30* (2006.01)
*A61P 35/00* (2006.01)

(52) U.S. Cl.
CPC .......... *C07K 16/3076* (2013.01); *A61P 35/00* (2018.01); *C07K 2317/24* (2013.01); *C07K 2317/565* (2013.01)

(58) Field of Classification Search
None
See application file for complete search history.

(56) References Cited

U.S. PATENT DOCUMENTS

| | | | | |
|---|---|---|---|---|
| 10,675,357 | B2 * | 6/2020 | Lopez ................ | A61K 47/6899 |
| 2018/0194862 | A1 | 7/2018 | Akamatsu et al. | |

FOREIGN PATENT DOCUMENTS

| | | | |
|---|---|---|---|
| WO | 2017042210 | A1 | 3/2017 |
| WO | 2018158398 | A1 | 9/2018 |
| WO | 2018226578 | A1 | 12/2018 |
| WO | 2019215728 | A1 | 11/2019 |

* cited by examiner

*Primary Examiner* — Nelson B Moseley, II
*Assistant Examiner* — James Ryland Melchior
(74) *Attorney, Agent, or Firm* — Morgan, Lewis & Bockius LLP

(57) ABSTRACT

The present disclosure provides antibodies and antibody fragments thereof that bind to Nectin-4. Such antibodies and antibody fragments are useful for the treatment of cancer, either alone or in combination with other agents.

20 Claims, 9 Drawing Sheets

Figure 2:
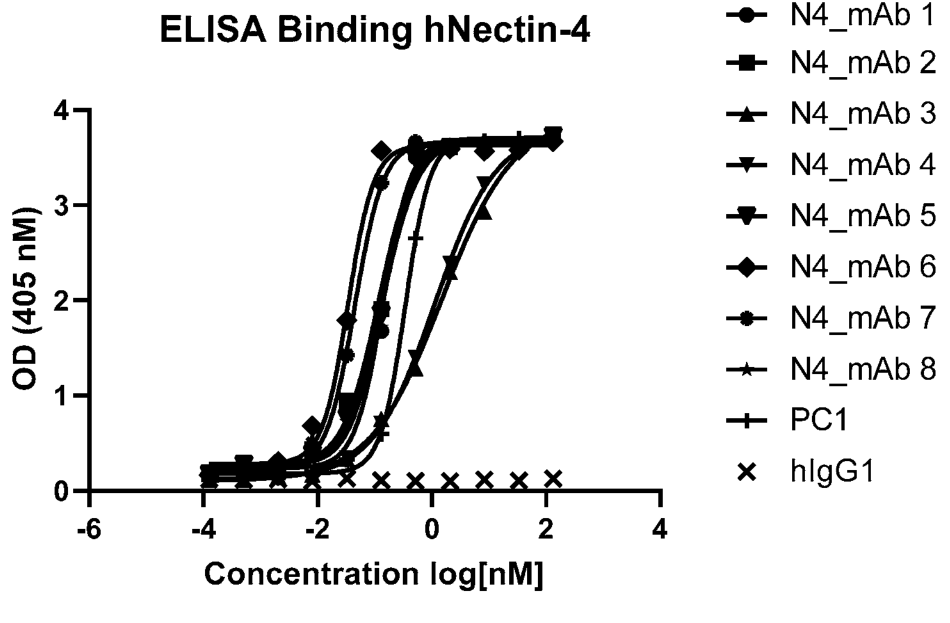

Specification includes a Sequence Listing.

FIG. 1

SEQ ID NO: 1> N4_mAb 1_VH
QVQLKQSGPGLVQPSQSLSITCTVSGFSLTNYGVNWVRQPPGKGLEWLGVIWSGGSTDYNAAFISRLSISKDISKSQVFFKMNSLQADDTAKYYCAREGYDGYAMDYWGQGTSVTVSS

| NYGVN | VIWSGGSTDYNAAFIS | EGYDGYAMDY |
|---|---|---|
| SEQ: 17 | SEQ: 18 | SEQ: 19 |

SEQ ID NO: 2> N4_mAb 1_VL
DIQMTQSPASLSVSVGETVTITCRASENIFSSLAWYQQKQGKSPQLLVYGATNLADGVPSRFSGSGSGTQYSLKINSLQSEDFGTYWCQHFWGNPWTFGGGTKLEIK

| RASENIFSSLA | GATNLAD | QHFWGNPWT |
|---|---|---|
| SEQ: 20 | SEQ: 21 | SEQ: 22 |

SEQ ID NO: 3> N4_mAb 2_VH
QVQLKQSGPNLVQPSQSLSITCTVSGFSLTTYGAHWVRQSPGKGLEWLGVIWRGGSTDYNAAFMSRLSITKDNSKSQVFFKMNSLQADDTAIYYCAKIGYDGYAMDNWGQGTSVTVSS

| TYGAH | VIWRGGSTDYNAAFMS | IGYDGYAMDN |
|---|---|---|
| SEQ: 23 | SEQ: 24 | SEQ: 25 |

SEQ ID NO: 4> N4_ mAb 2_VH
DFQVTQSPASLSASVGETVTITCRTSENIHNYLAWYQQKQGKSPQLLVYNAKTLADGVPSRFSGSGSGTQYSLKINSLQPEDFGTYYCQHFWSSPWTFGGGTKLEIK

| RTSENIHNYLA | NAKTLAD | QHFWSSPWT |
|---|---|---|
| SEQ: 26 | SEQ: 27 | SEQ: 28 |

SEQ ID NO: 5> N4_mAb 3_VH
EVQLQQSGAELVKPGASVKLSCTVSGFNIKDTYMHWVKQRPEQGLEWIGRIDPANGNTKYDPKFQGKATIIADKASNTAYLQLSSLTSEDAAVYYCAHYYGSSYFAMDCWGQGTSVTVSS

| DTYMH | RIDPANGNTKYDPKFQG | YYGSSYFAMDC |
|---|---|---|
| SEQ: 29 | SEQ: 30 | SEQ: 31 |

SEQ ID NO: 6> N4_mAb 3_VL
DIVMTQSHKFMSTSVGDRVSITCKASQDVSTAVAWYQQKPGQSPKLLIYWASTRHTGVPDRFTGSGSGTDYTLTISSVQTEDLALYYCQQHYSTPLTFGAGTKLELK

| KASQDVSTAVA | WASTRHT | QQHYSTPLT |
|---|---|---|
| SEQ: 32 | SEQ: 33 | SEQ: 34 |

SEQ ID NO: 7> N4_mAb 4_VH
DVQLQESGPDLVKPSQSLSLTCTVTGYSITSAYNWHWIRQFPGNKLEWMGYIHYSGRTNYNPSLKSRISITRDTSKNQFFLQLNSLTTEDTATYYCARWITTATGWYLDVWGAGTTVTVSS

| SAYNWH | YIHYSGRTNYNPSLKS | WITTATGWYLDV |
|---|---|---|
| SEQ: 35 | SEQ: 36 | SEQ: 37 |

FIG. 1 (continued)

SEQ ID NO: 8> N4_mAb 4_VL
DIVLTQSPASLAVSLGQRATISCRASESVANYGISFMNWFQQKPGQPPKLLIYAASNQGSGVP
ARFSGSGSGTDFSLNIHPMEEDDTAMYFCQQSKEVPWTFGGGTKLEIK

| RASESVANYGISFMN | AASNQGS | QQSKEVPWT |
|---|---|---|
| SEQ: 38 | SEQ: 39 | SEQ: 40 |

SEQ ID NO: 9> N4_mAb 5_VH
EVQLQQSGPDLVKPGASVKISCKASGYSFTGHYMHWVKQSHGKSLEWIGRVNPNNGGSSYN
QKFKDKAILTVDKSSTTAYMELRSLTSEDSAVYYCARDPLGGSYGFAYWGQGTLVTVSA

| GHYMH | RVNPNNGGSSYNQKFKD | DPLGGSYGFAY |
|---|---|---|
| SEQ: 41 | SEQ: 42 | SEQ: 43 |

SEQ ID NO: 10> N4_mAb 5_VL
DIVLTQSPASLAVSLGQRATISCRASQSVTTSSYSYMHWYQQKPGQPPKLLIKYASNLESGVP
ARFSGSGSGTDFTLNIHPVEEEDTATYYCQHSWEIPYTFGGGTKLEMK

| RASQSVTTSSYSYMH | YASNLES | QHSWEIPYT |
|---|---|---|
| SEQ: 44 | SEQ: 45 | SEQ: 46 |

SEQ ID NO: 11> N4_mAb 6_VH
QVQLQQSGPELVKPGASVRISCKASGYTFTTYYIHWVKQRPGQGLEWIGWIYPGNVNTKYTE
NFKDKATLTADKSSSTAYMQLSSLTSEDSAVYFCARGLYYFDFWGQGTTLTVSS

| TYYIH | WIYPGNVNTKYTENFKD | GLYYFDF |
|---|---|---|
| SEQ: 47 | SEQ: 48 | SEQ: 49 |

SEQ ID NO: 12> N4_mAb 6_VL
SIVMTQTPKFLLVSAGDRVTITCKASQSVNNDVAWYQQKPGQSPKLLIYYASNRDTGVPDRF
TGSGFGTDFTFTISSVQAEDLAVYFCQQDYSSPYTFGGGTKLEIK

| KASQSVNNDVA | YASNRDT | QQDYSSPYT |
|---|---|---|
| SEQ: 50 | SEQ: 51 | SEQ: 52 |

SEQ ID NO: 13> N4_mAb 7_VH
QVQLQQSGPELVKPGASVKMSCKASGYTFTTYYIHWVKQRPGQGLEWIGWIYPGNAGIKSN
EKFKGKTTLTADKSSSTAYMLLSSLTSEDSAIYFCARGVYFFDYWGQGTTLTVSS

| TYYIH | WIYPGNAGIKSNEKFKG | GVYFFDY |
|---|---|---|
| SEQ: 47 | SEQ: 53 | SEQ: 54 |

SEQ ID NO: 14> N4_mAb 7_VL
SIVMTQTPKFLLVSAGDRVTITCKASQSVNNDVSWFQQKPGQSPKLLIYYASNRYTGVPDRFS
GSGYGTDFTFTITTVQAEDLAVYFCQQDYSSPYTFGGGTKLEIK

| KASQSVNNDVS | YASNRYT | QQDYSSPYT |
|---|---|---|
| SEQ: 55 | SEQ: 56 | SEQ: 52 |

SEQ ID NO: 15> N4_mAb 8_VH

FIG. 1 (continued)

QVQLQQSGPVLVKPGASVRISCKASGYTFTSYYIHWVKQRPGQGLEWIGWIYPGNVNTKYNENFRDKATLTADKSSSTSYMQLSSLTSEDSAVYFCARGIYYFDYWGQGTTLTVSS

| SYYIH | WIYPGNVNTKYNENFRD | GIYYFDY |
|---|---|---|
| SEQ: 57 | SEQ: 58 | SEQ: 59 |

SEQ ID NO: 16> N4_mAb 8_VL
IIVMTQTPKFLLVSAGDRVTITCKASQSVNNDVAWYQEKPGQSPKLLIYYASNRDTGVPDRFTGSGYGTDFTFTISTVQAEDLAVYFCHQDYSSPFTFGSGTKLEIK

| KASQSVNNDVA | YASNRDT | HQDYSSPFT |
|---|---|---|
| SEQ: 50 | SEQ: 51 | SEQ: 60 |

SEQ ID NO: 61>NP_112178.2 nectin-4 precursor [Homo sapiens]

MPLSLGAEMWGPEAWLLLLLLLASFTGRCPAGELETSDVVTVVLGQDAKLPCFYRGDSGEQVGQVAWARVDAGEGAQELALLHSKYGLHVSPAYEGRVEQPPPPRNPLDGSVLLRNAVQADEGEYECRVSTFPAGSFQARLRLRVLVPPLPSLNPGPALEEGQGLTLAASCTAEGSPAPSVTWDTEVKGTTSSRSFKHSRSAAVTSEFHLVPSRSMNGQPLTCVVSHPGLLQDQRITHILHVSFLAEASVRGLEDQNLWHIGREGAMLKCLSEGQPPPSYNWTRLDGPLPSGVRVDGDTLGFPPLTTEHSGIYVCHVSNEFSSRDSQVTVDVLDPQEDSGKQVDLVSASVVVVGVIAALLFCLLVVVVVLMSRYHRRKAQQMTQKYEEELTLTRENSIRRLHSHHTDPRSQPEESVGLRAEGHPDSLKDNSSCSVMSEEPEGRSYSTLTTVREIETQTELLSPGSGRAEEEEDQDEGIKQAMNHFVQENGTLRAKPTGNGIYINGRGHLV

SEQ ID NO: 62>XP_005541277.1 PREDICTED: nectin-4 isoform X1 [Macaca fascicularis]

MPLSLGAEMWGPEAWLLLLLLLASFTGRCPAGELETSDVVTVVLGQDAKLPCFYRGDSGEQVGQVAWARADAGEGAQELALLHSKYGLHVSPAYEGRVEQPPPPRNPLDGSVLLRNAVQADEGEYECRVSTFPAGSFQARLRLRVLVPPLPSLNPGPALEEGQGLTLAASCTAEGSPAPSVTWDTEVKGTTSSRSFKHSRSAAVTSEFHLVPSRSMNGQPLTCVVSHPGLLQDQRITHILHVSFLAEASVRGLEDQNLWHVGREGAMLKCLSEGQPPPSYNWTRLDGPLPSGVRVDGDTLGFPPLTTEHSGIYVCHVSNEFSSRDSQVTVDVLDPQEDSGKQVDLVSASVVVVGVIAALLFCLLVVVVVLMSRYHRRKAQQMTQKYEEELTLTRENSIRRLHSHHTDPRSQPEESVGLRAEGHPDSLKDNSSCSVMSEEPEGRSYSTLTTVREIETQTELLSPGSGRTEEEEDQDEGIKQAMNHFVQENGTLRAKPTGNGIYINGRGHLV

SEQ ID NO: 63>NP_001102546.1 nectin-4 precursor [Rattus norvegicus]

MPLSLGAEMWGPEAWLLLLFLASFTGRYSAGELETSDLVTVVLGQDAKLPCFYRGDPDEQVGQVAWARVDPNEGTRELALLHSKYGLHVSPAYEDRVEQPPPPRDPLDGSILLRNAVQADEGEYECRVSTFPAGSFQARMRLRVLVPPLPSLNPGPPLEEGQGLTLAASCTAEGSPAPSVTWDTEVKGTQSSRSFKHSRSAAVTSEFHLVPSRSMNGQPLTCVVSHPGLLQDQRITHTLQVAFLAEASVRGLEDQNLWHVGREGATLKCLSEGQPPPKYNWTRLDGPLPSGVRVKGDTLGFPPLTTEHSGVYVCHVSNELSSRASQVTVEVLDPEDPGKQVDLVSASVVVVGVIAALLFCLLVVVVVLMSRYHRRKAQQMTQKYEEELTLTRENSIRRLHSHHTDPRSQPEESVGLRAEGHPDSLKDNSSCS

FIG. 1 (continued)

VMSEEPEGRSYSTLTTVREIETQTELLSPGSGRTEEEDDQDEGIKQAMNHFVQENGTLRAKPT
GNGIYINGRGHLV

SEQ ID NO: 64>NP_082169.2 nectin-4 isoform a precursor [Mus musculus]

MPLSLGAEMWGPEAWLRLLFLASFTGQYSAGELETSDVVTVVLGQDAKLPCFYRGDPDEQV
GQVAWARVDPNEGIRELALLHSKYGLHVNPAYEDRVEQPPPPRDPLDGSVLLRNAVQADEG
EYECRVSTFPAGSFQARMRLRVLVPPLPSLNPGPPLEEGQGLTLAASCTAEGSPAPSVTWDTE
VKGTQSSRSFTHPRSAAVTSEFHLVPSRSMNGQPLTCVVSHPGLLQDRRITHTLQVAFLAEAS
VRGLEDQNLWQVGREGATLKCLSEGQPPPKYNWTRLDGPLPSGVRVKGDTLGFPPLTTEHS
GVYVCHVSNELSSRDSQVTVEVLDPEDPGKQVDLVSASVIIVGVIAALLFCLLVVVVVLMSR
YHRRKAQQMTQKYEEELTLTRENSIRRLHSHHSDPRSQPEESVGLRAEGHPDSLKDNSSCSV
MSEEPEGRSYSTLTTVREIETQTELLSPGSGRTEEDDDQDEGIKQAMNHFVQENGTLRAKPTG
NGIYINGRGHLV

SEQ ID NO: 65>NP_002846.3 nectin-1 isoform 1 precursor [Homo sapiens]

MARMGLAGAAGRWWGLALGLTAFFLPGVHSQVVQVNDSMYGFIGTDVVLHCSFANPLPSV
KITQVTWQKSTNGSKQNVAIYNPSMGVSVLAPYRERVEFLRPSFTDGTIRLSRLELEDEGVYI
CEFATFPTGNRESQLNLTVMAKPTNWIEGTQAVLRAKKGQDDKVLVATCTSANGKPPSVVS
WETRLKGEAEYQEIRNPNGTVTVISRYRLVPSREAHQQSLACIVNYHMDRFKESLTLNVQYE
PEVTIEGFDGNWYLQRMDVKLTCKADANPPATEYHWTTLNGSLPKGVEAQNRTLFFKGPIN
YSLAGTYICEATNPIGTRSGQVEVNITEFPYTPSPPEHGRRAGPVPTAIIGGVAGSILLVLIVVG
GIVVALRRRRHTFKGDYSTKKHVYGNGYSKAGIPQHHPPMAQNLQYPDDSDDEKKAGPLG
GSSYEEEEEEEEGGGGGERKVGGPHPKYDEDAKRPYFTVDEAEARQDGYGDRTLGYQYDPE
QLDLAENMVSQNDGSFISKKEWYV

NECTIN-4 ANTIBODIES AND USES THEREOF

CROSS-REFERENCE TO RELATED APPLICATIONS

The present application is a national stage application of International Patent Application No. PCT/US2021/049014, filed Sep. 3, 2021, which claims the benefit of and priority to U.S. Provisional Patent Application No. 63/074,864, filed on Sep. 4, 2020, and U.S. Provisional Patent Application No. 63/166,622, filed on Mar. 26, 2021, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 2, 2023, is named 122863-5003-US_Sequence_Listing.txt" and is 49 kilobytes in size.

FIELD

The present disclosure relates to antibodies and fragments thereof which bind to Nectin-4. The disclosure further relates to therapeutic and diagnostic compositions comprising these antibodies and to methods of using the compositions for the treatment and/or diagnosis of cancer.

BACKGROUND

The human Nectin family comprises 9 homologues (Nectin-1 to Nectin-4 and Nectin-like-1 to -5) (Duraivelan et al., *Sci Rep,* 10:9434, 2020). Nectin proteins (Nectin-1, Nectin-2, Nectin-3, and Nectin-4), are calcium-independent immunoglobulin super family (IgSF) cell adhesion molecules that homophilically or heterophilically trans-interact to mediate cell-cell adhesion at adherens junctions in epithelial cells. In normal epithelium, adherens junctions define cell polarity, a characteristic that is often lost during tumorigenesis.

Nectin-1, -2, -3, and -4 are expressed as single-pass type I glycoproteins, and are characterized by a common domain organization, consisting of an extracellular domain (ECD) with three tandem immunoglobulin-like domains/loops arranged as an N-terminal Ig-like variable domain (D1) followed by two Ig-like constant domains (D2 and D3). Nectins interact with each other via V-domain to V-domain binding interactions thereby creating a trans-hetero-interaction network supporting cell-cell adhesion. Heterophilic interactions among Nectin-3/Nectin-1, Nectin-3/Nectin-2, Nectin-1/Nectin-4 have been reported (Harrison et al., *Nat Struct Mol Biol,* 19(9):906-915, 2012). In addition to their role in cell-cell adhesion the Nectins play important roles in regulating a diverse range of physiologic cellular activities, in viral entry and in immune modulation.

Nectins (from the Latin word "necto" meaning "to connect") interact with Nectins on other cell surface molecules through their Ig-like V-domain of their ECD. Nectins first bind to form cis-dimers on the same cell, and then function to promote cell-cell adhesion by forming homophilic or heterophilic trans-dimers with Nectins or other members of the immunoglobulin super family (IgSF) on an adjacent cell (Miyoshi et al., *Am J Nephrol,* 27:590, 2007). Heterophilic trans-dimers have been reported to form stronger cell-cell interactions than homophilic trans-dimers. The specificity of binding is different for each Nectin (e.g., Nectin-4 binds to itself and to Nectin-1).

The ability of Nectin family members to interact with additional cell surface molecules significantly expands their interaction network. Several members of the Nectin family can exert immunoregulatory functions as a consequence of their heterophilic trans-interaction with another member of the IgSF. These interactions are known to impact the functions of diverse immune cell types including natural killer (NK) cells, monocytes, dendritic cells (DCs), and T lymphocytes. Not only are several of the known Nectin family partners IgSF members, some Nectins are known to recognize common binding partners. For example, Nectin-2 and PVR both recognize CD226, TIGIT and Nectin-3 (Duraivelan et al., *Sci Rep,* 10:9434, 2020).

Nectin-4 has been reported to be upregulated in various epithelial cell cancers, such as breast cancer (Fabre-Lafay et al., *BMC Cancer,* 7:73, 2007), lung cancer (Takano et al., *Cancer Res,* 69(16):6694-03, 2009, ovarian cancer (Derycke et al., *Am J Clin Pathol,* 5:835-845, 2010, pancreatic cancer (Nishiwada et al., *J Exp Clin Cancer Res,* 34(1):30, 2015, gallbladder cancer (Zhang et al., *Cancer Lett,* 375:179-189, 2016), and gastric cancer (Zhang et al., *Hum Pathol,* 72:107-116, 2018). These cancers frequently have copy number gains or focal amplifications of the Nectin-4 locus (Pavlova et al., *Elife,* 2:e00358, 2013).

Recently, evidence has accumulated, showing that Nectins contribute to tumorigenesis and functions to promote metastasis. In particular, Nectin-4 has been implicated in cancer cell adhesion, migration, proliferation and epithelial-mesenchymal transition. In breast cancer, pancreatic cancer and lung cancer, overexpression of Nectin-4, or detection or soluble Nectin-4 in patient serum has been reported to be associated with tumor progression and and/or poor survival (Fabre-Lafay et al., *BMC Cancer,* 7:73, 2007, Takano et al., *Cancer Res,* 69(16):6694-03, 2009, Derycke et al., *Am J Clin Pathol,* 5:835-845, 2010, Nishiwada et al., *J Exp Clin Cancer Res,* 34(1):30, 2015, and Lattanzio et al., *Oncogenesis,* 3:e118, 2014).

There is an unmet need to provide effective, safe and specific anti-Nectin-4 antibodies that alone, or in combination with other agents can be used for antibody-based immunotherapy.

SUMMARY

The present disclosure addresses the above need by providing anti-Nectin-4 antibodies and fragments thereof that bind to Nectin-4 including, for example, Nectin-4 present on the surface of cancer cells. These antibodies and fragments thereof are characterized by unique sets of CDR sequences, specificity for Nectin-4 and are useful in cancer immunotherapy as a monotherapy or as a combination therapy with other anti-cancer agents. More specifically, the disclosure relates to antibodies that bind to human Nectin-4, and to their use to modulate (e.g., antagonize) a Nectin-4-mediated activity of cells localized to the tumor microenvironment.

According to some embodiments, the anti-Nectin-4 antibodies or antibody fragments thereof comprises a set of six complementarity determining region (CDR) sequences selected from the group consisting of three CDRs of a heavy chain (HC) variable region selected from SEQ ID NOs: 1, 3, 5, 7, 9, 11, 13 and 15 and three CDRs of a light chain (LC) variable region selected from SEQ ID NOs: 2, 4, 6, 8, 10, 12, 14 and 16, or an analog or derivative thereof having at least 90%, 95%, or 99% sequence identity to a CDR in any one of SEQ ID NOs: 1-16 provided that the antibody or fragment thereof retains binding to Nectin-4.

In some embodiments, the anti-Nectin-4 antibodies or antibody fragments thereof comprise a heavy chain variable region comprising CDR1: SEQ ID NO: 17, CDR2: SEQ ID NO: 18, and CDR3: SEQ ID NO: 19; and/or a light chain variable region comprising CDR1: SEQ ID NO: 20, CDR2: SEQ ID NO: 21, and CDR3: SEQ ID NO: 22.

In some embodiments, the anti-Nectin-4 antibodies or antibody fragments thereof comprise a heavy chain variable region comprising CDR1: SEQ ID NO: 23, CDR2: SEQ ID NO: 24, and CDR3: SEQ ID NO: 25: and/or a light chain variable region comprising CDR1: SEQ ID NO: 26, CDR2: SEQ ID NO: 27, and CDR3: SEQ ID NO: 28.

In some embodiments, the anti-Nectin-4 antibodies or antibody fragments thereof comprise a heavy chain variable region comprising CDR1: SEQ ID NO: 29, CDR2: SEQ ID NO: 30, and CDR3: SEQ ID NO: 31; and/or a light chain variable region comprising CDR1: SEQ ID NO: 32, CDR2: SEQ ID NO: 33, and CDR3: SEQ ID NO: 34.

In some embodiments, the anti-Nectin-4 antibodies or antibody fragments thereof comprise a heavy chain variable region comprising CDR1: SEQ ID NO: 35, CDR2: SEQ ID NO: 36, and CDR3: SEQ ID NO: 37: and/or a light chain variable region comprising CDR1: SEQ ID NO: 38, CDR2: SEQ ID NO: 39, and CDR3: SEQ ID NO: 40.

In some embodiments, the anti-Nectin-4 antibodies or antibody fragments thereof comprise a heavy chain variable region comprising CDR1: SEQ ID NO: 41, CDR2: SEQ ID NO: 42, and CDR3: SEQ ID NO: 43: and/or a light chain variable region comprising CDR1: SEQ ID NO: 44, CDR2: SEQ ID NO: 45, and CDR3: SEQ ID NO: 46.

In some embodiments, the anti-Nectin-4 antibodies or antibody fragments thereof comprise a heavy chain variable region comprising CDR1: SEQ ID NO: 47, CDR2: SEQ ID NO: 48, and CDR3: SEQ ID NO: 49; and/or a light chain variable region comprising CDR1: SEQ ID NO: 50, CDR2: SEQ ID NO: 51, and CDR3: SEQ ID NO: 52.

In some embodiments, the anti-Nectin-4 antibodies or antibody fragments thereof comprise a heavy chain variable region comprising CDR1: SEQ ID NO: 47, CDR2: SEQ ID NO: 53, and CDR3: SEQ ID NO: 54; and/or a light chain variable region comprising CDR1: SEQ ID NO: 55, CDR2: SEQ ID NO: 56, and CDR3: SEQ ID NO: 52.

In some embodiments, the anti-Nectin-4 antibodies or antibody fragments thereof comprise a heavy chain variable region comprising CDR1: SEQ ID NO: 57, CDR2: SEQ ID NO: 58, and CDR3: SEQ ID NO: 59; and/or a light chain variable region comprising CDR1: SEQ ID NO: 50, CDR2: SEQ ID NO: 51, and CDR3: SEQ ID NO: 60.

In some embodiments, the anti-Nectin-4 antibodies or antibody fragments thereof comprise a variable heavy chain sequence selected from the group consisting of SEQ ID NOs: 1, 3, 5, 7, 9, 11, 13 and 15, or an analog or derivative thereof having at least 90%, 95%, or 99% sequence identity to SEQ ID NOs: 1, 3, 5, 7, 9, 11, 13 or 15 provided that the antibody or fragment thereof retains binding to Nectin-4

In other embodiments, the anti-Nectin-4 antibodies or antibody fragments thereof comprise a variable light chain sequence selected from the group consisting of SEQ ID NOs: 2, 4, 6, 8, 10, 12, 14 and 16, or an analog or derivative thereof having at least 90%, 95%, or 99% sequence identity to SEQ ID NOs: 2, 4, 6, 8, 10, 12, 14 or 16 provided that the antibody or fragment thereof retains binding to Nectin-4.

In other embodiments, the anti-Nectin-4 antibodies or antibody fragments thereof comprise a variable heavy chain sequence selected from the group consisting of SEQ ID NOs: 1, 3, 5, 7, 9, 11, 13 and 15 and a variable light chain sequence selected from the group consisting of SEQ ID NOs: 2, 4, 6, 8, 10, 12, 14 and 16.

In some embodiments, the anti-Nectin-4 antibodies or antibody fragments thereof comprise a variable heavy chain sequence and a variable light chain sequence, selected from the following combinations:

(a) a variable heavy chain sequence comprising SEQ ID NO: 1 and a variable light chain sequence comprising SEQ ID NO: 2;

(b) a variable heavy chain sequence comprising SEQ ID NO: 3 and a variable light chain sequence comprising SEQ ID NO: 4;

(c) a variable heavy chain sequence comprising SEQ ID NO: 5 and a variable light chain sequence comprising SEQ ID NO: 6;

(d) a variable heavy chain sequence comprising SEQ ID NO: 7 and a variable light chain sequence comprising SEQ ID NO: 8;

(e) a variable heavy chain sequence comprising SEQ ID NO: 9 and a variable light chain sequence comprising SEQ ID NO: 10;

(f) a variable heavy chain sequence comprising SEQ ID NO: 11 and a variable light chain sequence comprising SEQ ID NO: 12;

(g) a variable heavy chain sequence comprising SEQ ID NO: 13 and a variable light chain sequence comprising SEQ ID NO: 14; and (h) a variable heavy chain sequence comprising SEQ ID NO: 15 and a variable light chain sequence comprising SEQ ID NO: 16.

In some embodiments, an immunoconjugate comprising an antibody or fragment thereof that binds Nectin-4 covalently attached to a cytotoxic agent is provided, wherein the antibody or fragment thereof comprises a variable heavy chain sequence and a variable light chain sequence, selected from the following combinations:

(a) a variable heavy chain sequence comprising SEQ ID NO: 1 and a variable light chain sequence comprising SEQ ID NO: 2;

(b) a variable heavy chain sequence comprising SEQ ID NO: 3 and a variable light chain sequence comprising SEQ ID NO: 4;

(c) a variable heavy chain sequence comprising SEQ ID NO: 5 and a variable light chain sequence comprising SEQ ID NO: 6;

(d) a variable heavy chain sequence comprising SEQ ID NO: 7 and a variable light chain sequence comprising SEQ ID NO: 8;

(e) a variable heavy chain sequence comprising SEQ ID NO: 9 and a variable light chain sequence comprising SEQ ID NO: 10;

(f) a variable heavy chain sequence comprising SEQ ID NO: 11 and a variable light chain sequence comprising SEQ ID NO: 12;

(g) a variable heavy chain sequence comprising SEQ ID NO: 13 and a variable light chain sequence comprising SEQ ID NO: 14; and (h) a variable heavy chain sequence comprising SEQ ID NO: 15 and a variable light chain sequence comprising SEQ ID NO: 16.

In some embodiments, an immunoconjugate comprising an antibody or fragment thereof that binds Nectin-4 covalently attached to a cytotoxic agent is provided, wherein the antibody comprises (a) a heavy chain variable region comprising CDR1: SEQ ID NO: 17, CDR2: SEQ ID NO: 18, and CDR3: SEQ ID NO: 19; and/or a light chain variable region comprising CDR1: SEQ ID NO: 20, CDR2: SEQ ID NO: 21, and CDR3: SEQ ID NO: 22; (b) a heavy chain variable region comprising CDR1: SEQ ID NO: 23, CDR2: SEQ ID NO: 24, and CDR3: SEQ ID NO: 25; and/or a light chain variable region comprising CDR1: SEQ ID NO: 26, CDR2: SEQ ID NO: 27, and CDR3: SEQ ID NO: 28; (c) a heavy chain variable region comprising CDR1: SEQ ID NO: 29, CDR2: SEQ ID NO: 30, and CDR3: SEQ ID NO: 31; and/or a light chain variable region comprising CDR1: SEQ ID NO: 32, CDR2: SEQ ID NO: 33, and CDR3: SEQ ID NO: 34; (d) CDR1: SEQ ID NO: 35, CDR2: SEQ ID NO: 36, and CDR3: SEQ ID NO: 37; and/or a light chain variable region comprising CDR1: SEQ ID NO: 38, CDR2: SEQ ID NO: 39, and CDR3: SEQ ID NO: 40; and/or (e) a heavy chain variable region comprising CDR1: SEQ ID NO: 41, CDR2: SEQ ID NO: 42, and CDR3: SEQ ID NO: 43; and/or a light chain variable region comprising CDR1: SEQ ID NO: 44, CDR2: SEQ ID NO: 45, and CDR3: SEQ ID NO: 46; and/or (f) a heavy chain variable region comprising CDR1: SEQ ID NO: 47, CDR2: SEQ ID NO: 48, and CDR3: SEQ ID NO: 49; and/or a light chain variable region comprising CDR1: SEQ ID NO: 50, CDR2: SEQ ID NO: 51, and CDR3: SEQ ID NO: 52; and/or (g) a heavy chain variable region comprising CDR1: SEQ ID NO: 47, CDR2: SEQ ID NO: 53, and CDR3: SEQ ID NO: 54; and/or a light chain variable region comprising CDR1: SEQ ID NO: 55, CDR2: SEQ ID NO: 56, and CDR3: SEQ ID NO: 52 or (h) a heavy chain variable region comprising CDR1: SEQ ID NO: 57, CDR2: SEQ ID NO: 58, and CDR3: SEQ ID NO: 59; and/or a light chain variable region comprising CDR1: SEQ ID NO: 50, CDR2: SEQ ID NO: 51, and CDR3: SEQ ID NO: 60.

In some embodiments, the anti-Nectin-4 antibodies and antibody fragments thereof comprise one or more heavy chain variable region CDRs disclosed in Table 1 and/or one or more light chain variable region CDRs disclosed in Table 2.

In some embodiments, the anti-Nectin-4 antibodies or antibody fragments thereof exhibit one or more of the following structural and functional characteristics, alone or in combination: (a) is specific for human Nectin-4 (b) does not bind to human Nectin-1, human Nectin-2 or human Nectin-3, (c) binds to an epitope in the N-terminal Ig-like V domain of Nectin-4, (d) is internalized from the surface of Nectin-4 positive cells after binding Nectin-4 (e) cross-reacts with cynomolgus Nectin-4; (f) cross-reacts with rat and/or murine Nectin-4, (g) disrupts the human Nectin-4/Nectin-1 binding interaction, (h) disrupts the human Nectin-4/TIGIT binding interaction, (i) reduces the level of cell surface protein expression of Nectin-4 on human tumor cells, or (j) directs ADCC of human cells expressing endogenous levels of Nectin-4.

In some embodiments, the anti-Nectin-4 antibodies or fragments thereof specifically bind to human cells expressing endogenous levels of Nectin-4 and/or to host cells engineered to overexpress Nectin-4, and do not demonstrate binding (e.g., specific binding) to the extracellular domain of human Nectin-1, Nectin-2 or Nectin-3.

In some embodiments, the Nectin-4 antibodies or antibody fragments bind human Nectin-4 with an affinity below 100 nM.

In some embodiments, the Nectin-4 antibodies or antibody fragments bind to an epitope in the N-terminal Ig-like V domain of Nectin-4. In an alternative embodiment the Nectin-4 antibodies or antibody fragments bind to an epitope in the Ig-like C domains of Nectin-4.

In some embodiments, the anti-Nectin-4 antibodies specifically bind human Nectin-4 as it occurs on the surface of tumor cells and induces the internalization of Nectin-4.

In some embodiments, the anti-Nectin-4 antibodies specifically bind human Nectin-4 as it occurs on the surface of tumor cells and directs ADCC-mediated killing of the tumor cells.

In some embodiments, the Nectin-4 antibodies or antibody fragments have cross reactive binding with cynomolgus monkey Nectin-4 with an EC50<5 nM. In other embodiments, the Nectin-4 antibodies or antibody fragments bind human and cynomolgus Nectin-4 and have cross reactive binding with rat and/or murine Nectin-4 with equivalent or lower binding affinity.

In some embodiments, the anti-Nectin-4 antibodies or antibody fragments thereof block including, partially block, a human Nectin-4/Nectin-1 binding interaction.

In some embodiments, the anti Nectin-4 antibodies or antibody fragments thereof block including, partially block, the human Nectin-4/TIGIT (T cell immunoreceptor with Ig and TIIM domains) binding interaction.

In some embodiments, the anti-Nectin-4 antibodies or antibody fragments thereof are incorporated into immunoconjugates comprising an anti-Nectin-4 antibody or antibody fragment thereof conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

In some embodiments, the Nectin-4 antibody is a monoclonal antibody. The present disclosure provides non-human parental (e.g. mouse) anti-Nectin-4 antibodies and antibody fragments thereof and methods of use thereof. A skilled practitioner will recognize that the disclosed antibodies can be modified for an intended use, such as conversion into a chimeric antibody or humanization for use as a human therapeutic antibody or fragment. In an alternative embodiment, the Nectin-4 antibody is a bispecific antibody.

In general, a humanized Nectin-4 antibody or fragment thereof may comprise substantially all of at least one, and typically two, variable domains, in which all, or substantially all of the hypervariable loops correspond to those of the disclosed parental murine anti-Nectin-4 antibodies disclosed herein, and all or substantially all of the framework (FR) regions derived from a suitable human consensus immunoglobulin sequence. The humanized antibody or fragment thereof may optionally comprise at least a portion of a human immunoglobulin constant region (Fc). For example, the disclosure includes any humanized version of the N4_mAb 6 antibody (comprising CDR regions derived from the VH sequence provided in SEQ ID NOs: 11 and the VL sequence provided in SEQ ID NO: 12), the N4_mAb 7 antibody (comprising CDR regions derived from the VH sequence provided in SEQ ID NOs: 13 and the VL sequence provided in SEQ ID NO: 14) and the N4_mAb 8 antibody (comprising CDR regions derived from the VH sequence provided in SEQ ID NOs: 15 and the VL sequence provided in SEQ ID NO: 16).

In some embodiments, the Nectin-4 antibody or antibody fragment is a recombinant antibody (e.g., a chimeric antibody, a humanized antibody, or a bispecific antibody) and comprises six (6) CDRs, all derived from the VH or VL domain of a single anti-Nectin-4 antibody disclosed herein. For example, a binding agent may comprise all six of the CDR regions of the anti-Nectin-4 antibody designated "N4_mAb 1." In a representative example, an antibody or antibody fragment thereof may comprise the amino acid sequences of SEQ ID NOs: 17-19 and SEQ ID NOs: 20-22, representing the CDR1, CDR2 and CDR3 of the variable heavy chain region and the CDR1, CDR2 and CDR3 of the variable light chain region of the murine anti-human Nectin-4 antibody referred to herein as "N4 mAb 1."

In some embodiments, the Nectin-4 antibody is a full-length antibody. In some embodiments, the anti-Nectin-4 antibody is an antibody fragment. In further embodiments, the antibody fragment is selected from the group consisting of: Fab, Fab', $F(ab')_2$, Fd, Fv, scFv and scFv-Fc fragment, a single-chain antibody, a minibody, and a diabody.

The Nectin-4 antibodies and antibody fragments thereof may be used for the treatment of cancer. Such methods for the treatment or cancer may comprise administering a composition or formulation that comprises a Nectin-4 antibody or antibody fragment thereof to a subject in need thereof. For example, the Nectin-4 antibody or antibody fragment thereof may be administered either alone (e.g., as a monotherapy) or in combination with other immunotherapeutic agent and/or a chemotherapy. In a particular embodiment, the Nectin-4 antibody or fragment thereof is used to prepare an ADC suitable to mediate the killing of cancer cells expressing Nectin-4.

BRIEF DESCRIPTION OF THE OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

FIG. 1 provides the amino acid sequences of the VH and VL domains of the murine anti-Nectin-4 antibodies and their respective CDR sequences (Kabat numbering). Sequence identifiers are provided and the CDRs are underlined in the variable domain sequences.

FIG. 2 shows binding of chimera Nectin-4 antibodies to recombinant Nectin-4 (extracellular domain) measured by ELISA.

Figure 3A:
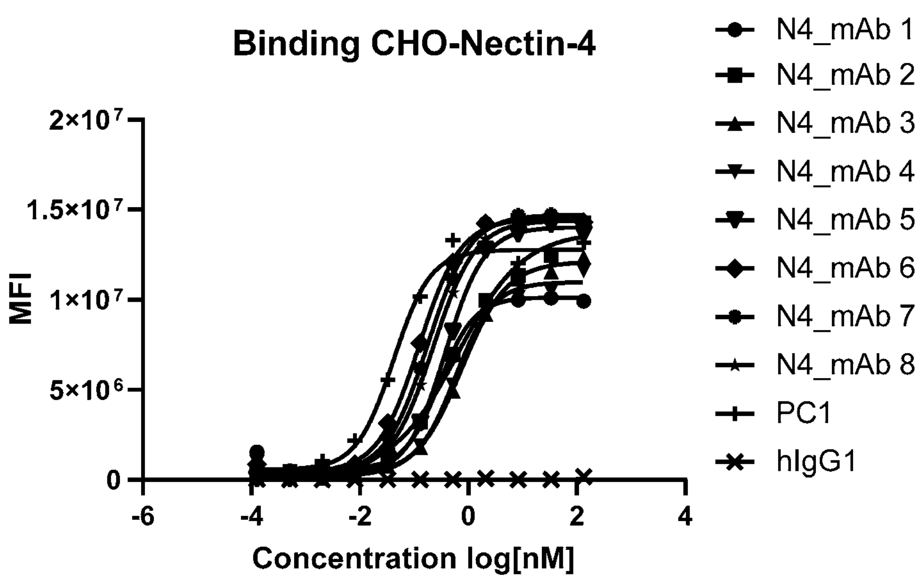
Figure 3B:
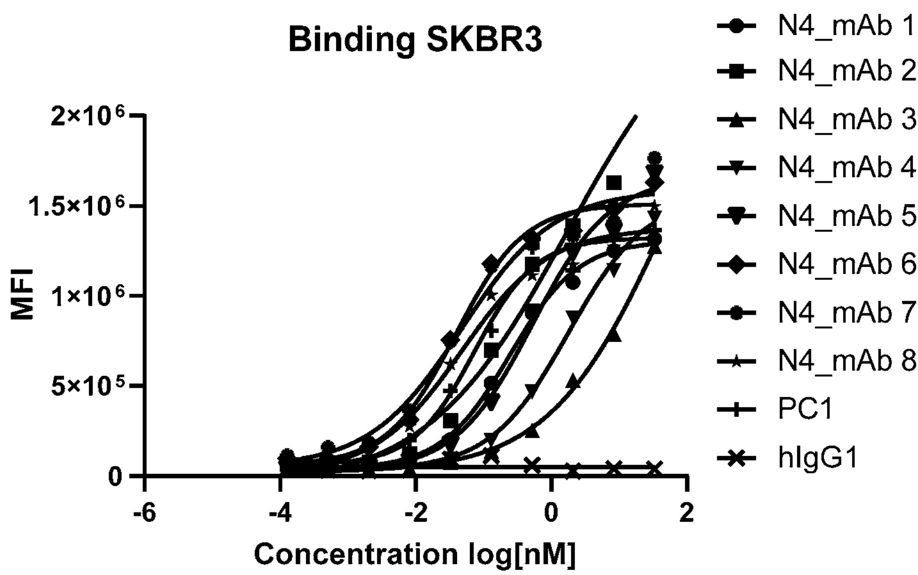

FIGS. 3A and 3B show binding of Nectin-4 antibodies to Nectin-4-expressing cells. FIG. 3A shows the binding of chimera Nectin-4 antibodies to CHO-Nectin-4 cells that ectopically expresses human Nectin-4. FIG. 3B shows the binding of chimera Nectin-4 antibodies to SKBR3 cells. SKBR3 is a human breast cancer cell line that endogenously expresses Nectin-4.

Figure 4A:
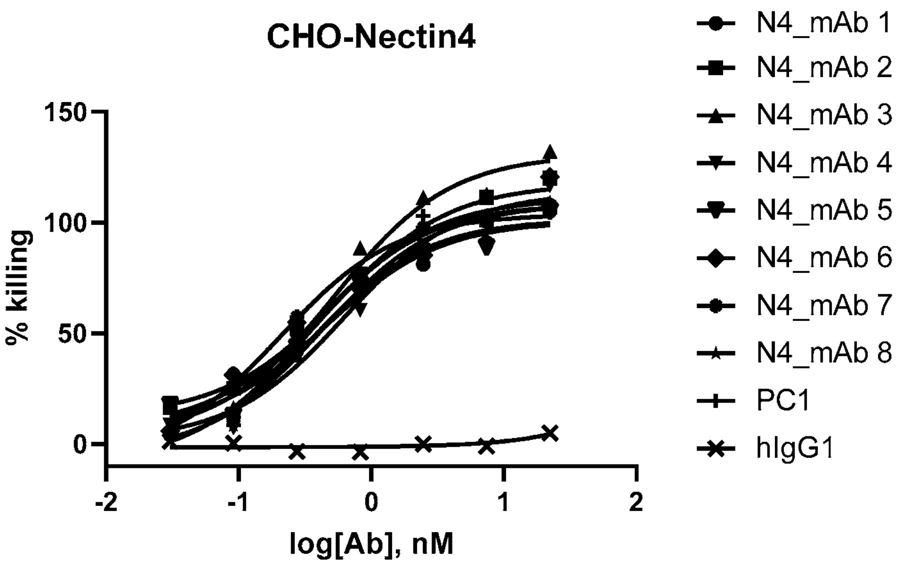
Figure 4B:
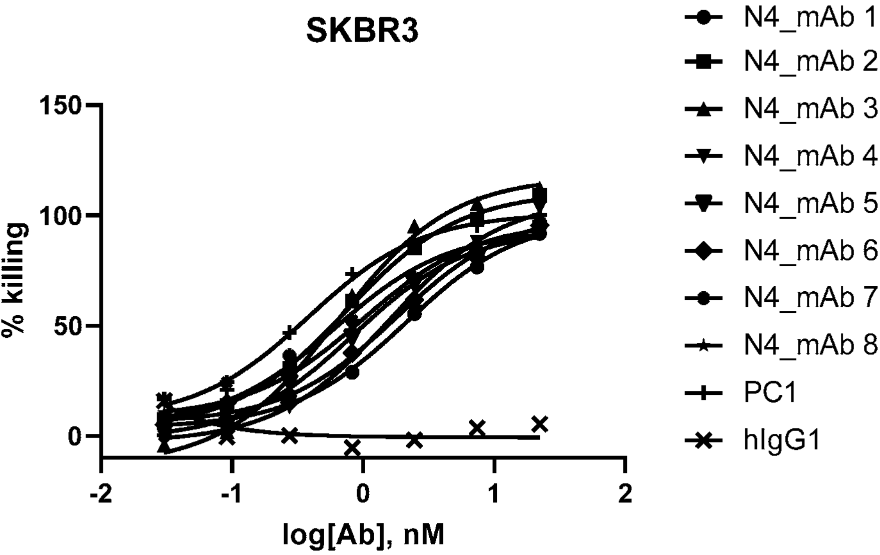

FIGS. 4A and 4B demonstrate Nectin-4 antibodies induce Nectin-4-dependent antibody endocytosis. FIG. 4A shows the endocytosis (manifests through indirect cell killing) of chimera Nectin-4 antibodies in CHO-Nectin-4 cells that ectopically expresses human Nectin-4. FIG. 4B shows the endocytosis of chimera Nectin-4 antibodies to SKBR3 cells. SKBR3 is a human breast cancer cell line that endogenously expresses Nectin-4.

Figure 5A:
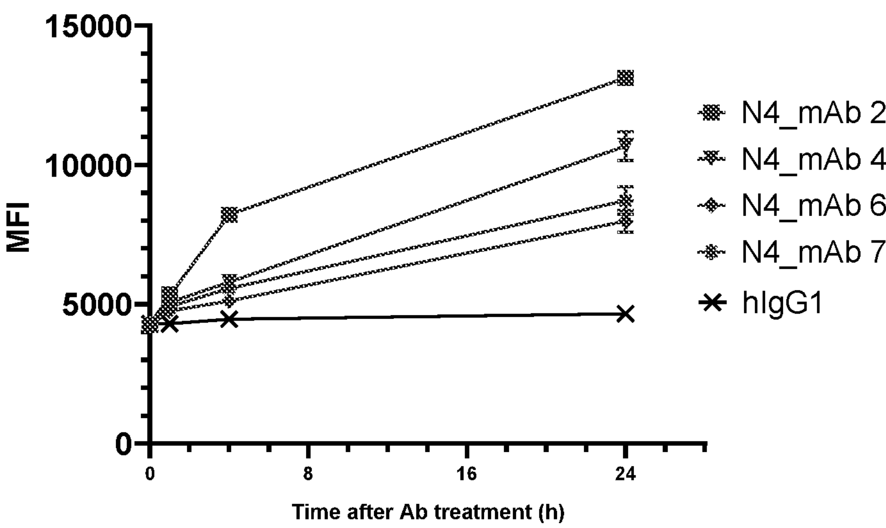
Figure 5B:
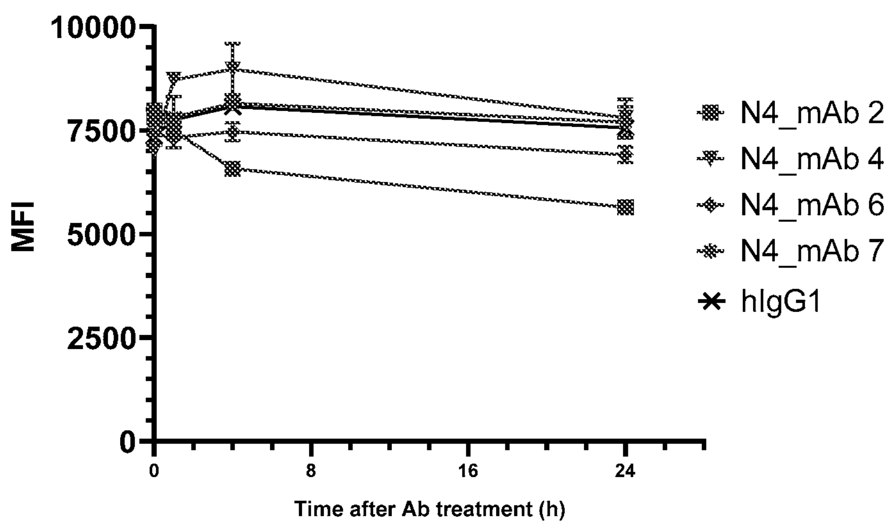

FIGS. 5A and 5B show the kinetics of Nectin-4 antibody internalization and coincidental membrane Nectin-4 level in T47D cells. T47D is a human breast cancer cell line that endogenously expresses Nectin-4. FIG. 5A shows the internalization kinetics of Nectin-4 antibodies. FIG. 5B shows the relative levels of membrane Nectin-4 protein measured at the same time points for internalization.

Figure 6A:
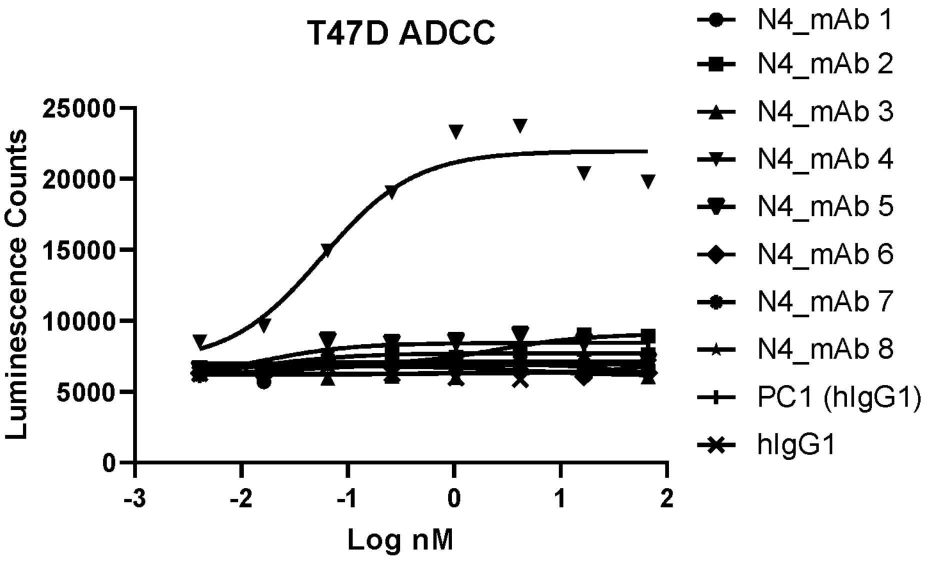
Figure 6B:
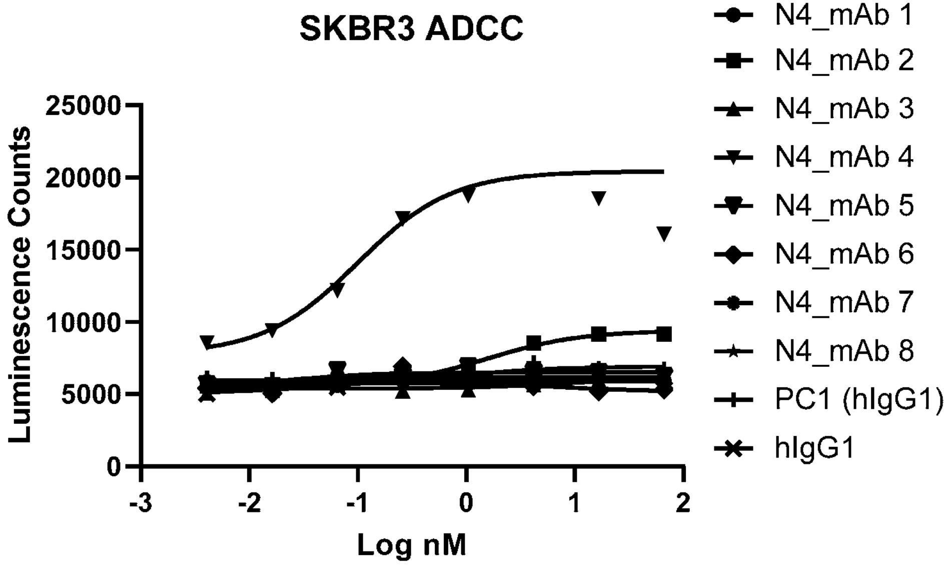

FIGS. 6A and 6B show the ability of Nectin-4 antibodies to induce antibody-dependent cellular cytotoxicity (ADCC). FIG. 6A shows the ADCC activity of Nectin-4 antibodies in T47D and FIG. 6B shows the ADCC activity in SKBR3 cells. Both T47D and SKBR3 are human breast cancer cell lines that endogenously expresses Nectin-4.

DETAILED DESCRIPTION

So that the disclosure may be more readily understood, certain technical and scientific terms are specifically defined below. Unless specifically defined elsewhere in this document, all other technical and scientific terms used herein have the meaning commonly understood by one of ordinary skill in the art to which this disclosure belongs.

Throughout this Disclosure the Following Abbreviations Will be Used:

mAb or Mab or MAb—Monoclonal antibody.

CDR—Complementarity determining region.

VH or VH—Heavy chain variable region.

VL or VL—Light chain variable region.

FR—Antibody framework region.

The term "Nectin-4" (N4), or "Nectin-4 protein" includes human Nectin-4, in particular the native-sequence polypeptide, isoforms, chimeric polypeptides, all homologs, fragments, and precursors of Nectin-4. The amino acid sequences for human, cynomolgus, rat and murine Nectin-4 are provided in NCBI Reference Sequences: NP_112178.2 (human) (SEQ ID NO: 61), XP_005541277.1 (cynomolgus monkey (SEQ ID NO: 62), NP_001102546.1 (rat)(SEQ ID NO: 63), and NP_082169.2 (mouse) (SEQ ID NO: 64). Orthologs of Nectin-4 share >99%, ~94% and ~92% homology to the human protein in cynomolgus monkey, rats and mice, respectively.

The term "Nectin-1," or "Nectin-1 protein" includes human Nectin-1 (N1), in particular the native-sequence polypeptide, isoforms, chimeric polypeptides, all homologs, fragments, and precursors of Nectin-1. The amino acid sequence for human Nectin-1 is provided in NCBI Reference Sequence NP_002846.3 (human) SEQ ID NO: 65.

As used herein, the term "TIGIT" refers to "T cell immunoreceptor with Ig and TIIM domains," a member of the PVR (poliovirus receptor) family of immunoglobin proteins, that binds to PVR/CD 155, Nectin-2/CD112 and Nectin-4 (Reches et al., *J Immunotherapy Cancer,* 8:e000266, 2020). TIGIT is also referred to as TIGIT, WUCAM, Vstm3 and Vsig9. Unless otherwise indicated, or clear from the context, references to TIGIT herein refer to human TIGIT.

The term "immunoglobulin superfamily" (IgSF) refers to a superfamily of proteins containing one or more immunoglobulin-like (Ig-like) domains. Most IgSF proteins are localized to a cell surface or secreted and function in the recognition, binding or adhesion processes of cells. There are about 500 non-antibody, non-T cell receptor (TCR) IgSF proteins encoded in the human genome. Most of the IgSF members are type I transmembrane proteins, which typically consist of an extracellular domain which contains one or more Ig-like domains either a variable (V) domain or a constant (C), a single transmembrane domain, and a cytoplasmic tail.

The term "antibody" herein is used in the broadest sense and encompasses various antibody structures, including but not limited to monoclonal antibodies, polyclonal antibodies, chimeric antibodies, humanized antibodies, and multi-specific antibodies (e.g., bispecific antibodies).

An exemplary antibody such as an IgG comprises two heavy chains and two light chains. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino terminus to carboxy-terminus in the following order: FR1, CDR1, FR2, CDR2, FR3, CDR3, FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1: "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987) J. Mol. Biol. 196:901-917.

The term "monoclonal antibody" as used herein refers to an antibody obtained from a population of substantially homogeneous antibodies, e.g., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to a recombinant antibody in which a portion of the heavy and/or light chain is identical with or homologous to corresponding sequences in antibodies derived from a particular species, or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity. In addition, complementarity determining region (CDR) grafting may be performed to alter certain properties of the antibody molecule including affinity or specificity. Typically, the variable domains are obtained from an antibody from an experimental animal (the "parental antibody"), such as a rodent, and the constant domain sequences are obtained from human antibodies, so that the resulting chimeric antibody can direct effector functions in a human subject and will be less likely to elicit an adverse immune response than the parental (e.g., mouse) antibody from which it is derived.

The term "humanized antibody" refers to an antibody that has been engineered to comprise one or more human framework regions in the variable region together with non-human (e.g., mouse, rat, or hamster) complementarity-determining regions (CDRs) of the heavy and/or light chain. In certain embodiments, a humanized antibody comprises sequences that are entirely human except for the CDR regions. Humanized antibodies are typically less immunogenic to humans, relative to non-humanized antibodies, and thus offer therapeutic benefits in certain situations. Those skilled in the art will be aware of humanized antibodies and will also be aware of suitable techniques for their generation. See for example, Hwang, W. Y. K., et al., Methods 36:35, 2005; Queen et al., Proc. Natl. Acad. Sci. USA, 86:10029-10033, 1989; Jones et al., Nature, 321:522-25, 1986: Riechmann et al., Nature, 332:323-27, 1988; Verhoeyen et al., Science, 239:1534-36, 1988: Orlandi et al., Proc. Natl. Acad. Sci. USA, 86:3833-37, 1989; U.S. Pat. Nos. 5,225,539; 5,530,101; 5,585,089; 5,693,761; 5,693,762; 6,180,370; and Selick et al., WO 90/07861, each of which is incorporated herein by reference in its entirety.

A "human antibody" is an antibody that possesses an amino-acid sequence corresponding to that of an antibody produced by a human and/or has been made using any of the techniques for making human antibodies known to one of skill in the art. This definition of a human antibody specifically excludes a humanized antibody comprising non-human antigen-binding residues. Human antibodies can be produced using various techniques known in the art, including methods described in Cole et al, Monoclonal Antibodies and Cancer Therapy, Alan R. Liss, p. 77 (1985); Boerner et al, J. Immunol, 147(1):86-95 (1991). See also van Dijk and van de Winkel, Curr. Opin. Pharmacol, 5: 368-74 (2001). Human antibodies can be prepared by administering the antigen to a transgenic animal that has been modified to produce such antibodies in response to antigenic challenge, but whose endogenous loci have been disabled, e.g., immunized HuMab mice (see, e.g., Nils Lonberg et al., 1994, Nature 368:856-859, WO 98/24884, WO 94/25585, WO 93/1227, WO 92/22645, WO 92/03918 and WO 01/09187 regarding HuMab mice), xenomice (see. e.g., U.S. Pat. Nos. 6,075,181 and 6,150,584 regarding XENOMOUSE™ technology) or Trianni mice (see, e.g., WO 2013/063391, WO 2017/035252 and WO 2017/136734).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called $\alpha$, $\delta$, $\varepsilon$, $\gamma$, and $\mu$, respectively.

The terms "antigen-binding domain" of an antibody (or simply "binding domain") of an antibody or similar terms refer to one or more fragments of an antibody that retain the ability to specifically bind to an antigen complex. Examples of binding fragments encompassed within the term "antigen-binding portion" of an antibody include (i) Fab fragments, monovalent fragments consisting of the VL, VH, CL and CH domains; (ii) F(ab')2 fragments, bivalent fragments comprising two Fab fragments linked by a disulfide bridge at the hinge region; (iii) Fd fragments consisting of the VH and CH domains: (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker.

The "variable domain" (V domain) of an antibody mediates binding and confers antigen specificity of a particular antibody. However, the variability is not evenly distributed across the 110-amino acid span of the variable domains. Instead, the V regions consist of relatively invariant stretches called framework regions (FRs) of 15-30 amino acids separated by shorter regions of extreme variability referred to herein as "hypervariable regions" or CDRs that are each 9-12 amino acids long. As will be appreciated by those in the art, the exact numbering and placement of the CDRs can be different among different numbering systems. However, it should be understood that the disclosure of a variable heavy and/or variable light sequence includes the disclosure of the associated CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3).

"Complementarity determining region" or "CDR" as the terms are used herein refer to short polypeptide sequences within the variable region of both heavy and light chain polypeptides that are primarily responsible for mediating specific antigen recognition. There are three CDRs (termed CDR1, CDR2, and CDR3) within each VL and each VH. Unless stated otherwise herein, CDR and framework regions are annotated according to the Kabat numbering scheme (Kabat E. A., et al., 1991, Sequences of proteins of Immunological interest, In: NIH Publication No. 91-3242, US Department of Health and Human Services, Bethesda, Md).

In other embodiments, the CDRs of an antibody can be determined according to MacCallum R M et al, (1996) J Mol Biol 262: 732-745, herein incorporated by reference in its entirety or according to the IMGT numbering system as described in Lefranc M P, (1999) The Immunologist 7: 132-136 and Lefranc M P et al, (1999) Nucleic Acids Res 27: 209-212, each of which is herein incorporated by reference in its entirety. See also, e.g. Martin A. "Protein Sequence and Structure Analysis of Antibody Variable Domains," in Antibody Engineering, Kontermann and Diibel, eds., Chapter 31, pp. 422-439, Springer-Verlag, Berlin (2001), herein incorporated by reference in its entirety. In other embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety.

"Framework" or "framework region" or "FR" refers to variable domain residues other than hypervariable region (HVR) residues. The FR of a variable domain generally consists of four FR domains: FR1, FR2, FR3, and FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), Vols. 1-3. In one embodiment, for the VL, the subgroup is subgroup kappa I as in Kabat et al., supra. In one embodiment, for the VH, the subgroup is subgroup III as in Kabat et al., supra.

The "hinge region" is generally defined as stretching from 216-238 (EU numbering) or 226-251 (Kabat numbering) of human IgG1. The hinge can be further divided into three distinct regions, the upper, middle (e.g., core), and lower hinge.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md. (1991).

A "blocking" antibody or an "antagonist" antibody is one which inhibits or reduces biological activity of the antigen it binds. Certain blocking antibodies or antagonist antibodies substantially or completely inhibit the biological activity of the antigen.

The term "effector functions," deriving from the interaction of an antibody Fc region with certain Fc receptors, include but are not necessarily limited to C1q binding, complement dependent cytotoxicity (CDC), Fc receptor binding, FcγR-mediated effector functions such as ADCC and antibody dependent cell-mediated phagocytosis (ADCP), and down regulation of a cell surface receptor. Such effector functions generally require the Fc region to be combined with an antigen binding domain (e.g., an antibody variable domain).

An "antibody that binds to the same epitope" as a reference antibody refers to an antibody that contacts an overlapping set of amino acid residues of the antigen as compared to the reference antibody or blocks binding of the reference antibody to its antigen in a competition assay by 50% or more. The amino acid residues of an antibody that contact an antigen can be determined, for example, by determining the crystal structure of the antibody in complex with the antigen or by performing hydrogen/deuterium exchange. In some embodiments, residues of an antibody that are within 5 Å the antigen are considered to contact the antigen. In some embodiments, an antibody that binds to the same epitope as a reference antibody blocks binding of the reference antibody to its antigen in a competition assay by 50% or more, and conversely, the reference antibody blocks binding of the antibody to its antigen in a competition assay by 50% or more.

The term "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab)2: diabodies; linear antibodies; single-chain antibody molecules (e.g., scFv). Papain digestion of antibodies produces two identical antigen-binding fragments, called "Fab" fragments, and a residual "Fc" fragment, a designation reflecting the ability to crystallize readily. The Fab fragment consists of an entire light (L) chain along with the variable region domain of the heavy (H) chain (VH), and the first constant domain of one heavy chain (CH1). Pepsin treatment of an antibody yields a single large F(ab)2 fragment which roughly corresponds to two disulfide linked Fab fragments having divalent antigen-binding activity and is still capable of cross-linking antigen. Fab fragments differ from Fab' fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The terms "antigen-binding domain" of an antibody (or simply "binding domain") of an antibody or similar terms refer to one or more fragments of an antibody that retain the ability to specifically bind to an antigen complex. Examples of binding fragments encompassed within the term "antigen-binding portion" of an antibody include (i) Fab fragments, monovalent fragments consisting of the VL, VH, CL and CH domains; (ii) $F(ab')_2$ fragments, bivalent fragments comprising two Fab fragments linked by a disulfide bridge at the hinge region; (iii) Fd fragments consisting of the VH and CH domains: (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker.

The term "multispecific antibody" is used in the broadest sense and specifically covers an antibody comprising a heavy chain variable domain (VH) and a light chain variable domain (VL), where the VH-VL unit has polyepitopic specificity (e.g., is capable of binding to two different epitopes on one biological molecule or each epitope on a different biological molecule). Such multispecific antibodies include, but are not limited to, full-length antibodies, antibodies having two or more VL and VH domains, bispecific diabodies and triabodies. "Polyepitopic specificity" refers to the ability to specifically bind to two or more different epitopes on the same or different target(s).

"Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 μM to 0.001 μM, 3 μM to 0.001 μM, 1 μM to 0.001 μM, 0.5 μM to 0.001 μM or 0.1 μM to 0.001 μM. "Monospecific" refers to the ability to bind only one epitope. Multi-specific antibodies can have structures similar to full immunoglobulin molecules and include Fc regions, for example IgG Fc regions. Such structures can include, but are not limited to, IgG-Fv, IgG-(scFv)2, DVD-Ig, (scFv)2-(scFv)2-Fc and (scFv)2-Fc-(scFv)2. In case of IgG-(scFv)2, the scFv can be attached to either the N-terminal or the C-terminal end of either the heavy chain or the light chain.

As used herein, the term "bispecific antibodies" refers to monoclonal, often human or humanized, antibodies that have binding specificities for at least two different antigens. In the disclosure, one of the binding specificities can be directed towards Nectin-4, the other can be for any other antigen, e.g., for a cell-surface protein, receptor, receptor subunit, tissue-specific antigen, virally derived protein, virally encoded envelope protein, bacterially derived protein, or bacterial surface protein, etc.

As used herein, the term "diabodies" refers to bivalent antibodies comprising two polypeptide chains, in which each polypeptide chain includes VH and VL domains joined by a linker that is too short (e.g., a linker composed of five amino acids) to allow for intramolecular association of VH and VL domains on the same peptide chain. This configuration forces each domain to pair with a complementary domain on another polypeptide chain so as to form a homodimeric structure. Accordingly, the term "triabodies" refers to trivalent antibodies comprising three peptide chains, each of which contains one VH domain and one VL domain joined by a linker that is exceedingly short (e.g., a linker composed of 1-2 amino acids) to permit intramolecular association of VH and VL domains within the same peptide chain.

The term an "isolated antibody" when used to describe the various antibodies disclosed herein, means an antibody that has been identified and separated and/or recovered from a cell or cell culture from which it was expressed. An isolated antibody or antibody fragment may including variants of the antibody or antibody fragment having one or more co- or post-translational modifications that arise during production, purification, and/or storage of the antibody or antibody fragment. Contaminant components of its natural environment are materials that would typically interfere with diagnostic or therapeutic uses for the polypeptide, and can include enzymes, hormones, and other proteinaceous or non-proteinaceous solutes. In some embodiments, an isolated antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) approaches. For a review of methods for assessment of antibody purity, see, for example, Flatman et al., *J. Chromatogr. B* 848:79-87, 2007. In a preferred embodiment, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain.

With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of 10-4 M or lower, alternatively 10-5 M or lower, alternatively 10-6 M or lower, alternatively 10-7 M or lower, alternatively 10-8 M or lower, alternatively 10-9 M or lower, alternatively 10-10 M or lower, alternatively 10-11 M or lower, alternatively 10-12 M or lower or a Kd in the range of 10-4 M to 10-6 M or 10-6 M to 10-10 M or 10-7 M to 10-9 M. As will be appreciated by the skilled artisan, affinity and KD values are inversely related. A high affinity for an antigen is measured by a low KD value. In one embodiment, the term "specific binding" refers to binding where a molecule binds to Nectin-4 or to a Nectin-4 epitope without substantially binding to any other polypeptide or polypeptide epitope.

As used herein the term "specifically binds Nectin-4" refers to the ability of an antibody, or antigen-binding fragment to recognize and bind endogenous human Nectin-4 as it occurs on the surface of normal or malignant cells, but not to human Nectin-1, Nectin-2 or Nectin-3 or any other human nectin family homolog.

The term "affinity," as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

An "epitope" is a term of art that indicates the site or sites of interaction between an antibody and its antigen(s). As described by (Janeway, C, Jr., P. Travers, et al. (2001). Immunobiology: the immune system in health and disease. Part II, Section 3-8. New York, Garland Publishing, Inc.): "An antibody generally recognizes only a small region on the surface of a large molecule such as a protein . . . [Certain epitopes] are likely to be composed of amino acids from different parts of the [antigen] polypeptide chain that have been brought together by protein folding. Antigenic determinants of this kind are known as conformational or discontinuous epitopes because the structure recognized is composed of segments of the protein that are discontinuous in the amino acid sequence of the antigen but are brought together in the three-dimensional structure. In contrast, an epitope composed of a single segment of polypeptide chain is termed a continuous or linear epitope" (Janeway, C. Jr., P. Travers, et al. (2001). Immunobiology: the immune system in health and disease. Part II, Section 3-8. New York, Garland Publishing, Inc.).

The term "KD", as used herein, refers to the equilibrium dissociation constant, which is obtained from the ratio of kd to ka (i.e., kd/ka) and is expressed as a molar concentration (M). KD values for antibodies can be determined using methods well established in the art. Preferred methods for determining the KD of an antibody include biolayer interferometry (BLI) analysis, preferably using a Fortebio Octet RED device, surface plasmon resonance, preferably using a biosensor system such as a BIACORE® surface plasmon resonance system, or flow cytometry and Scatchard analysis.

"EC50" with respect to an agent and a particular activity (e.g. binding to a cell, inhibition of enzymatic activity, activation or inhibition of an immune cell), refers to the efficient concentration of the agent which produces 50% of its maximum response or effect with respect to such activity. "EC100" with respect to an agent and a particular activity refers to the efficient concentration of the agent which produces its substantially maximum response with respect to such activity.

As used herein the term "antibody-drug conjugate" (ADC) refers to immunoconjugates consisting of recombinant monoclonal antibodies covalently linked to cytotoxic agents (known as payloads) via synthetic linkers. Immunoconjugates (Antibody-drug conjugates, ADCs) are a class of highly potent antibody-based cancer therapeutics. ADCs consist of recombinant monoclonal antibodies covalently linked to cytotoxic agents (known as payloads) via synthetic linkers. ADCs combine the specificity of monoclonal antibodies and the potency of small-molecule chemotherapy drugs, and facilitate the targeted delivery of highly cytotoxic small molecule drug moieties directly to tumor cells.

As used herein the term "endocytosis" refers to the process where eukaryotic cells internalize segments of the plasma membrane, cell-surface receptors, and components from the extracellular fluid. Endocytosis mechanisms include receptor-mediated endocytosis. The term "receptor-mediated endocytosis" refers to a biological mechanism by which a ligand, upon binding to its target, triggers membrane invagination and pinching, gets internalized and delivered into the cytosol or transferred to appropriate intracellular compartments.

The term "bystander effect" refers to target-cell mediated killing of healthy cells adjacent to tumor cells targeted for by an antibody drug conjugate. The bystander effect is generally caused by cellular efflux of hydrophobic cytotoxic drugs, capable of diffusing out of an antigen-positive target cell and into adjacent antigen-negative healthy cells. The presence or absence of the bystander effect can be attributed to aspects of the linker and conjugation chemistries used to produce an immunoconjugate.

As used herein the terms "antibody-based immunotherapy" and "immunotherapies" are used to broadly refer to any form of therapy that relies on the targeting specificity of an anti-Nectin-4 antibody, bispecific molecule, antigen-binding domain, or fusion protein comprising an anti-Nectin-4 antibody or antibody fragments or CDRs thereof, to mediate a direct or indirect effect on a Nectin-4 expressing cell. The terms are meant to encompass methods of treatment using naked antibodies, bispecific antibodies (including T cell engaging, NK cell engaging and other immune cell/effector cell engaging formats) antibody drug conjugates, cellular therapies using T cells (CAR-T) or NK cells (CAR-NK) engineered to comprise a Nectin-4-specific chimeric antigen receptor and oncolytic viruses comprising a Nectin-4 specific binding agent, and gene therapies by delivering the antigen binding sequences of the anti-Nectin-4 antibodies and express the corresponding antibody fragments in vivo.

Nectin Protein Family

The members of the Nectin family are expressed as single-pass type I glycoproteins, and are characterized by a common domain organization, consisting of three Ig-like domains in the ectodomain (membrane distal IgV domain followed by two IgC domains) a transmembrane region and a cytoplasmic domain (Samanta et al., *Cell Mol Life Sci,* 72(4):645-658, 2015) that binds to the actin cytoskeleton through the adaptor protein afadin.

Many viruses exploit IgSF member proteins to facilitate viral tropism, attachment and subsequent entry into host cells. Several members of the Nectin family were identified as viral receptors before finding their physiological functions as cell adhesion molecules. Initially, members of the Nectin family were independently identified by multiple groups as viral entry receptors and assigned names based on the observed functions. Nectin-1, -2 and -3 were originally described as molecules homologous to the poliovirus receptor (PVR, nec1-5, CD155) and as a consequence named Poliovirus Receptor Related (PRR) proteins (nectin1/PRR1/CD111, nectin2/PRR2/CD112 and nectin3/PRR3)(Reymond et al., *J Biol Chem,* 276(46):43205-15, 2001), and subsequently assigned the designations CD111, CD112 and CD 113, respectively. Nectin-4 was subsequently demonstrated to recognize the measles virus hemagglutinin (MV-H) and serves as an epithelial cell receptor for measles virus entry (Samanta et al., *Cell Mol Life Sci,* 72(4):645-658, 2015).

Nectin-4 (also known as poliovirus-receptor-like 4, PVRL4) was first described in 2001 as a new ligand for Nectin-1. More specifically, it was described as an afadin-associated member of the nectin family that trans-interacts with Nectin-1, but not Nectin-2, Nectin-3, or PVR through a V-domain interaction (Reymond et al., *J Biol Chem,* 276(46):43205-15, 2001).

Nectins function as cell adhesion molecules by first forming homo cis-dimers on the cell surface and then trans-dimers on adjacent cells in both a homophilic and heterophilic manner. The specificity of binding is different for each Nectin. Nectin-4 binds to itself and Nectin-1 (Reymond et al., *J Biol Chem,* 276(46):43205-15, 2001, Fabre et al., *J Biol Chem,* 277(30):27006-27013, 2002). Cell-cell contacts are thought to be initiated by an interaction between Nectins on adjacent cells. Subsequently, the cadherin-catenin complex is recruited to sites of Nectin-based intercellular adhesion and the trans-interaction of cadherins on adjacent cells occurs, thereby forming the adherens junction (Boylan et al., *Oncotarget,* 8(6):9717-9738, 2017).

The ectodomains of the Nectin proteins share between 30 and 55% amino acid sequence identity. Nectins are connected to the actin cytoskeleton afadin (an F-actin-binding protein), through a binding motif in their cytoplasmic domain, and participate in the organization of epithelial and endothelial junctions. In a complex interplay with other cell adhesion molecules (CAMs) and signal transduction molecules regulate several diverse physiological cellular activities such as movement, proliferation, survival, differentiation, polarization, and the entry of viruses.

The ability of Nectin family members to interact with additional cell surface molecules in mammals significantly expands their interaction network. Nectins are known to cis-interact with other cell surface membrane receptors, such as the platelet-derived growth factor receptor, the fibroblast growth factor receptor, the vascular endothelial growth factor receptor, the prolactin receptor, ErbB2, ErbB3, and ErbB4, and integrins, such as integrin $\alpha v\beta 3$ and integrin $\alpha 6\beta 4$, and regulate not only cell-cell adhesion but also cell migration, proliferation, differentiation, and survival (Kedashiro et al., *Sci Rep,* 9:18997, 2019).

Several members of the Nectin family can exert immunoregulatory functions as a consequence of a heterophilic trans-interaction with another member of the Immunoglobulin superfamily. These interactions are known to impact the functions of diverse immune cell types including natural killer (NK) cells, monocytes, dendritic cells (DCs), and T lymphocytes. Not only are several of the known nectin family interactors IgSF members, some Nectins are known to recognize common binding partners. For example, Nectin-2 and PVR both recognize CD226, TIGIT, and Nectin-3 (Duraivelan et al., *Sci Rep,* 10:9434, 2020).

A bioinformatics analysis using an algorithm to classify proteins into functionally related families predicted that five additional IgSF members, CD96 (TACTILE), CD226 (DNAM-1), TIGIT (WUCAM, VSTM3), CRTAM, and CD200 were functionally and evolutionarily related to Nectin and Nectin-like proteins and could represent binding partners for members of the Nectin family (Rubinstein et al., Structure, 21(5):766-776, 2013). To date, with the exception of CD200, all of these proteins have been reported to bind members of the Nectin-/Nectin-like family (Rubenstein, et al).

Nectin-4

Nectin-4 was first identified through a bioinformatics search using sequences from known nectin protein ectodomains to identify related sequences (Reymond et al., *J Biol Chem,* 276(46):43205-15, 2001). Human Nectin-4 was cloned from human trachea and described as an antigen with a restricted pattern of expression in normal human tissues.

Reymond and colleagues identified Nectin-4 as a novel ligand for Nectin-1 (Reymond et al., *J Biol Chem,* 276(46):43205-15, 2001), based on their findings that: i) a soluble chimeric recombinant Nectin-4 ectodomain (Nectin-4-Fc) interacts with cells expressing Nectin-1 but not with cells expressing PVR/CD155, Nectin-2, or Nectin-3, and conversely Nectin-1Fc binds to cells expressing Nectin-4; ii) Nectin-1-Fc precipitates Nectin-4 expressed in COS cells and iii) reciprocal in vitro physical interactions were observed between Nectin-4-Fc and Nectin-1-Fc soluble recombinant proteins (Reymond, N et al). A Nectin-4-Fc/Nectin-4-Fc interaction was also detected indicating that Nectin-4 possess both homophilic and heterophilic properties.

The human Nectin-4 gene contains nine exons encoding the Nectin-4 adhesion receptor, a 55.5 kDa protein containing 510 amino acids. According to protein knowledge database UniProtKb, Nectin-4 (Q96NY8) contains an N-terminal signal peptide (1-31 amino acids), an extracellular domain (32-349 amino acids) having three immunoglobulin-like sub-domains (V-type1 32-144 amino acids, C2-type1 148-237 amino acids, C2-type2 248-331 amino acids), a transmembrane domain (350-370 amino acids) and a cytoplasmic domain (371-510 amino acids).

It has been reported that the V-like domain of Nectin-4 is sufficient to mediate its trans-interaction with Nectin-1, and that the membrane proximal Nectin-4 C-like domains contribute to increase the affinity of the trans-interaction (Fabre et al., *J Biol Chem,* 277(30):27006-27013, 2002). Nectin-4 and Nectin-3 share a common binding region in the Nectin-1 V-like domain (Harrison et al., Nat Struct Mol Biol, 19(9):906-915, 2012).

It has also been reported that Nectin-4/Nectin-1 trans-interaction is blocked by an anti-Nectin-1 monoclonal antibody (R1.302) whose epitope is localized to the V-like domain of Nectin-1 (Reymond et al., *J Biol Chem,* 276(46):43205-15, 2001). Subsequent publications establish that a monoclonal antibody specific for the Ig-like V domain of Nectin-4 blocks adhesion of an ovarian cancer cell line engineered to overexpress human Nectin-4 (NIH:OVCAR5) to Nectin-1 (Boylan et al., *Oncotarget,* 8(6):9717-9738, 2017).

Targeting Nectin-4 for Cancer Immunotherapy

Nectin-4 was identified as a potential ADC target using suppression subtractive hybridization due to its high level of mRNA expression in bladder cancer (Challita-Eid et al., *Cancer Res,* 76(10):3003-13, 2016). Nectin-4 was originally described as a tumor-specific antigen (TSA) because of early publications reporting restricted expression of Nectin-4 by endothelial cells in human placenta (Reymond et al., *J Biol Chem,* 276(46):43205-15, 2001), a lack of expression in normal adult tissues, and re-expression in various cancer tissue including breast, ovarian, pancreatic and lung cancers (Fabre-Lafay et al., *BMC Cancer,* 7:73, 2007, Takano et al., *Cancer Res,* 69(16):6694-03, 2009, Derycke et al., *Am J Clin Pathol,* 5:835-845, 2010, Pavlova et al., *Elife,* 2:e00358, 2013, Nishiwada et al., *J Exp Clin Cancer Res,* 34(1):30, 2015, Challita-Eid et al., *Cancer Res,* 76(10):3003-13, 2016).

Immunohistochemical (IHC) study results using a murine antibody (M22-244b3) directed against the extracellular domain of human Nectin-4 and a panel of normal human tissue specimens (representing 36 human organs) demonstrated broader expression in normal tissues in low to moderate levels than was previously reported (Challita-Eid et al.) and identifies normal tissues that may have an increased risk of eliciting on target anti-Nectin-4 toxicities. Low levels of weak to moderate homogeneous staining have been reported in human skin keratinocytes, skin appendages (sweat glands and hair follicles, and the epithelia of bladder, stomach, breast, esophagus, and salivary gland (ducts) (Challita-Eid et al. Reymond et al., *J Biol Chem,* 276(46):43205-15, 2001, Brancati et al., *Am J Hum Gen,* 87:265-273, 2010), suggesting that Nectin-4 is more of a tumor-associated antigen (TAA) than a TSA.

Nectin-4 is overexpressed in multiple cancers, particularly urothelial, lung, pancreatic, breast and ovarian cancer (Challita-Eid et al., *Cancer Res,* 76(10):3003-13, 2016, Fabre-Lafay et al., *BMC Cancer,* 7:73, 2007, Takano et al., *Cancer Res,* 69(16):6694-03, 2009, Derycke et al., *Am J Clin Pathol,* 5:835-845, 2010). Extensive immunohistochemical of Nectin-4 expression in a human cancer tumor microarray (TMA) representing 34 tumors representing 7 different indications (e.g., bladder, breast, pancreatic, lung, ovarian, head/neck, and esophageal cancers) established that across evaluated cancer indications, 69% of TMA specimens were positive for Nectin-4. The highest frequencies for overall expression of Nectin-4 were observed for bladder, breast and pancreatic tumors. In ovarian, lung, head/neck and esophageal cancer samples, the prevalence of Nectin-4-positive samples with moderate to strong staining was generally lower (Chalittta-Eid et al.). The higher Nectin-4 expression levels observed in cancer, theoretically provides a therapeutic window characterized by an acceptable safety profile for anti-Nectin-4 targeted ADCs and antibody-based immunotherapies (Challita-Eid et al., *Cancer Res,* 76(10):3003-13, 2016, and Shim et al., *Biomolecules,* 10(3):360, 2020).

Early stages of epithelial cancer progression are characterized by genetic changes that confer ability to survive and proliferate in the absence of extracellular matrix anchorage. The ability of cancer cells to tolerate the loss of anchorage is critical for the survival of cancer cells and for the pathologic progression of tumorigenesis (e.g., invasion of the underlying stroma, extravasation into blood vessels and metastatic outgrowth as a distal site) (Pavlova et al., *Elife,* 2:e00358, 2013). Nectin-4 was identified in a gain of function screen for genes that enable cell proliferation independent of matrix anchorage in in TL-HMECs (hTERT-immortalized human mammary epithelial cells transduced with SV40 Large T antigen) (Pavlova et al., *Elife,* 2:e00358, 2013).

Pavlova et al. further reported that Nectin-4 drives the rapid association of TL-HMECs into multicellular clusters in suspension and that antibodies directed to the extracellular domain of Nectin-4 can be used to disrupt the observed cluster formation. Cell clustering was completely abrogated in the presence of anti-Nectin-4 antibodies. Similarly, an antibody targeting the extracellular region of Nectin-1 also inhibited Nectin-4-induced cell clustering.

Pavlova et al. further demonstrated that Nectin-4 promotes clustering of tumor cells with each other by engaging Nectin-1 receptors on adjacent cells, an interaction which triggers integrin 04/SHP-2/c-Src activation in a matrix attachment independent manner. Pavlova et al. proposed a model in which tumor-specific cell-cell contacts and signaling via Nectin-4/Nectin-1 interactions provides a surrogate for cell-matrix signaling and confers a survival advantage that enables anoikis (i.e., induction of apoptosis in cells upon loss of attachment to the extracellular matrix (ECM) and neighboring cells) evasion.

The results of a study conducted to determine the biological significance of Nectin-4 in cellular functions underlying ovarian cancer progression (i.e., cell adhesion, spheroid formation, migration and proliferation) report in vitro data demonstrating that a mAb against the IgV-like domain of Nectin-4 almost completely blocked ovarian cancer cell adhesion to Nectin-1 (Boylan et al., *Oncotarget,* 8(6):9717-9738, 2017). Boylan et al. note that Pavlova used the same anti-Nectin-4 antibody in a mouse xenograft model of breast cancer and observed disruption of tumor cell adhesion and reduced tumor growth in vivo compared to tumors treated with control IgG and based on the combined results speculate that blocking Nectin-4 cell adhesion may be an important component of therapeutic efficacy of anti-Nectin-4 antibodies used for cancer immunotherapy (Boylan et al.).

Publications reporting the results of preclinical studies evaluating the use of anti-Nectin-4 ADCs as monotherapy for the treatment of Nectin-4 expressing tumors validated the clinical development of anti-Nectin-4 antibody-based immunotherapeutics. For example, AGS-22 M6E ADC monotherapy was reported to inhibit the growth of tumors in four mouse xenograft models of human bladder, pancreatic, breast and lung cancer. A subsequent publication by M-Rabet et al. confirmed Nectin-4 as a therapeutic target for primary and metastatic triple negative breast cancer (TNBC) based on the observation that an ADC (N41 mAb-vcM-MAE) (WO 2017/042210) prepared using a different anti-Nectin-4 antibody induced complete and durable responses in vitro and in vivo in three models of TNBC developed in immunocompromised NSG mice, against primary tumors, metastatic lesions, and local relapses (M-Rabet et al., *Annals of Oncology,* 28(4):769-776, 2017).

Nectin-4/TIGIT

TIGIT belongs to the immunoglobulin superfamily, and is known to interact with members of the human nectin family, including poliovirus receptor (PVR or CD155 or Nec1-5), PVRL2 (CD112 or Nectin-2), CD 113 (Nectin-3) (Stanietsky et al., *Proc. Natl. Acad. Sci. USA,* 106:17585-63, 2009, Yu et al., *Nat Immunol,* 10:48-57, 2009, Boles et al., *Eur J Immunol,* 39:695-703, 2009).

TIGIT is expressed by most NK cells and multiple T cell subsets, including memory T cells and regulatory T cells (Yu et al. (2009) and on CD8+ tumor infiltrating lymphocytes (TILs) (Reches et al., *J Immunotherapy Cancer,* 8:e000266, 2020). After interaction with PVR or Nectin-2 TIGIT inhibits activation of T cell or NK cell effector functions. TIGIT's suppression of T cell activation has been attributed to the generation of immunoregulatory dendritic cells (Yu, X., et al. Nat. Immunol. (10) 48-57 (2009). PVR is a common ligand for TIGIT, TACTILE, and DNAM-1. DNAM-1 (CD226) is a costimulatory counter receptor that competes with both TIGIT for PVR engagement. However, the binding a affinities of the PVR/receptor interactions are vastly different, with TIGIT having a greater affinity for PVR than either DNAM-1 or TACTILE (Yu et al., 2009). The TIGIT dominance for the PVR ligand binding favors effector cell inhibition over effector cell co-stimulation. TIGIT has emerged as a particularly attractive target for cancer therapy due to its seemingly central role in limiting antitumor responses.

Nectin-4 has been recently identified as a functional ligand of TIGIT and the published data demonstrate that the Nectin-4/TIGIT interaction inhibits natural killer cell activity (Reches et al., *J Immunotherapy Cancer,* 8:e000266, 2020). The Reches et al. publication also reports that antibodies capable of blocking the Nectin-4/TIGIT interaction enhance tumor cell killing in vitro and in vivo (Reches et al., and WO 2019/215782) and speculates that blocking Nectin-4/TIGIT interaction using an anti-Nectin-4 antibody may lead to specific and significant induction of the immune response against tumors.

Anti-Nectin-4 Antibodies

The disclosed anti-Nectin-4 antibodies (N4_mAb 1 through N4_mAb 8) specifically bind human Nectin-4 and disrupt the Nectin-4/Nectin-1 and/or Nectin-4/TIGIT binding interaction. These antibodies and fragments thereof are characterized by unique sets of CDR sequences, specificity for Nectin-4, and are useful in cancer immunotherapy as monotherapy or in combination with other anti-cancer agents. More specifically, the disclosure relates to antibodies that bind to human Nectin-4, and to their use to modulate a Nectin-4-mediated activity of cells localized to the tumor microenvironment.

In some embodiments, the disclosed antibodies may be a monoclonal, chimeric, humanized or human antibody, or antigen-binding portions thereof, that specifically binds to human Nectin-4. In some embodiments, the anti-Nectin-4 antibodies or antibody fragments thereof exhibit one or more of the following structural and functional characteristics, alone or in combination: (a) is specific for human Nectin-4 (b) does not bind to human Nectin-1, human Nectin-2 or human Nectin-3, (c) binds to an epitope in the N-terminal Ig-like V domain of Nectin-4, (d) is internalized from the surface of Nectin-4 positive cells after binding (e) cross-reacts with cynomolgus Nectin-4: (f) cross-reacts with rat and/or murine Nectin-4 (g) disrupts including, reduces, the human Nectin-4/Nectin-1 binding interaction, (h) disrupts including, reduces, the human Nectin-4/TIGIT binding interaction, (i) reduces the level of cell surface protein expression of Nectin-4 on human tumor cells, or (j) directs ADCC of human cells expressing endogenous levels of Nectin-4.

Based on an in vitro assessment of maximum binding capacity, EC50, cell surface internalization and cytotoxicity the disclosed anti-Nectin-4 antibodies and fragments thereof can be evaluated for suitability for use as an ADC-based targeting antibody or antibody fragment for the treatment of cancer. In other embodiments the disclosed anti-Nectin-4 antibodies or fragments thereof may be used to induce antibody-dependent cytotoxicity (ADCC), complement-dependent cytotoxicity activity CDC), or and/or to block oncogenic receptor signals in the Nectin-4/Nectin-1 or Nectin-4/TIGIT axes, or to neutralize secreted Nectin-4.

In an embodiment, the anti-Nectin-4 antibodies or antibody fragments thereof comprise a VH having a set of CDRs (HCDR1, HCDR2, and HCDR3) disclosed in Table 1. For example, the anti-Nectin-4 antibodies or antibody fragments thereof may comprise a set of CDRs corresponding to those CDRs in one or more of the anti-Nectin-4 antibodies disclosed in Table 1 (e.g., the CDRs of the N4_mAb1).

In another embodiment, the anti-Nectin-4 antibodies or antibody fragments thereof comprise a VL having a set of CDRs (LCDR1, LCDR2, and LCDR3) as disclosed in Table 2. For example, the anti-Nectin-4 antibodies or antibody fragments thereof may comprise a set of CDRs corresponding to those CDRs in one or more of the anti-Nectin-4 antibodies disclosed in Table 2 (e.g., the CDRs of the N4_mAb 2).

In an alternative embodiment, the anti-Nectin-4 antibodies or antibody fragments thereof comprise a VH having a set of CDRs (HCDR1, HCDR2, and HCDR3) as disclosed in Table 1, and a VL having a set of CDRs (LCDR1, LCDR2, and LCDR3) as disclosed in Table 2. In an embodiment, the antibody may be a monoclonal, chimeric, bispecific, humanized or human antibody, or antigen-binding portions thereof that specifically binds to human Nectin-4. In one embodiment, the anti-Nectin-4 antibody or antibody fragment thereof comprises all six of the CDR regions of the N4_mAb 1, N4_mAb 2, N4_mAb 3, N4_mAb 4, N4_mAb 5, N4_mAb 6, N4_mAb 7 or N4_mAb 8 antibodies formatted as a chimeric or a humanized antibody.

TABLE 1

CDR Sequences of Anti-Nectin-4 Antibody Variable Heavy Chains

| Anti-Nectin-4 Ab | CDR1 | CDR2 | CDR3 |
|---|---|---|---|
| mAb 1 | NYGVN (SEQ ID NO: 17) | VIWSGGSTDYNAAFIS (SEQ ID NO: 18) | EGYDGYAMDY (SEQ ID NO: 19) |
| mAb 2 | TYGAH (SEQ ID NO: 23) | VIWRGGSTDYNAAFMS (SEQ ID NO: 24) | IGYDGYAMDN (SEQ ID NO: 25) |
| mAb 3 | DTYMH (SEQ ID NO: 29) | RIDPANGNTKYDPKFQG (SEQ ID NO: 30) | YYGSSYFAMDC (SEQ ID NO: 31) |
| mAb 4 | SAYNWH (SEQ ID NO: 35) | YIHYSGRTNYNPSLKS (SEQ ID NO: 36) | WITTATGWYLDV (SEQ ID NO: 37) |
| mAb 5 | GHYMH (SEQ ID NO: 41) | RVNPNNGGSSYNQKFKD (SEQ ID NO: 42) | DPLGGSYGFAY (SEQ ID NO: 43) |

TABLE 1-continued

CDR Sequences of Anti-Nectin-4 Antibody Variable Heavy Chains

| Anti-Nectin-4 Ab | CDR1 | CDR2 | CDR3 |
|---|---|---|---|
| mAb 6 | TYYIH (SEQ ID NO: 47) | WIYPGNVNTKYTENFKD (SEQ ID NO: 48) | GLYYFDF (SEQ ID NO: 49) |
| mAb 7 | TYYIH (SEQ ID NO: 47 | WIYPGNAGIKSNEKFKG (SEQ ID NO: 53) | GVYFFDY (SEQ ID NO: 54) |
| mAb 8 | SYYIH (SEQ ID NO: 57) | WIYPGNVNTKYNENFRD (SEQ ID NO: 58) | GIYYFDY (SEQ ID NO: 59) |

TABLE 2

CDR Sequences of Anti-Nectin-4 Variable Light Chains

| Anti-Nectin-4 Ab | CDR1 | CDR2 | CDR3 |
|---|---|---|---|
| mAb 1 | RASENIFSSLA (SEQ ID NO: 20) | GATNLAD (SEQ ID NO: 21) | QHFWGNPWT (SEQ ID NO: 22) |
| mAb 2 | RTSENIHNYLA (SEQ ID NO: 26) | NAKTLAD (SEQ ID NO: 27) | QHFWSSPWT (SEQ ID NO: 28) |
| mAb 3 | KASQDVSTAVA (SEQ ID NO: 32) | WASTRHT (SEQ ID NO: 33) | QQHYSTPLT (SEQ ID NO: 34) |
| mAb 4 | RASESVANYGISFMN (SEQ ID NO: 38) | AASNQGS (SEQ ID NO: 39) | QQSKEVPWT (SEQ ID NO: 40) |
| mAb 5 | RASQSVTTSSYSYMH (SEQ ID NO: 44) | YASNLES (SEQ ID NO: 45) | QHSWEIPYT (SEQ ID NO: 46) |
| mAb 6 | KASQSVNNDVA (SEQ ID NO: 50) | YASNRDT (SEQ ID NO: 51) | QQDYSSPYT (SEQ ID NO: 52) |
| mAb 7 | KASQSVNNDVS (SEQ ID NO: 55) | YASNRYT (SEQ ID NO: 56) | QQDYSSPYT (SEQ ID NO: 52) |
| mAb 8 | KASQSVNNDVA (SEQ ID NO: 50) | YASNRDT (SEQ ID NO: 51) | HQDYSSPFT (SEQ ID NO: 60) |

In an embodiment, the anti-Nectin-4 antibodies or antibody fragments thereof comprise a VH having a set of complementarity-determining regions (CDR1, CDR2, and CDR3) selected from the group consisting of:
- (i) CDR1: SEQ ID NO: 17, CDR2: SEQ ID NO: 18, CDR3: SEQ ID NO: 19;
- (ii) CDR1: SEQ ID NO: 23, CDR2: SEQ ID NO: 24, CDR3: SEQ ID NO: 25;
- (iii) CDR1: SEQ ID NO: 29, CDR2: SEQ ID NO: 30, CDR3: SEQ ID NO: 31;
- (iv) CDR1: SEQ ID NO: 35, CDR2: SEQ ID NO: 36, CDR3: SEQ ID NO: 37;
- (v) CDR1: SEQ ID NO: 41, CDR2: SEQ ID NO: 42, CDR3: SEQ ID NO: 43;

- (vi) CDR1: SEQ ID NO: 47, CDR2: SEQ ID NO: 48, CDR3: SEQ ID NO: 49;
- (vii) CDR1: SEQ ID NO: 47, CDR2: SEQ ID NO: 53, CDR3: SEQ ID NO: 54; and
- (viii) CDR1: SEQ ID NO: 57, CDR2: SEQ ID NO: 58, CDR3: SEQ ID NO: 59.

In an embodiment, the anti-Nectin-4 antibodies or antibody fragments thereof comprise a VL having a set of complementarity-determining regions (CDR1, CDR2, and CDR3) selected from the group consisting of:
- (i) CDR1: SEQ ID NO: 20, CDR2: SEQ ID NO: 21 CDR3: SEQ ID NO: 22;
- (ii) CDR1: SEQ ID NO: 26, CDR2: SEQ ID NO: 27, CDR3: SEQ ID NO: 28;
- (iii) CDR1: SEQ ID NO: 32, CDR2: SEQ ID NO: 33, CDR3: SEQ ID NO: 34;
- (iv) CDR1: SEQ ID NO: 38, CDR2: SEQ ID NO: 39, CDR3: SEQ ID NO:40;
- (v) CDR1: SEQ ID NO: 44, CDR2: SEQ ID NO: 45, CDR3: SEQ ID NO: 46;
- (vi) CDR1: SEQ ID NO: 50, CDR2: SEQ ID NO: 51, CDR3: SEQ ID NO: 52;
- (vii) CDR1: SEQ ID NO: 55, CDR2: SEQ ID NO: 56, CDR3: SEQ ID NO: 52 and
- (viii) CDR1: SEQ ID NO: 50, CDR2: SEQ ID NO: 51, CDR3: SEQ ID NO: 60.

In another embodiment, the anti-Nectin-4 antibodies or antibody fragments thereof comprise:
- (a) a VH having a set of complementarity-determining regions (CDR1, CDR2, and CDR3) selected from the group consisting of:
  - (i) CDR1: SEQ ID NO: 17, CDR2: SEQ ID NO: 18, CDR3: SEQ ID NO: 19;
  - (ii) CDR1: SEQ ID NO: 23, CDR2: SEQ ID NO: 24, CDR3: SEQ ID NO: 25;
  - (iii) CDR1: SEQ ID NO: 29, CDR2: SEQ ID NO: 30, CDR3: SEQ ID NO: 31;
  - (iv) CDR1: SEQ ID NO: 35, CDR2: SEQ ID NO: 36, CDR3: SEQ ID NO: 37;
  - (v) CDR1: SEQ ID NO: 41, CDR2: SEQ ID NO: 42, CDR3: SEQ ID NO: 43;
  - (vi) CDR1: SEQ ID NO: 47, CDR2: SEQ ID NO: 48, CDR3: SEQ ID NO: 49;
  - (vii) CDR1: SEQ ID NO: 47, CDR2: SEQ ID NO: 53, CDR3: SEQ ID NO: 54; and
  - (viii) CDR1: SEQ ID NO: 57, CDR2: SEQ ID NO: 58, CDR3: SEQ ID NO: 59, and
- (b) a VL having a set of complementarity-determining regions (CDR1, CDR2, and CDR3) selected from the group consisting of:
  - (i) CDR1: SEQ ID NO: 20, CDR2: SEQ ID NO: 21 CDR3: SEQ ID NO: 22;
  - (ii) CDR1: SEQ ID NO: 26, CDR2: SEQ ID NO: 27, CDR3: SEQ ID NO: 28;
  - (iii) CDR1: SEQ ID NO: 32, CDR2: SEQ ID NO: 33, CDR3: SEQ ID NO: 34;
  - (iv) CDR1: SEQ ID NO: 38, CDR2: SEQ ID NO: 39, CDR3: SEQ ID NO:40;
  - (v) CDR1: SEQ ID NO: 44, CDR2: SEQ ID NO: 45, CDR3: SEQ ID NO: 46;
  - (vi) CDR1: SEQ ID NO: 50, CDR2: SEQ ID NO: 51, CDR3: SEQ ID NO: 52;
  - (vii) CDR1: SEQ ID NO: 55, CDR2: SEQ ID NO: 56, CDR3: SEQ ID NO: 52 and
  - (viii) CDR1: SEQ ID NO: 50, CDR2: SEQ ID NO: 51, CDR3: SEQ ID NO: 60.

In an embodiment, the anti-Nectin-4 antibodies or antibody fragments thereof comprise a combination of a VH and a VL having a set of complementarity-determining regions (CDR1, CDR2 and CDR3) selected from the group consisting of:

(i) VH: CDR1: SEQ ID NO: 17, CDR2: SEQ ID NO: 18, CDR3: SEQ ID NO: 19, VL: CDR1: SEQ ID NO: 20, CDR2: SEQ ID NO: 21, CDR3: SEQ ID NO: 22;

ii) VH: CDR1: SEQ ID NO: 23, CDR2: SEQ ID NO: 24, CDR3: SEQ ID NO: 25, VL: CDR1: SEQ ID NO: 26, CDR2: SEQ ID NO: 27, CDR3: SEQ ID NO: 28;

(iii) VH: CDR1: SEQ ID NO: 29, CDR2: SEQ ID NO: 30, CDR3: SEQ ID NO: 31, VL: CDR1: SEQ ID NO: 32, CDR2: SEQ ID NO: 33, CDR3: SEQ ID NO: 34;

(iv) VH: CDR1: SEQ ID NO: 35 CDR2: SEQ ID NO: 36, CDR3: SEQ ID NO: 37, VL: CDR1: SEQ ID NO: 38, CDR2: SEQ ID NO: 39, CDR3: SEQ ID NO: 40;

(v) VH: CDR1: SEQ ID NO: 41, CDR2: SEQ ID NO: 42, CDR3: SEQ ID NO: 43, VL: CDR1: SEQ ID NO: 44, CDR2: SEQ ID NO: 45, CDR3: SEQ ID NO: 46;

(vi) VH: CDR1: SEQ ID NO: 47, CDR2: SEQ ID NO: 48, CDR3: SEQ ID NO: 49, VL: CDR1: SEQ ID NO: 50, CDR2: SEQ ID NO: 51, CDR3: SEQ ID NO: 52;

(vii) VH: CDR1: SEQ ID NO: 47, CDR2: SEQ ID NO: 53, CDR3: SEQ ID NO: 54, VL: CDR1: SEQ ID NO: 55, CDR2: SEQ ID NO: 56, CDR3: SEQ ID NO: 52;

(viii) VH: CDR1: SEQ ID NO:57, CDR2: SEQ ID NO: 58, CDR3: SEQ ID NO: 59, and VL: CDR1: SEQ ID NO: 50 CDR2: SEQ ID NO: 51, CDR3: SEQ ID NO: 60.

In an embodiment, the anti-Nectin-4 antibodies or antibody fragments thereof comprise a variable heavy chain sequence selected from the group consisting of: SEQ ID NOs: 1, 3, 5, 7, 9, 11, 13, and 15; and/or a variable light chain sequence selected from the group consisting of: SEQ ID NOs: 2, 4, 6, 8, 10, 12, 14, and 16.

In an embodiment, the anti-Nectin-4 antibodies or antibody fragments thereof comprise a pair of variable heavy chain and variable light chain sequences, selected from the following combinations: a variable heavy chain sequence comprising SEQ ID NO: 1 and a variable light chain sequence comprising SEQ ID NO: 2; a variable heavy chain sequence comprising SEQ ID NO: 3 and a variable light chain sequence comprising SEQ ID NO: 4; a variable heavy chain sequence comprising SEQ ID NO: 5 and a variable light chain sequence comprising SEQ ID NO: 6; a variable heavy chain sequence comprising SEQ ID NO: 7 and a variable light chain sequence comprising SEQ ID NO: 8; a variable heavy chain sequence comprising SEQ ID NO: 9 and a variable light chain sequence comprising SEQ ID NO: 10; a variable heavy chain sequence comprising SEQ ID NO: 11 and a variable light chain sequence comprising SEQ ID NO: 12; a variable heavy chain sequence comprising SEQ ID NO: 13 and a variable light chain sequence comprising SEQ ID NO: 14; a variable heavy chain sequence comprising SEQ ID NO: 15 and a variable light chain sequence comprising SEQ ID NO: 16. The skilled person will further understand that the variable light and variable heavy chains may be independently selected, or mixed and matched, to prepare an anti-Nectin-4 antibody or antibody fragment thereof comprising a combination of variable heavy and variable light chain that is distinct from the pairings identified above.

In an alternative embodiment, the anti-Nectin-4 antibodies or antibody fragments thereof comprise a pair of variable heavy chain and variable light chain sequences, selected from the following combinations: a variable heavy chain sequence that is 90%, 95%, or 99% identical to SEQ ID NO: 1 and a variable light chain sequence that is 90%, 95%, or 99% identical to SEQ ID NO: 2; a variable heavy chain sequence that is 90%, 95%, or 99% identical to SEQ ID NO: 3 and a variable light chain sequence that is 90%, 95%, or 99% identical to SEQ ID NO: 4; a variable heavy chain sequence that is 90%, 95%, or 99% identical to SEQ ID NO: 5 and a variable light chain sequence that is 90%, 95%, or 99% identical to SEQ ID NO: 6; a variable heavy chain sequence that is 90%, 95%, or 99% identical to SEQ ID NO: 7 and a variable light chain sequence that is 90%, 95%, or 99% identical to SEQ ID NO: 8; a variable heavy chain sequence that is 90%, 95%, or 99% identical to SEQ ID NO: 9 and a variable light chain sequence that is 90%, 95%, or 99% identical to SEQ ID NO: 10; a variable heavy chain sequence that is 90%, 95%, or 99% identical to SEQ ID NO: 11 and a variable light chain sequence that is 90%, 95%, or 99% identical to SEQ ID NO: 12; a variable heavy chain sequence that is 90%, 95%, or 99% identical to SEQ ID NO: 13 and a variable light chain sequence that is 90%, 95%, or 99% identical to SEQ ID NO: 14; a variable heavy chain sequence that is 90%, 95%, or 99% identical to SEQ ID NO: 15 and a variable light chain sequence that is 90%, 95%, or 99% identical to SEQ ID NO: 16.

Advantageously, such antibodies or fragments thereof retain binding specificity for Nectin-4. The skilled person will further understand that the variable light and variable heavy chains may be independently selected, or mixed and matched, to prepare an anti-Nectin-4 antibody comprising a combination of variable heavy and variable light chain that is distinct from the pairings identified above.

In some embodiments, the antibody is a full-length antibody. In other embodiments, the antibody is an antibody fragment including, for example, an antibody fragment selected from the group consisting of: Fab, Fab', $F(ab')_2$, Fv, domain antibodies (dAbs), and complementarity determining region (CDR) fragments, single-chain antibodies (scFv), chimeric antibodies, diabodies, triabodies, tetrabodies, miniantibodies, and polypeptides that contain at least a portion of an immunoglobulin that is sufficient to confer Nectin-4 specific binding to the polypeptide.

In some embodiments, a variable region domain of an anti-Nectin-4 antibody disclosed herein may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly, a VL domain may be linked to a CK domain or a fragment thereof. In this way, for example, the antibody may be a Fab fragment wherein the antigen binding domain contains associated VH and VL domains covalently linked at their C-termini to a CH1 and CK domain, respectively. The CH1 domain may be extended with further amino acids, for example to provide a hinge region or a portion of a hinge region domain as found in a Fab fragment, or to provide further domains, such as antibody CH2 and CH3 domains.

Thus, in one embodiment, the antibody fragment comprises at least one CDR as described herein. The antibody fragment may comprise at least two, three, four, five, or six CDRs as described herein. The antibody fragment further may comprise at least one variable region domain of an antibody described herein. The variable region domain may be of any size or amino acid composition and will generally comprise at least one CDR sequence responsible for binding to human Nectin-4, for example, CDR-H1, CDR-H2, CDR- H3, CDR-L1, CDR-L2, and/or CDR-L3 as described herein, and which is adjacent to or in frame with one or more framework sequences.

In some embodiments, the anti-Nectin-4 antibody is a monoclonal antibody. In some embodiments, the anti-Nectin-4 antibody is a human antibody. In alternative embodiments, the anti-Nectin-4 antibody is a murine antibody. In some embodiments, the anti-Nectin-4 antibody is a chimeric antibody, a bispecific antibody, or a humanized antibody.

In some embodiments, the anti-Nectin-4 antibodies or antibody fragments thereof exhibit one or more of the following structural and functional characteristics, alone or in combination: (a) is specific for human Nectin-4 (b) does not bind to human Nectin-1, human Nectin-2 or human Nectin-3, (c) binds to an epitope in the N-terminal Ig-like V domain of Nectin-4, (d) is internalized from the surface of Nectin-4 positive cells after binding (e) cross-reacts with cynomolgus Nectin-4: (f) cross-reacts with rat and/or murine Nectin-4 (g) disrupts, including, reduces, the human Nectin-4/Nectin-1 binding interaction, (h) disrupts, including reduces, the human Nectin-4/TIGIT binding interaction, (i) reduces the level of cell surface protein expression of Nectin-4 on human tumor cells, or (j) directs ADCC of human cells expressing endogenous levels of Nectin-4.

In some embodiments, the anti-Nectin-4 antibodies or antibody fragments thereof comprise one or more conservative amino acid substitutions. A person of skill in the art will recognize that a conservative amino acid substitution is a substitution of one amino acid with another amino acid that has similar structural or chemical properties, such as, for example, a similar side chain. Exemplary conservative substitutions are described in the art, for example, in Watson et al., Molecular Biology of the Gene, The Benjamin/Cummings Publication Company, 4th Ed. (1987).

"Conservative modifications" refer to amino acid modifications that do not significantly affect or alter the binding characteristics of the antibody containing the amino acid sequences. Conservative modifications include amino acid substitutions, additions and deletions. Conservative substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al. (1998) Acta Physiol Scand Suppl 643: 55-67; Sasaki et al. (1998) Adv Biophys 35: 1-24). Amino acid substitutions to the antibodies of the disclosure may be made by known methods for example by PCR mutagenesis (U.S. Pat. No. 4,683,195).

In some embodiments, the anti-Nectin-4 antibodies or antibody fragments thereof comprise a variable heavy chain sequence that comprises an amino acid sequence with at least about 95%, about 96%, about 97%, about 98%, or about 99%, sequence identity to the amino acid sequence set forth in SEQ ID NOs: 1, 3, 5, 7, 9, 11, 13 or 15. In other embodiments, the anti-Nectin-4 antibodies or antibody fragments thereof retains the binding and/or functional activity of an anti-Nectin-4 antibody or antibody fragment thereof that comprises the variable heavy chain sequence of SEQ ID NOs: 1, 3, 5, 7, 9, 11, 13 or 15. In still further embodiments, the anti-Nectin-4 antibodies or antibody fragments thereof comprise the variable heavy chain sequence of SEQ ID NOs: 1, 3, 5, 7, 9, 11, 13 or 15 and have one or more conservative amino acid substitutions, e.g., 1, 2, 3, 4, 5, 1-2, 1-3, 1-4 or 1-5 conservative amino acid substitutions in the heavy chain variable sequence. In yet further embodiments, the one or more conservative amino acid substitutions fall within one or more framework regions in SEQ ID NOs: 1, 3, 5, 7, 9, 11, 13 or (based on the numbering system of Kabat).

In particular embodiments, the anti-Nectin-4 antibody or antibody fragment thereof comprises a variable heavy chain sequence with at least about 95%, about 96%, about 97%, about 98%, or about 99% sequence identity to the anti-Nectin-4 heavy chain variable region sequence set forth in SEQ ID NOs: NOs: 1, 3, 5, 7, 9, 11, 13 or 15, comprises one or more conservative amino acid substitutions in a framework region (based on the numbering system of Kabat), and retains the binding and/or functional activity of an anti-Nectin-4 antibody or antibody fragment thereof that comprises a variable heavy chain sequence as set forth in SEQ ID NOs: 1, 3, 5, 7, 9, 11, 13 or 15 and a variable light chain sequence as set forth in SEQ ID NOs: 2, 4, 6, 8, 10, 12, 14 or 16.

In some embodiments, the anti-Nectin-4 antibodies or antibody fragments thereof comprise a variable light chain sequence that comprises an amino acid sequence with at least about 95%, about 96%, about 97%, about 98%, or about 99%, sequence identity to the amino acid sequence set forth in SEQ ID NOs: 2, 4, 6, 8, 10, 12, 14 or 16. In other embodiments, the anti-Nectin-4 antibodies or antibody fragments thereof retains the binding and/or functional activity of an anti-Nectin-4 antibody or antibody fragment thereof that comprises the variable light chain sequence of SEQ ID NOs: 2, 4, 6, 8, 10, 12, 14 or 16. In still further embodiments, the anti-Nectin-4 antibodies or antibody fragments thereof comprise the variable light chain sequence of SEQ ID NOs: 2, 4, 6, 8, 10, 12, 14 or 16 and have one or more conservative amino acid substitutions, e.g., 1, 2, 3, 4, 5, 1-2, 1-3, 1-4 or 1-5 conservative amino acid substitutions in the light chain variable sequence. In yet further embodiments, the one or more conservative amino acid substitutions fall within one or more framework regions in SEQ ID NOs: 2, 4, 6, 8, 10, 12, 14 or 16 (based on the numbering system of Kabat).

In particular embodiments, the anti-Nectin-4 antibody or antibody fragment thereof comprises a variable light chain sequence with at least about 95%, about 96%, about 97%, about 98%, or about 99% sequence identity to the anti-Nectin-4 light chain variable region sequence set forth in SEQ ID NOs: 2, 4, 6, 8, 10, 12, 14 or 16 comprises one or more conservative amino acid substitutions in a framework region (based on the numbering system of Kabat), and retains the binding and/or functional activity of an anti-Nectin-4 antibody or antibody fragment thereof that comprises a variable heavy chain sequence as set forth in SEQ ID NOs: 1, 3, 5, 7, 9, 11, 13 or 15 and a variable light chain sequence as set forth in SEQ ID NOs: 2, 4, 6, 8, 10, 12, 14 or 16.

Binding Characteristics

The disclosed antibodies (N4_mAb 1, N4_mAb 2, N4_mAb 3, N4_mAb 4, N4_mAb 5, N4_mAb 6, N4_mAb 7 and N4_mAb 8) and antibody fragments thereof specifically bind to human Nectin-4 as it occurs on the surface of normal or malignant cells, but do not specifically bind to the extracellular domain of human Nectin-1, Nectin-2 or Nectin-3.

Antibodies typically bind specifically to their cognate antigen with high affinity, reflected by a dissociation constant (KD) of $10^{-7}$ to $10^{-11}$ M or less. Any KD greater than about $10^{-6}$ M is generally considered to indicate nonspecific binding. As used herein, an antibody that "binds specifically" to an antigen refers to an antibody that binds to the antigen and substantially identical antigens with high affinity, which means having a KD of $10^{-7}$ M or less, preferably $10^{-8}$ M or less, even more preferably $5\times10^{-9}$ M or less, and most preferably between $10^{-8}$ M and $10^{-10}$ M or less, but does not bind with high affinity to an unrelated antigen. The disclosed antibodies bind to the human Nectin-4 ECD with high affinity, with KD determined by SPR ranging from $1.72\times10^{-8}$ M to $3.75\times10^{-10}$ M. N4_mAb 6, N_mAb 7 and N4_mAb 8 represent the group of highest affinity with KD less than $4\times10^{-10}$ M.

The term "cross-reacts," as used herein, refers to the ability of anti-human Nectin-4 specific antibody described herein to bind to Nectin-4 from a different species. For example, an antibody described herein may also bind Nectin-4 from another species (e.g., cynomolgus or rat, or mouse Nectin-4). As used herein, cross-reactivity may be measured by detecting a specific reactivity with purified antigen in binding assays (e.g., SPR, ELISA) or binding to, or otherwise functionally interacting with, cells physiologically expressing Nectin-4. Methods for determining cross-reactivity include standard binding assays as described herein, for example, by BIACORE® surface plasmon resonance (SPR) analysis using a BIACORE® 2000 SPR instrument (Biacore AB, Uppsala, Sweden), or flow cytometric techniques.

The disclosed human Nectin-4 antibodies, N4_mAb 1 to N4_mAb 8, all bind to Nectin-4 from cynomolgus monkey with notable affinity. Their binding affinity to rat Nectin-4 varies, with N4_mAb 5, N4_mAb 6, N4_mAb 7, and N4_mAb 8 among the strongest. They show weak or no binding to mouse Nectin-4.

Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antibody fragments thereof.

Antibodies may be prepared as chimeric antibodies or antibody fragments thereof with murine variable regions and human constant regions. The heavy chain constant region uses a consensus human IgG1 constant region sequence (Uniprot P01857), whereas the light chain constant region uses a consensus human Kappa constant region sequence (UniProt P01834). Human IgG1 may be chosen because it is one of the most common subtype for chimera antibody generation and can provide effector function. Human Kappa constant region may be used because all parental murine antibodies are of mouse Kappa light chain.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody binding specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., Methods 36:43-60 (2005)(describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. J. Immunol., 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

Nectin-4 Internalization and Dose Dependent Cytotoxicity

The disclosed antibodies specific for Nectin-4 are capable of mediating the internalization, including inducible internalization, of Nectin-4, which lead to dose-dependent cytotoxicity when an ADC-conjugated secondary antibody is present. In a CHO cell line overexpressing Nectin-4, the observed EC50 for cell killing ranges from 0.21 nM to 0.63 nM, In the cancer cell line SKBR3, the EC50 for cell killing ranges from 0.61 nM to 2.14 nM.

Antibody-Based Immunotherapy

The goal of antibody-based immunotherapy using tumor-antigen-targeting antibodies is to eliminate cancer cells without harming normal tissue. Therefore, the efficacy and safety of antibody-based immunotherapies in oncology varies depending in large part on the intended mechanism of action, the relevant effector function of the immune system and the nature of the tumor-specific or tumor-associated target antigen.

Antibody-drug conjugates (ADCs) are a class of highly potent antibody-based cancer therapeutics. ADCs consist of recombinant monoclonal antibodies covalently linked to cytotoxic agents (known as payloads) via synthetic linkers. ADCs combine the specificity of monoclonal antibodies and the potency of small-molecule chemotherapy drugs and facilitate the targeted delivery of highly cytotoxic small molecule drug moieties directly to tumor cells. The targeted nature of ADCs allows for increased drug potency coupled with limited systemic exposure. Together, these features provide ADCs with the desirable characteristics of having fewer side effects and a wider therapeutic window (Peters et al., *Biosci Rep,* 35(4):e00225, 2015).

Generally, once an ADC binds an antigen on the cancer cell surface, it is internalized and sent along the endosome/lysosome pathway for degradation. In the lysosome the payload is released either through specific cleavage of the linker by lysosome enzymes or general degradation of the antibody. The released cytotoxic compound then leaves the lysosome, accumulates to a requisite threshold level and ultimately causes death of the targeted cancer cell. An ideal ADC is one that retains the selectivity and killing capacity of a mAb while still being able to release the cytotoxic drug in quantities large enough to kill tumor cells.

Cell surface antigens suitable for use as ADC targets are characterized by two important properties: (i) high expression level by the target cell and limited or no expression in normal tissue and (ii) internalization (e.g., efficient internalization) in response to antibody binding. Nectin-4 is over-expressed in multiple cancers, particularly bladder, lung, pancreatic, head & neck, esophageal, breast and ovarian cancer (Challita-Eid et al., *Cancer Res,* 76(10):3003-13, 2016, Fabre-Lafay et al., *BMC Cancer,* 7:73, 2007, Takano et al., *Cancer Res,* 69(16):6694-03, 2009, Derycke et al., *Am J Clin Pathol,* 5:835-845, 2010). It is also known that monoclonal antibodies specific for Nectin-4 are capable of mediating the inducible and efficient internalization of Nectin-4 (Doronina et al., *Nat Biotechnol,* 21:778-784, 2003, (M-Rabet et al., *Annals of Oncology,* 28(4):769-776, 2017, WO2012/047724, U.S. Pat. No. 8,637,642 WO2004/016799, U.S. Pat. No. 7,968,090, WO2017/042210. U.S. Pat. No. 10,675,048). Therefore, the disclosed anti-Nectin-4 antibodies (N4_mAb 1 through N4_mAb 8) are suitable for use as ADC-based targeting antibodies for the development of antibody-based immunotherapies for the treatment of cancer.

The generation of antibody-drug conjugates can be accomplished by any technique known to the skilled artisan using any suitable payload drug, synthetic linker and conjugation chemistry. Those skilled in the art will be aware of ADCs and will also be aware that the development of an ADC requires an evaluation of several factors including target antigen biology, specificity of the antibody, cytotoxicity and mechanism of action of the payload drug, the stability and cleavage of the linker, the sites of linker attachment, and the levels of ADC heterogeneity produced by the conjugation chemistry. Heterogeneity, with respect to the number of cytotoxic molecules attached per antibody can result in the production of a drug product containing non-potent species (no drug payload) and species with more than 4 drug moieties (high loading) per antibody that have the potential to be cleared more rapidly and contribute to toxicity. Further, the presence of non-potent species (antibodies with no cytoxic payload) can decrease potency by competing for binding to the ADC target antigen. Therefore, it is desirable to produce ADC drug products with homogenous mixtures of antibodies characterized by a consistent drug:antibody ratio (DAR).

A majority of the ADC candidates currently under clinical evaluation employ one of the three major classes of drugs as cytotoxic payloads, namely maytansinoids, auristatins, and PBD dimers; but other classes of payloads, such as calicheamicin (for gemtuzumab ozogamicin and inotuzumab ozogamicin), duocarmycin, exatecan or SN-38 are also used (Shim et al., *Biomolecules,* 10(3):360, 2020). Generally speaking the cytotoxic drugs act either as tubulin inhibitors (auristatins and maytansinoids) or as disruptors of DNA structure, including duocarmycin (DNA alkylation), calicheamicin (DNA double strand cleavage), camptothecin analogues (topoisomerase inhibitor) such as SN-38 and exatecan, or pyrrolobenzodiazepine (PBD) dimers (DNA strand crosslinking) (Shim et al.).

One of the key functions of the linker is to maintain ADC stability in the blood circulation, while allowing toxin release upon internalization by the target cells. Important parameters to be considered during for the identification of a suitable linker include the cleavability of the linker and the details of the conjugation chemistry (i.e., the position and nature of the linkage).

Broadly speaking linkers are classified into two broad categories: cleavable and non-cleavable. Cleavable linkers exploit the differences between normal physiologic conditions in the bloodstream and the intracellular conditions present in the cytoplasm of cancer cells (Peters et al., *Biosci Rep,* 35(4):e00225, 2015). Changes in the microenvironment after an ADC-antigen complex is internalized, triggers cleavage of the linker and releases the cytotoxic payload, effectively targeting toxicity to cancer cells expressing the target antigen. Broadly speaking there are three types of cleavable linkers: hydrazone, disulfide and peptide linkers. In contrast, non-cleavable linkers depend solely on the process of lysosomal degradation following ADC-antigen internalization. After internalization of the ADC-antigen complex protease enzymes within the lysosome degrade the protein structure of the antibody, leaving a single amino acid (typically a cysteine or a lysine) attached to the linker and the cytotoxic agent that is released into the cytoplasm as the active drug. It is well known that linker chemistry is an important determinant of the specificity, potency, activity and safety of ADCs.

One of skill in the art will recognize that there are many techniques for chemical modification of proteins suitable for use in the conjugation of the linker-payload to a TSA- or TAA-specific antibody. The same person will recognize that different methods of conjugation chemistry will afford different levels of control over the number and site of drug attachment and potentially impact the pharmacokinetics, toxicity and therapeutic window of the anti-Nectin-4 ADC that is produced. Antibody-drug conjugates can be prepared by binding the drug to an antibody in accordance with a conventional technique. Techniques for conjugating a therapeutic moiety to antibodies are well known to those of skill in the art, see. e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", *Immunol. Rev.,* 62: 119-58 (1982).

One of skill in the art will appreciate that in addition to conventional conjugation techniques (involving conjugation to surface exposed lysine or cysteine residues present in an antibody either as a consequence of the native amino acid sequence composition) there are numerous other methods of site-specific drug conjugation that can be used to prepare anti-Nectin-4 specific immunoconjugates.

Site-specific conjugation chemistry methods are intended to produce relatively homogenous ADC products without altering the binding affinity of the antibody. Generally speaking, three strategies are mainly used for site-specific conjugation on antibodies: use of engineered cysteines, incorporation of unnatural amino acids and enzymatic conjugations using reaction sites of antibodies that are designed to react specifically to a bacterials enzyme (e.g. transglutaminases, glycotransferases, sortases or formyl glycine generating enzyme) that generate post-translational modifications of proteins in a site-specific manner. Techniques for the site-specific conjugation a therapeutic moiety to antibodies are well known to those of skill in the art and include, but are not limited to the methods disclosed in U.S. Pat. Nos. 7,723,485; 8,937,161; 9,000,130; 9,884,127; 9,717,803; 10,639,291; 10,357,472 U.S. Patent Application Publication Nos: US 2015/0283259; US 2017/0362334; US 2018/0140714; and International Publication Nos.: WO 2013/092983; WO 2013/092998; WO 2014/072482; WO 2014/202773; WO 2014/202775; WO 2015/155753; WO 2015/191883; WO 2016/102632; WO 2017/059158; WO 2018/140590 and WO 2018/185526.

ADCs can be designed to kill not only target antigen positive cells but also other cells in the vicinity, irrespective of the expression of the target antigen on their surface by a mechanism commonly referred to as the "bystander effect" (Kovtun et al., *Cancer Res.* 66(6):3214-21, 2006). Although the bystander effect undermines the concept of the absolute target specificity of ADCs, it can be advantageous when treating solid tumors that lack homogenous expression of the target antigen. Enfortumab vedotin is known to exert a bystander effect by release of the cell permeable MMAE from Nectin-4-positive cells to kill Nectin-4-negative cancer cells in an admixed cellular assay (Liu et al. Abstract 5581, Poster presented at the American Association of Cancer Research Virtual Meeting II, 2020). Documentation of enfortumab vedotin's bystander effect supports future clinical studies of Nectin-4 directed ADC, alone or in combination with other checkpoint inhibitors, for the treatment of tumors characterized by heterogeneous expression of Nectin-4.

Enfortumab Vedotin

Enfortumab vedotin-ejfv (PADCEV®) is the first, and only FDA-approved Nectin-4-directed ADC. Enfortumab vedotin (AGS-22 M6E) consists of a fully human IgG1-kappa anti-Nectin-4 antibody (AGS-22C3), conjugated by a protease cleavable linker (maleimidocaproyl valine-citrulline) to the small molecule monomethyl auristatin E (MMAE, a microtubule-disrupting agent) (see, e.g., WO 2012/047724, U.S. Pat. Nos. 8,637,642, 9,078,931, 9,962,454). The ADC binds to the Nectin-4 expressed on the cell surface and the entire complex is internalized. MMAE is cleaved from the complex resulting in the disruption of the microtubule network within the cell, leading to cell cycle arrest and apoptotic cell death.

The parental antibody (AGS-22 M6) used to generate enfortumab was generated by immunizing a XENOMOUSE® strain (Amgen/Abgenix) with the extracellular domain (ECD) of human Nectin-4. AGS-22 M6 binds to transfected human, monkey and rat Nectin-4 expressed on the surface of human PC3 (prostate cancer) host cells (Challita-Eid et al., *Cancer Res,* 76(10):3003-13, 2016). AGS-22 M6 recognizes and epitope in the first Ig-like domain of Nectin-4 and blocks Nectin-4/Nectin-1 trans-interaction in vitro, but has not been reported to have any effect on cell viability (Challita-Eid et al.). Of note, the parental antibody does not mediate antitumor activity in any preclinical model, enfortumab vedotin efficacy is correlated with the bound cytotoxic payload and Nectin-4 expression.

Enfortumab vedotin was first approved by the United States Food and Drug Administration in December 2019 for usage in patients with locally advanced and metastatic urothelial cancer who have received prior treatment with an immune checkpoint inhibitor (i.e., programmed cell death protein 1 (PD-1)/programmed death-ligand 1 (PD-L1) therapy) and platinum-based chemotherapy either as neoadjuvant or as adjuvant treatment in the locally advanced and metastatic settings. Urothelial cancer, accounting for more than 90% of bladder cancers, begins in cells that line the bladder and nearby organs. Platinum-containing chemotherapy, PD-1 and PD-L1 inhibitors are standard treatments for patients with bladder cancer, the sixth most common cancer in the U.S.

Published reports indicate that subsequent to the binding of enfortumab vedotin to cancer cells expressing Nectin-4 (i.e., bladder carcinoma cell line T24-Nectin-4), the enfortumab vedotin/Nectin-4 complex is internalized and catabolized in the intracellular lysosomal compartment (Doronina et al., *Nat Biotechnol,* 21:778-784, 2003). The resulting intracellular release of MMAE into the cytosol is known to induce growth arrest in G2/M phase followed by apoptotic cell death (Francisco, J A et al, *Blood,* 102:1458 2003). As expected, higher levels of cytotoxic cell killing correlated with higher levels of release of intracellular MMAE. No cytotoxicity activity was reported for the unconjugated parental antibody (AGS-22 M6) used to prepare the ADC.

During its nonclinical development enfortumab vedotin demonstrated antitumor activity in Nectin-4 expressing cell lines and animal models. Enfortumab vedotin inhibits the growth of Nectin-4 expressing tumors in mouse xenograft models of human bladder, pancreatic, breast and lung cancer. Enfortumab vedotin treatment significantly inhibited the growth of all four tumor types, and resulted in tumor regression of bladder and breast xenografts (Challita-Eid et al., *Cancer Res,* 76(10):3003-13, 2016). The effects of Enfortumab vedotin ADC-based immunotherapy in a bladder cancer xenograft model (T-24 cells implanted in nude mice) has been reported to extended beyond targeted auristatin delivery, cell cycle arrest, and apoptosis to include bystander cell killing, immunogenic cell death (ICD) including the extracellular release of adenosine triphosphate and HMGB1, immune cell recruitment and activation of antigen presenting cells (Liu et al., Abstract 5581, Poster presented at the American Association of Cancer Research Virtual Meeting II, 2020).

The FDA granted an accelerated approval of enfortumab vedotin based on response rate and durability of response observed in the multicenter phase II EV-201 trial ((ClinicalTrials.gov identifier NCT03219333). The EV-201 trial enrolled 125 patients with locally advanced or metastatic urothelial cancer who received prior treatment with PD-1 or PD-L1 inhibitor and platinum-based chemotherapy. Patients received enfortumab vedotin-ejfv at 1.25 mg/kg on days 1, 8, and 15 of 28-day cycles until disease progression or unacceptable toxicity. The overall response rate, reflecting the percentage of patients who had a certain amount of tumor shrinkage, was 44%, with 12% having a complete response and 32% having a partial response. The median duration of response was 7.6 months (Rosenberg et al., J Clin Oncol, 37(29):2592-2600, 2019).

The EV-201 study is also rolled a second cohort (Cohort 2) of patients who have received prior anti-PD-1/L1 therapy and are cisplatin ineligible without prior platinum treatment to determine if a similar benefit will be observed. Enfortumab vedotin is also being evaluated in other solid tumors in the phase 2 EV-202 trial (ClinicalTrials.gov identifier NCT04225117), including hormone receptor-positive/HER-negative breast cancer, triple-negative breast cancer, non-squamous non-small cell lung cancer, head and neck cancer, and gastric and esophageal cancer.

In addition, a phase 111 trial (EV-301; ClinicalTrials.gov identifier NCT03474107). comparing enfortumab vedotin monotherapy with single-agent chemotherapy in patients with prior platinum and anti-PD-1/L1 therapy could establish the survival benefit of enfortumab vedotin in this patient population. Enfortumab vedotin is also being evaluated in a broader population of patients with urothelial carcinoma, including in the first-line setting where it is being studied in a Phase I/II trial in combination with anti-PD-1 and/or platinum-based therapies (EV-103; ClinicalTrials.gov identifier: NCT03288545).

Methods of Producing Antibodies

Anti-Nectin-4 antibodies or antibody fragments thereof may be made by any method known in the art. For example, a recipient may be immunized with soluble recombinant Nectin-4 (N4) protein or a fragment of a N4 peptide conjugated with a carrier protein thereof. Any suitable method of immunization can be used. Such methods can include adjuvants, other immune stimulants, repeat booster immunizations, and the use of one or more immunization routes.

Any suitable source of human Nectin-4 can be used as the immunogen for the generation of the non-human or human anti-Nectin-4 antibodies of the compositions and methods disclosed herein.

Different forms of a Nectin-4 antigens may be used to elicit an immune response for the identification of a biologically active anti-Nectin-4 antibody. Thus, the eliciting Nectin-4 antigen may be a single epitope, multiple epitopes, or the entire protein alone or in combination with one or more immunogenicity enhancing agents. In some aspects, the eliciting antigen is an isolated soluble full-length protein, or a soluble protein comprising less than the full-length sequence (e.g., immunizing with a peptide comprising the V-like domain of human Nectin-4 or one or both of the C-like domains of human Nectin-4). As used herein, the term "portion" refers to the minimal number of amino acids or nucleic acids, as appropriate, to constitute an immunogenic epitope of the antigen of interest. Any genetic vectors suitable for transformation of the cells of interest may be employed, including, but not limited to adenoviral vectors, plasmids, and non-viral vectors, such as cationic lipids.

It is desirable to prepare monoclonal antibodies (mAbs) from various mammalian hosts, such as mice, rodents, primates, humans, etc. Description of techniques for preparing such monoclonal antibodies may be found in, e.g., Sties et al. (eds.) BASIC AND CLINICAL IMMUNOLOGY ($4^{th}$ ed.) Lance Medical Publication, Los Altos, CA, and references cited therein; Harlow and Lane (1988) ANTIBODIES: A LABORATORY MANUAL CSH Press; Goding (1986) MONOCLONAL ANTIBODIES: PRINCIPLES AND PRACTICE ($2^{nd}$ ed.) Academic Press, New York, NY. Typically, spleen cells from an animal immunized with a desired antigen are immortalized, commonly by fusion with a myeloma cell. See Kohler and Milstein (196) *Eur. J. Immunol.* 6:511-519. Alternative methods of immortalization include transformation with Epstein Barr Virus, oncogene, or retroviruses, or other methods known in the art. See. e.g., Doyle et al. (eds. 1994 and periodic supplements) CELL AND TISSUE CULTURE: LABORATORY PROCEDURES, John Wiley and Sons, New York, NY. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or an antigen binding fragment thereof by screening a DNA library from human B cells according, e.g., to the general protocol outlined by Huse et al. (1989) Science 246: 1275-1281. Thus, antibodies may be obtained by a variety of techniques familiar to researchers skilled in the art.

Other suitable techniques involve selection of libraries of antibodies in phage, yeast, virus or similar vector. See e.g., Huse et al. supra; and Ward et al. (1989) *Nature* 341:544-546. The polypeptides and antibodies disclosed herein may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literatures. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,9396,345; 4,277,437; 4,275,149; and 4,366,241. Also, recombinant immunoglobulins may be produced, see Cabilly U.S. Pat. No. 4,816,567; and Queen et al. (1989) *Proc. Nat'l Acad. Sci. USA* 86: 10029-10023; or made in transgenic mice, see Nils Lonberg et al. (1994), *Nature* 368:856-859; and Mendez et al. (1997) *Nature Genetics* 15: 146-156; TRANSGENIC ANIMALS AND METHODS OF USE (WO 2012/62118), Medarex, Trianni, Abgenix, Ablexis, OminiAb, Harbour and other technologies.

In some embodiments, the ability of the produced antibody to bind to Nectin-4 and/or other related members of the nectin family can be assessed using standard binding assays, such as surface plasmon resonance (SPR), Fortebio (BLI), ELISA, Western Blot, Immunofluorescent, flow cytometric analysis, chemotaxis assays, and cell migration assays. In some aspects, the produced antibody may also be assessed for its ability to block/inhibit Nectin-4 from binding to Nectin-1 or TIGIT, or to be efficiently internalized upon Nectin-4 binding to Nectin-4 expressing cells.

The antibody composition prepared from the hybridoma or host cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.54.5, typically performed at low salt concentrations (e.g., from about 0-0.25 M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an antibody or antibody fragment of the present disclosure. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-Nectin-4 polypeptide (e.g., a heavy chain or light chain variable region), or its complement. Hybridizing nucleic acids of the type described herein can be used, for example, as a cloning probe, a primer, e.g., a PCR primer, or a diagnostic probe.

Polynucleotides, Vectors, and Host Cells

Other embodiments encompass isolated polynucleotides that comprise a sequence encoding an anti-Nectin-4 antibody or antibody fragment thereof, vectors, and host cells comprising the polynucleotides, and recombinant techniques for production of the antibody. The isolated polynucleotides can encode any desired form of the anti-Nectin-4 antibody including, for example, full length monoclonal antibodies, Fab, Fab', $F(ab')_2$, and Fv fragments, diabodies, linear antibodies, single-chain antibody molecules, chimeric, humanized, bispecific, and multispecific antibodies formed from antibody fragments.

Some embodiments include isolated polynucleotides comprising sequences that encode the heavy chain variable region of an antibody or antibody fragment having the amino acid sequence of SEQ ID NOs: 1, 3, 5, 7, 9, 11, 13, or 15. Some embodiments include isolated polynucleotides comprising sequences that encode the light chain variable region of an antibody or antibody fragment having the amino acid sequence of any of SEQ ID NOs: 2, 4, 6, 8, 10, 12, 14 or 16.

In an embodiment, the isolated polynucleotide sequence (s) encodes an antibody or antibody fragment having a light chain variable region and a heavy chain variable region comprising the amino acid sequences of:

(a) a variable heavy chain sequence comprising SEQ ID NO: 1 and a variable light chain sequence comprising SEQ ID NO: 2.

(b) a variable heavy chain sequence comprising SEQ ID NO: 3 and a variable light chain sequence comprising SEQ ID NO: 4;

(c) a variable heavy chain sequence comprising SEQ ID NO: 5 and a variable light chain sequence comprising SEQ ID NO: 6;

(d) a variable heavy chain sequence comprising SEQ ID NO: 7 and a variable light chain sequence comprising SEQ ID NO: 8;

(e) a variable heavy chain sequence comprising SEQ ID NO: 9 and a variable light chain sequence comprising SEQ ID NO: 10;

(f) a variable heavy chain sequence comprising SEQ ID NO: 11 and a variable light chain sequence comprising SEQ ID NO: 12;

(g) a variable heavy chain sequence comprising SEQ ID NO: 13 and a variable light chain sequence comprising SEQ ID NO: 14; or (h) a variable heavy chain sequence comprising SEQ ID NO: 15 and a variable light chain sequence comprising SEQ ID NO: 16.

In another embodiment, the isolated polynucleotide sequence(s) encodes an antibody or antibody fragment having a light chain variable region and a heavy chain variable region comprising the amino acid sequences of:

(a) a variable heavy chain sequence that is 90%, 95%, or 99% identical to SEQ ID NO: 1 and a variable light chain sequence that is 90%, 95%, or 99% identical to SEQ ID NO: 2;

(b) a variable heavy chain sequence that is 90%, 95%, or 99% identical to SEQ ID NO: 3 and a variable light chain sequence that is 90%, 95%, or 99% identical to SEQ ID NO: 4;

(c) a variable heavy chain sequence that is 90%, 95%, or 99% identical to SEQ ID NO: 5 and a variable light chain sequence that is 90%, 95%, or 99% identical to SEQ ID NO: 6;

(d) a variable heavy chain sequence that is 90%, 95%, or 99% identical to SEQ ID NO: 7 and a variable light chain sequence that is 90%, 95%, or 99% identical to SEQ ID NO: 8;

(e) a variable heavy chain sequence that is 90%, 95%, or 99% identical to SEQ ID NO: 9 and a variable light chain sequence that is 90%, 95%, or 99% identical to SEQ ID NO: 10;

(f) a variable heavy chain sequence that is 90%, 95%, or 99% identical to SEQ ID NO: 11 and a variable light chain sequence that is 90%, 95%, or 99% identical to SEQ ID NO: 12;

(g) a variable heavy chain sequence that is 90%, 95%, or 99% identical to SEQ ID NO: 13 and a variable light chain sequence that is 90%, 95%, or 99% identical to SEQ ID NO: 14; or (h) a variable heavy chain sequence that is 90%, 95%, or 99% identical to SEQ ID NO: 15 and a variable light chain sequence that is 90%, 95%, or 99% identical to SEQ ID NO: 16.

The polynucleotide(s) that comprise a sequence encoding an anti-Nectin-4 antibody or antibody fragment thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-Nectin-4 antibodies or antibody fragments thereof can also be produced as fusion polypeptides, in which the antibody or fragment is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the anti-Nectin-4 antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the anti-Nectin-4 antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

Antibody Compositions and Methods of Treatment

The disclosure also provides compositions including, for example, pharmaceutical compositions that comprise an anti-Nectin-4 antibody or antibody fragment thereof for use in the treatment of patients having a cancer including, for example, epithelial cell-derived primary or metastatic cancer. In a particular embodiment, the compositions described herein are administered to cancer patients to kill tumor cells. For example, the compositions described herein can be used to treat a patient with a solid tumor characterized by the presence of cancer cells expressing or overexpressing Nectin-4. In some aspects, the disclosed compositions can be used to treat breast, lung, ovarian, pancreatic, gastric, gallbladder or urothelial cancer.

In some aspects, the treatment of cancer represents a field where combination strategies are especially desirable since frequently the combined action of two, three, four or even more cancer drugs/therapies generates synergistic effects which are considerably stronger than the impact of a monotherapeutic approach. The agents and compositions (e.g., pharmaceutical compositions) provided herein may be used alone or in combination with conventional therapeutic regimens such as surgery, irradiation, chemotherapy and/or bone marrow transplantation (autologous, syngeneic, allogeneic or unrelated). The agents and compositions may also be used in combination with one or more of an antineoplastic agent, a chemotherapeutic agent, a growth inhibitory agent, a cytotoxic agent, an immune checkpoint inhibitor, costimulatory molecule, kinase inhibitors, angiogenesis inhibitors, small molecule targeted therapy drugs, and multi-epitope strategies. Thus, in another embodiment of the present disclosure, a cancer treatment may be effectively combined with various other drugs.

In one treatment method, pharmaceutical compositions comprising the anti-Nectin-4 antibody can further comprise a therapeutic or toxic agent, either conjugated or unconjugated to the anti-Nectin-4 antibody or antibody fragment. In a particular embodiment, an anti-Nectin-4 antibody is used to target an ADC with a cytotoxic payload to tumors expressing and/or overexpressing Nectin-4.

The disclosed Nectin-4 antibodies can be administered either alone or in combination with other compositions that are useful for treating cancer. In one embodiment, the disclosed antibodies can be administered either alone or in combination with other immunotherapeutics including other antibodies useful for treating cancer. For example, in an embodiment the other immunotherapeutic is an antibody against an immune checkpoint molecule selected from the group consisting of human programmed cell death protein 1 (PD-1), PD-L1 and PD-L2, lymphocyte activation gene 3 (LAG3), NKG2A, B7-H3, B7-H4, CTLA-4, GITR, VISTA, CD137, TIGIT and any combination thereof. In an alternative embodiment the second immunotherapeutic is an antibody to a tumor specific antigen (TSA) or a tumor associated antigen (TAA). Each combination representing a separate embodiment of the disclosure.

The combination of therapeutic agents discussed herein can be administered concurrently as components of a bispecific or multi-specific binding agent or fusion protein or as a single composition in a pharmaceutically acceptable carrier. Alternatively, a combination of therapeutics can be administered concurrently as separate compositions with each agent in a pharmaceutically acceptable carrier. In another embodiment, the combination of therapeutic agents can be administered sequentially.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995. In some aspects, the pharmaceutical composition is administered to a subject to treat cancer.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of the active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

A composition of the present disclosure can be administered by a variety of methods known in the art. As will be appreciated by the skilled artisan, the route and/or mode of administration will vary depending upon the desired results. The active compounds can be prepared with carriers that will protect the compound against rapid releases, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

In an alternative embodiment, conventional viral and non-viral based gene transfer methods can be used to introduce nucleic acids encoding the antibodies or derivatives thereof, as described herein, in mammalian cells or target tissues. Such methods can be used to administer nucleic acids encoding the antibodies to cells in vitro. In some embodiments, the nucleic acids encoding the antibodies or derivatives thereof are administered for in vivo or ex vivo gene therapy uses. In other embodiments, gene delivery techniques are used to study the activity of the antibodies in cell-based or animal models. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Such methods are well known in the art.

Methods of non-viral delivery of nucleic acids encoding engineered polypeptides of the disclosure include lipofection, microinjection, biolistics, virosomes, liposomes, immunoliposomes, polycation or lipid: nucleic acid conjugates, naked DNA, artificial virions, and agent-enhanced uptake of DNA. Lipofection methods and lipofection reagents are well known in the art (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). The preparation of lipid: nucleic acid complexes, including targeted liposomes such as immunolipid complexes, is well known to one of skill in the art.

The use of RNA or DNA viral based systems for the delivery of nucleic acids encoding the antibodies described herein take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the disclosure could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

Dosage levels of the active ingredients in the pharmaceutical compositions may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical compositions described herein may be administered in effective amounts. An "effective amount" refers to the amount which achieves a desired reaction or the desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease.

Non-Therapeutic Uses

Both soluble (sN4) and transmembrane Nectin-4 isoforms have been described in rodents and humans (Reymond et al., *J Biol Chem,* 276(46):43205-15, 2001). Soluble Nectin-4 is produced by proteolytic cleavage at the cell surface by the metalloproteinases ADAM17/TACE Soluble N4 (Fabre-Lafay et al., *J Biol Chem,* 289(20):19543-19550, 2005), and ADAM10 (Buchanan et al., *J Biol Chem,* 292(15):6339-6351, 2017) and can be detected in the serum of breast, ovarian and lung cancer patients (Buchanan et al. Fabre-Lafay et al., *BMC Cancer,* 7:73, 2007, Takano et al., *Cancer Res.* 69(16):6694-03, 2009).

Several clinical investigations have revealed that Nectin-4 can serve as a tumor biomarker, and its over-expression in cancer tissues is significantly associated with cancer progression and poor survival of the patients (Fabre-Lafay et al., *BMC Cancer,* 7:73, 2007, Siddharth et al., *Int J Biochem Cell Biol,* 102:151-160, 2018, Nishiwada et al., *J Exp Clin Cancer Res,* 34(1):30, 2015, Zhang et al., *Oncology Lett* 18:1163-1170, 2019, Derycke et al., *Am J Clin Pathol,* 5:835-845, 2010, Deng et al., *Cancer Cell Int,* 19:106, 2019).

The abnormal expressions of both membranous and soluble forms of Nectin-4 have been reported in human breast cancer tissues and their sera (Fabre-Lafay et al., *BMC Cancer.* 7:73, 2007) and Nectin-4 has been proposed as a useful histological and serological tumor associated marker and as a prognostic predictor for breast cancer patients (Fabre-Lafay et al., *BMC Cancer.* 7:73, 2007, M-Rabet et al., *Annals of Oncology,* 28(4):769-776, 2017, Siddharth et al., *Int J Biochem Cell Biol,* 102:151-160, 2018). In human pancreatic carcinoma, the over-expression of Nectin-4 significantly promotes the proliferation of cancer cells and contributes to the intra-tumoral angiogenesis (Nishiwada et al., *J Exp Clin Cancer Res,* 34(1):30, 2015). It has been demonstrated that higher Nectin-4 expression is found in human gastric cancer tissues compared with the normal gastric tissues, and the expression level of Nectin-4 is significantly associated with cancer cell differentiation, lymph node metastasis, advanced TNM stage and poorer prognosis of the patients (Zhang et al., *Hum Pathol,* 72:107-116, 2018). Nectin-4 has also been reported to be overexpressed in esophageal and colorectal cancer (Deng et al., *Cancer Cell Int,* 19:106, 2019, Zhang et al., *Oncology Lett* 18:1163-1170, 2019).

Detection of Nectin-4 may be a useful prognostic predictor of tumor progression. Such methods include contacting a biological sample from a subject with an anti-Nectin-4 antibody or antibody fragment thereof and detecting binding of the antibody Nectin-4. By "biological sample" is intended any biological sample obtained from an individual, cell line, tissue culture, or other source of cells potentially expressing Nectin-4. Methods for obtaining tissue biopsies for immunohistochemical analysis and body fluids for detection of soluble proteins in the serum or plasma of human subjects are well known in the art.

Anti-Nectin-4 antibodies or antibody fragments are also useful in diagnostic assays to detect and/or quantify Nectin-4 protein, for example, detecting Nectin-4 expression in specific cells, tissues, or serum. The anti-Nectin-4 antibodies can be used diagnostically to, for example, monitor the development or progression of a disease as part of a clinical testing procedure to, e.g., determine the efficacy of a given treatment and/or prevention regimen.

It will be advantageous in some embodiments, for example, for diagnostic purposes to label the antibody with a detectable moiety. Numerous detectable labels are available, including radioisotopes, fluorescent labels, enzyme substrate labels and the like. The label may be indirectly conjugated with the antibody using various known techniques. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody can be conjugated with a small hapten (such as digoxin) and one of the different types of labels mentioned above is conjugated with an anti-hapten antibody (e.g., anti-digoxin antibody). Thus, indirect conjugation of the label with the antibody can be achieved.

Exemplary radioisotopes labels include 35S, 14C, 125I, 3H, and 131I. The antibody can be labeled with the radioisotope, using the techniques described in, for example, Current Protocols in Immunology, Volumes 1 and 2, 1991, Coligen et al., Ed. Wiley-Interscience, New York, N.Y., Pubs. Radioactivity can be measured, for example, by scintillation counting.

Exemplary fluorescent labels include labels derived from rare earth chelates (europium chelates) or fluorescein and its derivatives, rhodamine and its derivatives, dansyl, Lissamine, phycoerythrin, and Texas Red are available. The fluorescent labels can be conjugated to the antibody via known techniques, such as those disclosed in Current Protocols in Immunology, for example. Fluorescence can be quantified using a fluorimeter. There are various well-characterized enzyme-substrate labels known in the art (see, e.g., U.S. Pat. No. 4,275,149). The enzyme generally catalyzes a chemical alteration of the chromogenic substrate that can be measured using various techniques. For example, alteration may be a color change in a substrate that can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured, using a chemiluminometer, for example, or donates energy to a fluorescent acceptor.

Examples of enzymatic labels include luciferases such as firefly luciferase and bacterial luciferase (U.S. Pat. No. 4,737,456), luciferin, 2,3-dihydrophthalazinediones, malate dehydrogenase, urease, peroxidase such as horseradish peroxidase (HRPO), alkaline phosphatase, D-galactosidase, glucoamylase, lysozyme, saccharide oxidases (such as glucose oxidase, galactose oxidase, and glucose-6-phosphate dehydrogenase), heterocylic oxidases (such as uricase and xanthine oxidase), lactoperoxidase, microperoxidase, and the like. Techniques for conjugating enzymes to antibodies are described, for example, in O'Sullivan et al., 1981, Methods for the Preparation of Enzyme-Antibody Conjugates for use in Enzyme Immunoassay, in Methods in Enzym. (J. Langone & H. Van Vunakis, eds.), Academic press, N.Y., 73: 147-166.

Examples of enzyme-substrate combinations include, for example: Horseradish peroxidase (HRPO) with hydrogen peroxidase as a substrate, wherein the hydrogen peroxidase oxidizes a dye precursor such as orthophenylene diamine (OPD) or 3,3',5,5'-tetramethyl benzidine hydrochloride (TMB): alkaline phosphatase (AP) with para-Nitrophenyl phosphate as chromogenic substrate; and β-D-galactosidase (β-D-Gal) with a chromogenic substrate such as p-nitrophenyl-β-D-galactosidase or fluorogenic substrate 4-methylumbelliferyl-β-D-galactosidase.

In another embodiment, the anti-Nectin-4 antibody or antibody fragment thereof is used unlabeled and detected with a labeled antibody that binds the anti-Nectin-4 antibody or antibody fragment thereof.

The antibodies and antibody fragments thereof described herein may be employed in any known assay method, such as competitive binding assays, direct and indirect sandwich assays, and immunoprecipitation assays. See, e.g., Zola, Monoclonal Antibodies: A Manual of Techniques, pp. 147-158 (CRC Press, Inc. 1987).

All patents and publications identified are expressly incorporated herein by reference for the purpose of describing and disclosing, for example, the methodologies described in such publications that might be used in connection with the disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The broad scope of this disclosure is best understood with reference to the following examples, which are not intended to limit the disclosures to the specific embodiments. The specific embodiments described herein are offered by way of example only, and the disclosure is to be limited by the terms of the appended claims, along with the full scope of the equivalents to which such claims are entitled.

EXAMPLES

General Methods

Methods for protein purification including immunoprecipitation, chromatography, and electrophoresis are described. See, e.g., Coligan et al. (2000) Current Protocols in Protein Science, Vol. 1, John Wiley and Sons, Inc., New York. Chemical analysis, chemical modification, post-translational modification, production of fusion proteins, and glycosylation of proteins are described. See, e.g., Coligan et al. (2000) Current Protocols in Protein Science, Vol. 2, John Wiley and Sons, Inc., New York; Ausubel et al. (2001) Current Protocols in Molecular Biology, Vol. 3, John Wiley and Sons, Inc., NY, N.Y., pp. 16.0.5-16.22.17; Sigma-Aldrich, Co. (2001) Products for Life Science Research, St. Louis, Mo.: pp. 45-89; Amersham Pharmacia Biotech (2001) BioDirectory, Piscataway, N.J., pp. 384-391. Production, purification, and fragmentation of polyclonal and monoclonal antibodies are described. Coligan et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra.

Hybridoma or cell culture supernatant containing an anti-Nectin-4 antibody was purified via HiTrap protein G column (GE, cat. No. 17040401) according to the manufacturer's procedures. Briefly, supernatant was equilibrated with DPBS (Gibco, cat. No. 14190-136) for 5 CV and loaded via syringe/infusion pump (Legato 200, KDS) at ambient temperature and 3 minute residence time. The column was washed with 5 CV of DPBS and elution was performed with 4 CV of pH 2.8 elution buffer (Fisher Scientific, cat. No. P121004). Elution was fractionated, and fractions were neutralized with 1 M Tris-HCL, pH 8.5 (Fisher Scientific, cat No. 50-843-270) and assayed by A280 (DropSense96, Trinean). Peak fractions were pooled, and buffer exchanged into DPBS. Centrifugal filters (EMD Millipore, cat. No. UFC803024) were equilibrated in DPBS at 4,000×g for 2 mins. Purified sample was loaded, DPBS was added and the sample was spun at 4,000×g for 5-10 minute spins until total DPBS volume reached ≥6 DV. The final pool was analyzed by A280.

Standard methods in molecular biology are described. See, e.g., Maniatis et al. (1982) Molecular Cloning, A Laboratory Manual, Cold Spring Harbor Laboratory Press, Cold Spring Harbor, N.Y.; Sambrook and Russell (2001) Molecular Cloning, 3rd ed., Cold Spring Harbor Laboratory Press, Cold Spring Harbor, N.Y.; Wu (1993) Recombinant DNA, Vol. 217, Academic Press, San Diego, Calif. Standard methods also appear in Ausbel et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Stable cell lines expressing human Nectin-4 were generated by transfecting a selected host cell (i.e., CHO-K1) with pcDNA3.1-based plasmids expressing *Homo sapiens* Nectin-4 (NCBI accession number NM_030916.2) using electroporation-based transfection. Geneticin was used to select the integrated cells. After 7-10 days of geneticin selection, stable clones were isolated by FACS using a PE-conjugated anti-Nectin-4 antibody (R & D Systems, cat #FAB2659P). After expansion, the stable clones were further confirmed for Nectin-4 expression by flow cytometry.

The sequences for the heavy and light chain variable regions for hybridoma clones were determined as described below. Total RNA was extracted from 1-2×$10^6$ hybridoma cells using the RNeasy Plus Mini Kit from Qiagen (Germantown, MD, USA). CDNA was generated by performing 5' RACE reactions using the SMARTer RACE 5'/3' Kit from Takara (Mountainview, CA, USA). PCR was performed using the Q5 High-Fidelity DNA Polymerase from NEB (Ipswich, MA, USA) to amplify the variable regions from the heavy and light chains using the Takara Universal Primer Mix in combination with gene specific primers for the 3' mouse constant region of the appropriate immunoglobulin. The amplified variable regions for the heavy and light chains were run on 2% agarose gels, the appropriate bands excised and then gel purified using the Mini Elute Gel Extraction Kit from Qiagen. The purified PCR products were cloned using the Zero Blunt PCR Cloning Kit from Invitrogen (Carlsbad, CA, USA), transformed into Stellar Competent *E. Coli* cells from Takara and plated onto LB Agar+50 ug/ml kanamycin plates. Direct colony Sanger sequencing was performed by GeneWiz (South Plainfield, NJ, USA). The resulting nucleotide sequences were analyzed using IMGT V-QUEST to identify productive rearrangements and analyze translated protein sequences. CDR determination was based on Kabat numbering.

Selected VH or VL chains were PCR amplified and cloned into a pcDNA3.4-based expression vector, which harbors the constant region from human IgG1 (Uniprot P01857) or human Kappa light chain (UniProt P01834). Paired heavy chain- and light chain-expressing plasmids were transfected into Expi293 cells (Thermo Fisher Scientific) following provider's Expi293 expression system protocol. Five days after transfection culture supernatants were collected by centrifugation. Chimera antibodies were purified by 1-step affinity purification using Protein A column and buffer exchanged to PBS pH 7.2.

Methods for flow cytometry, including fluorescence activated cell sorting detection systems (FACS®), are available. See, e.g., Owens et al. (1994) Flow Cytometry Principles for Clinical Laboratory Practice, John Wiley and Sons, Hoboken, N.J.; Givan (2001) Flow Cytometry, 2nd ed.; Wiley-Liss, Hoboken, N.J.; Shapiro (2003) Practical Flow Cytometry, John Wiley and Sons, Hoboken. N.J. Fluorescent reagents suitable for modifying nucleic acids, including nucleic acid primers and probes, polypeptides, and antibodies, for use, e.g., as diagnostic reagents, are available. Molecular Probes (2003) Catalogue, Molecular Probes, Inc., Eugene, Oreg.; Sigma-Aldrich (2003) Catalogue, St. Louis, Mo.

Standard techniques for characterizing ligand/receptor interactions are available. See, e.g., Coligan et al. (2001) Current Protocols in Immunology, Vol. 4, John Wiley. Inc., New York. Standard methods of antibody functional characterization appropriate for the characterization of antibodies with particular mechanisms of action are also well known to those of skill in the art.

An in-house Nectin-4-specific antibody based on the fully human anti-Nectin-4 antibody Enfortumab (AGS-22 M6), referred to herein as "Positive Control 1" (PC1), was prepared based on the publicly available information published in WO 2012/047724 (VH, SEQ ID NO: 7; and VL, SEQ ID NO: 8). The PC1 antibody was used to confirm Nectin-4 expression by the transfectant and tumor cell lines used in the examples and to establish the binding and functional assays used to evaluate and characterize the anti-Nectin-4 specific antibodies disclosed herein. A second in-house Nectin-4 antibody, referred to herein as "Positive Control 2" (PC2), was prepared based on publicly available information published in WO 2019/215728 (VH, SEQ ID NO: 37; and VL, SEQ ID NO: 38). PC2 antibody was used as a control in the assay of blocking interaction between TIGIT and Nectin-4.

Software packages and databases for determining, e.g., antigenic fragments, leader sequences, protein folding, functional domains, CDR annotation, glycosylation sites, and sequence alignments, are available.

Example 1: Generation of Anti-Nectin-4 Antibodies

Mouse anti-Nectin-4 antibodies were generated by immunizing Balb/c mice with recombinant human Nectin-4 protein.

Immunization: Balb/c mice were immunized with recombinant human Nectin-4 protein either intraperitoneally (IP) and subcutaneously (SC). The immune response was monitored by retroorbital bleeds. The plasma was screened by ELISA, flow cytometry (FACS) or Imaging (as described below), and mice with sufficient titers of anti-Nectin-4 were used for fusions. Mice were boosted intraperitoneally or intravenously with the immunogen before sacrifice and removal of the spleen and lymph nodes.

Selection of mice producing anti-Nectin-4 Antibodies: to select mice producing antibodies that bound Nectin-4, sera from immunized mice was screened by ELISA, FACS or imaging for binding to recombinant Nectin-4 protein or cell line expressing Nectin-4 (CHO-Nectin-4) or endogenous cell line expressing Nectin-4 (T-47D, purchased from ATCC) and not to parental CHO cell line that does not express Nectin-4. For ELISA, briefly, an ELISA plate coated with recombinant human Nectin-4 was incubated with dilutions of serum from immunized mice for one hour at room temperature, the assay plate was washed, and specific antibody binding was detected with HRP-labeled anti-mouse IgG antibody. Plates was read using an ELISA reader (Biotek). For FACS, briefly, CHO-Nectin-4 cells or parental CHO cells or endogenous cells expressing Nectin-4 (T-47D) were incubated with dilutions of serum from immunized mice. Cells were washed, and specific antibody binding was detected with Alexa 647 labeled goat anti mouse IgG antibody (Invitrogen, catalog no: A21235, lot no: 2161043). Flow cytometric analyses were performed on a flow cytometry instrument (Intellicyte, IQue plus, Sartorius). In addition, mice serum was tested by imaging. Briefly, CHO-Nectin-4 or T-47D cells were incubated with dilutions of serum from immunized mice. Cells were washed, fixed with paraformaldehyde, washed, specific antibody binding was detected with secondary Alexa488 goat anti-mouse antibody and Hoechst (Invitrogen). Plates were scanned and analyzed on an imaging machine (Cytation 5, Biotek). Hybridomas supernatants were tested for Nectin-4 specific binding by ELISA, imaging and FACS as described above.

Generation of Hybridomas Producing mAbs to Nectin-4: To generate hybridomas producing mouse antibodies of the disclosure, splenocytes and lymph node cells were isolated from an immunized mouse and fused to an appropriate immortalized cell line, such as a mouse myeloma cell line. The resulting hybridomas were screened for the production of antigen-specific antibodies. For example, single cell suspensions of splenocytes, lymph node cells from immunized mice were fused to equal number of Sp2/0 non-secreting mouse IgG myeloma cells (ATCC, CRL 1581) by electrofusion. Cells were plated in flat bottom 96-well tissue culture plates, followed by 2 weeks of incubation in selection medium (HAT medium), then switched to hybridoma culture media. Approximately 10-14 days after cell plating, supernatants from individual wells were screened by ELISA, Imaging or FACS as described above. The antibody secreting hybridomas were transferred to 24-well plates, screened again, and if still positive for anti-Nectin-4, the positive hybridomas were subcloned by sorting using a single cell sorter. The stable subclones were then cultured in vitro to generate small amounts of antibodies to be used for purification and characterization.

Example 2: Binding of Anti-Nectin-4-Specific Antibodies

The binding specificity of the disclosed anti-Nectin-4 antibodies was assessed by ELISA. Briefly, human recombinant Nectin-4 protein was directly coated to ELISA plates. Purified antibodies were then added to the plates followed by detection by goat-anti-mouse IgG-HRP. After addition of ABTS substrate, ELISA plates were read using an ELISA plate reader (Bioteck). The controls depicted in FIG. 2: PC1 refers to a reference antibody (known to be a Nectin-4 specific recombinant antibody, made by Novarock Biotherapeutics, lot no: 03042020KD); the negative control is a human IgG1 (Dendritics, catalog no: DDXCH01P-100, lot no: DDXCH01-028).

FIG. 2 shows the binding activities of the disclosed eight Nectin-4-specific antibodies. N4_mAb 1 to N4_mAb 8 bind to human Nectin-4 protein in a dose-dependent manner. Additionally, the positive control also binds to human Nectin-4 protein in a dose dependent manner. Human IgG1 does not bind to human Nectin-4 protein.

The ELISA binding EC50 values of the eight anti-Nectin-4 antibodies, N4_mAb 1 to N4_mAb 8 and the positive control antibody were listed in Table 3 below.

TABLE 3

Binding of Nectin-4 antibodies to human Nectin-4 recombinant protein

| Antibody | ELISA EC50 (nM) |
|---|---|
| N4_mAb 1 | 0.14 |
| N4_mAb 2 | 0.12 |
| N4_mAb 3 | 1.51 |
| N4_mAb 4 | 1.12 |
| N4_mAb 5 | 0.13 |
| N4_mAb 6 | 0.03 |
| N4_mAb 7 | 0.04 |
| N4_mAb8 | 0.14 |
| PC1 | 0.34 |

Results from FIG. 2 and Table 3 indicate that the anti-human Nectin-4-specific antibodies are characterized by binding to human Nectin-4 with low EC50 values by ELISA.

The binding specificity of the disclosed anti-Nectin-4 antibodies was also assessed by FACS. Briefly, CHO-Nectin-4 cells (vs. parental CHO cells) or endogenous cell lines expressing Nectin-4 (T-47D) were incubated with dilutions of purified recombinant antibodies. Cells were washed, and specific antibody binding was detected with Alexa 647 labeled goat anti-mouse IgG antibody. Flow cytometric analysis was performed on a flow cytometry instrument (Intellicyte, IQue plus, Sartorius).

FIGS. 3A and 3B show the binding activities of the disclosed Nectin-4-specific antibodies. FIG. 3A shows that anti-Nectin-4 antibodies, N4_mAb 1 to N4_mAb 8, bind to human CHO-Nectin-4 cells in a dose-dependent manner; the positive control also binds to CHO-Nectin-4 cells in a dose dependent manner. The negative control human IgG1 does not bind to CHO-Nectin-4-cells. FIG. 3B shows that anti-Nectin-4 antibodies, N4_mAb 1 to N4_mAb 8, bind to the cell line SKBR3 that endogenously expresses Nectin-4 in a dose-dependent manner. The positive control also binds SKBR3 cells in a dose-dependent manner.

Table 4 shows the binding EC50 values of the disclosed eight Nectin-4 antibodies. N4_mAb 1 to N4_mAb 8 antibodies bind to CHO-Nectin-4 cells and SKBR3 cells by FACS.

TABLE 4

Binding of the Nectin-4 antibodies to Nectin-4 expressing cell lines by FACS

| Antibody | CHO-Nectin-4 EC50 (nM) | SKBR3 EC50 (nM) |
|---|---|---|
| N4_mAb 1 | 0.29 | 0.24 |
| N4_mAb 2 | 0.64 | 1.8 |
| N4_mAb 3 | 0.75 | 45 |
| N4_mAb 4 | 0.57 | 1.8 |
| N4_mAb 5 | 0.38 | 0.52 |
| N4_mAb 6 | 0.12 | 0.04 |
| N4_mAb 7 | 0.18 | 0.05 |
| N4_mAb 8 | 0.23 | 0.05 |
| PC1 | 0.04 | 0.07 |

Results from FIGS. 3A and 3B and Table 4 indicate that the anti-human Nectin-4-specific antibodies bind CHO-Nectin-4 cells and SKBR3 cells with low EC50 values by FACS.

The binding kinetics of the disclosed anti-Nectin-4-specific antibodies to recombinant human Nectin-4 was determined by Surface plasmon resonance (SPR) using BIAcore 3000 system. Briefly, CM5 chip was immobilized via amine coupling chemistry with anti-human IgG antibody (GE, Cat No BR-1000-12, lot 10283568) following the application wizards on Flow cell 4. Flow cell 3 remained unmodified to serve as a reference cell for subtraction of systematic instrument noise and drift. Run Fc4-3 detection with double blank (Fc3 and blank analyte buffer). Antibody samples were diluted to 1 ug/mL in HBS-EP and injected at a flow rate of 10 ul/min for 1 minute. Analyte recombinant human Nectin4-His protein was diluted from 10 to 0.156 nM (1:4 dilution, 5 points to 0 nM in HBS-EP buffer) and injected at 50 uL/minute for 2 minutes, followed by 6 minutes dissociation. All the analyses were performed with double blanks, Fc3 and blank analyte buffer, to reduce the background. Data were analyzed using BIAevaluation software (version 4.1.1) by 1:1 binding with mass transfer model with global fit to determine apparent binding kinetics.

The binding KD values for the disclosed anti-Nectin-4 antibodies are provided in Table 5. The results indicate that the anti-Nectin-4-specific antibodies bind to human recombinant Nectin-4 with KD values ranging from 1.72E-08 to 3.75E-10 M.

TABLE 5

SPR Binding KDs

| Antibody | KD (M) |
|---|---|
| N4_mAb 1 | 1.25E−9 |
| N4_mAb 2 | 8.84E−10 |
| N4_mAb 3 | 1.72E−8 |
| N4_mAb 4 | 1.26E−9 |
| N4_mAb 5 | 1.58E−9 |
| N4_mAb 6 | 3.92E−10 |
| N4_mAb 7 | 3.90E−10 |
| N4_mAb 8 | 3.75E−10 |

Example 3: Blocking of Nectin-1 Binding to Nectin-4 Expressing Cells

The ability of disclosed Nectin4-specific antibodies to block Nectin-1 binding to Nectin-4 expressing cells (CHO cells transfected with human Nectin-4) was determined by FACS. Briefly, CHO-Nectin-4 cells were incubated with dilutions of the disclosed Nectin-4 purified recombinant antibodies. Then, biotinylated human Nectin-1 with His tag (ACROBiosystems, catalog number: PV1-H5223, lot: 733-38GS1-47, 0.75 ug/ml) was added to the plate. After 30-minute incubation, cells were washed, followed by adding Streptavidin Alexa 647 (1:1000) to the samples. After a 30 minute incubation, the samples were analyzed on a flow cytometry instrument (Intellicyte, IQue plus, Sartorius) for Nectin-1 blocking activity. The positive control antibody used in this blocking assay is a reference antibody (known to be a recombinant Nectin-4 specific antibody, made by Novarock Biotherapeutics, lot: 03042020KD).

The data in Table 6 shows that the disclosed anti-Nectin-4 antibodies (N4_mAb 1 to N4_mAb 8) blocks human Nectin-1 binding to Nectin-4-CHO cells with low EC50 values, (0.12-130 nM). The positive control also blocked human Nectin-1 binding to CHO-Nectin-4 cells (EC50 0.16 nM).

TABLE 6

Blocking of Nectin-1 binding to CHO-Nectin-4 cells by anti-Nectin-4 Antibodies by FACS

| Anti-Nectin-4 mAb | Blocking EC50 (nM) |
|---|---|
| N4_mAb 1 | 0.78 |
| N4_mAb 2 | 0.64 |
| N4_mAb 3 | 0.3 |
| N4_mAb 4 | >130 |
| N4_mAb 5 | 0.5 |
| N4_mAb 6 | 0.12 |
| N4_mAb 7 | 0.21 |
| N4_mAb 8 | 0.33 |
| PC1 | 0.16 |

Example 4: Blocking of TIGIT Binding to Nectin-4 Expressing Cells

The ability of disclosed Nectin4-specific antibodies to block TIGIT binding to CHO-Nectin-4 cells was assessed by FACS. Briefly, CHO-Nectin-4 cells were incubated with dilutions of the disclosed purified recombinant antibodies. Then, biotinylated human TIGIT protein (SinoBiologic, catalog: 10917-H08H-B, lot: LC13AP0902) was added to the plate. After 30-minute incubation, cells were washed, followed by adding Streptavidin Alexa 647 (1:1000) to the samples. After a 30 minute incubation, the samples were analyzed on a flow cytometry instrument (Intellicyte, IQue plus, Sartorius) for TIGIT blocking activity. The positive control antibody used in this blocking assay is PC2, a Nectin-4 antibody with known blocking activity.

The data in Table 7 shows that the disclosed anti-Nectin-4 antibodies (N4_mAb 1 to N4_mAb 8) blocked human TIGIT binding to CHO-Nectin-4 cells (EC50 ranging 0.13-3.11 nM). The positive control also blocked human TIGIT binding to CHO-Nectin-4 cells (EC50 0.85 nM).

TABLE 7

Blocking of TIGIT binding to CHO-Nectin-4 cells by anti-Nectin-4 Antibodies

| Anti-Nectin-4 mAb | Blocking EC50 (nM) |
|---|---|
| N4_mAb 1 | 0.91 |
| N4_mAb 2 | 3.04 |
| N4_mAb 3 | 0.94 |
| N4_mAb 4 | >130 |
| N4_mAb 5 | 3.11 |
| N4_mAb 6 | 0.31 |
| N4_mAb 7 | 0.75 |
| N4_mAb 8 | 1.37 |
| PC2 | 0.85 |

Example 5: Antibody Binding Specificity to Nectin Family Proteins

The disclosed anti-Nectin-4 antibodies (N4-mAb 1 to N4-mAb 8) were tested for binding to human Nectin family proteins, namely Nectin-1 (ACROBiosystems, Catalog no: PV1-H5223, lot no: 733-38GS1-47), Nectin 2 (ACROBiosystems, Catalog no: PV2-H52E2, lot no: 1982-61 MS1-FD) and Nectin 3 (ACROBiosystems, Catalog no: PV3-H52E4, lot no: 1984-61 MS1-AC). by either ELISA or Gator binding assay. None of the Nectin-4 antibodies bind to Nectin-1, Nectin-2, or Nectin-3 (data not shown).

Example 6: Nectin-4 Antibody Binding Domain Determination

The extracellular part of human Nectin-4 (SEQ ID NO: 61) has 3 domains: one Ig-like V-type domain (amino acid 32 to 144) and two Ig-like C-type domains (amino acid 148 to 237, and 248 to 331 respectively). In order to determine the binding domain of Nectin-4 antibodies, three pcDNA3.1-based expression plasmids were made: one encodes full-length human Nectin-4, one encodes a variant with deletion from amino acid 148 to 331 (ΔC domain), and one expresses a variant with deletion from amino acid 32 to 147 ((ΔV domain). The plasmids were transfected into human 293T cells (ATCC) using TransIT-293 transfection reagent (Mirus Bio) and the binding affinity of disclosed antibodies to the transiently expressed Nectin-4 variants was measured by flow cytometry.

Table 8 shows the binding strength of the antibodies: "+++" denotes EC50 less than 5 nM, and "−" indicates EC50 is above the highest tested antibody concentration (133 nM). All antibodies except N4_mAb 4 bind to the variant lacking Ig-like C-type domains with the similar affinity as binding to full-length human Nectin-4. However, these antibodies lost the binding to the variant lacking Ig-like V-type domain, suggesting their respective binding epitope is within Ig-like V domain. N4_mAb 4 is unique with a binding epitope within Ig-like C-type domains (amino acid 148-331).

TABLE 8

Binding to human Nectin-4 variants with domain deletion

| Anti-Nectin-4 mAb | Full-length hNectin-4 | hNectin4 ΔC domain | hNectin4 ΔV domain |
|---|---|---|---|
| N4_mAb 1 | +++ | +++ | − |
| N4_mAb 2 | +++ | +++ | − |
| N4_mAb 3 | +++ | +++ | − |
| N4_mAb 4 | +++ | − | +++ |
| N4_mAb 5 | +++ | +++ | − |
| N4_mAb 6 | +++ | +++ | − |
| N4_mAb 7 | +++ | +++ | − |
| N4_mAb 8 | +++ | +++ | − |
| PC1 | +++ | +++ | − |

Example 7: Cross-Species Nectin-4 Binding

CDNAs encoding Nectin-4 protein from cynomolgus monkey (SEQ ID NO: 62), rat (SEQ ID NO: 63), or mouse (SEQ ID NO: 64) were separately cloned into a pcDNA3.1-based mammalian expression plasmid. The respective plasmids were transfected to human 293T cells in a similar way described in Example 6. The binding EC50 of disclosed human Nectin-4 antibodies to species-specific Nectin-4 transiently expressed on 293T cell surface was measured by flow cytometry.

The strength of the binding are reported in Table 9 and grouped into four categories, the strongest binding with EC50 values less than 5 nM are defined as "+++", binding EC50 values between 5 nM and 25 nM are defined as "++", binding EC50 values between 25 nM and 133 nM are marked as "+", and binding EC50 about 133 nM were indicated as "−". All antibodies bind to Nectin-4 from cynomolgus monkey and show varied affinity to Nectin-4 from rodent species.

TABLE 9

Binding to Nectin-4 from different species

| Anti-Nectin-4 mAb | Cyno Nectin-4 | Rat Nectin-4 | Mouse Nectin-4 |
|---|---|---|---|
| N4_mAb 1 | +++ | − | − |
| N4_mAb 2 | +++ | ++ | ++ |
| N4_mAb 3 | +++ | + | − |
| N4_mAb 4 | +++ | + | − |
| N4_mAb 5 | +++ | +++ | + |
| N4_mAb 6 | +++ | +++ | ++ |
| N4_mAb 7 | +++ | +++ | ++ |
| N4_mAb 8 | +++ | +++ | ++ |

Example 8: Anti-Nectin-4-Mediated Cytotoxicity

Endocytosis of the disclosed Nectin4-specific antibodies bound to Nectin-4 positive cells was measured by a cytotoxicity-based endocytosis assay that used the co-internalization of the target bound antibody together with an anti-Human IgG Fc-MMAF Antibody.

CHO-Nectin4 and SKBR3 cell lines were cultured in growth media (F12K+10% FBS and McCoy's 5a Medium+10% FBS, respectively). The cells were harvested and resuspended in their respective growth media and plated into the assay plate. The cells were incubated overnight at 37° C. Anti-Nectin4 antibodies were incubated with MMAF-conjugated Fab anti-hFc fragment (Moradec, Cat #AH-202AF-50) for 30 minutes, then added to cell plates, incubated for additional 96 hours. Cell titer glo (Promega, Cat #G7570)

was added to assess cell viability in each well. The signal was quantified using Neo2 plate reader (BioTek).

As demonstrated in Table 10 and FIG. 4A, the lead panel of anti-Nectin-4 antibodies induced endocytosis-derived cell toxicity in CHO-Nectin-4 cells with EC50 values ranging from 0.21 to 0.63 nM. Similarly, as shown in Table 10 and FIG. 4B, the panel of anti-Nectin-4 antibodies induced endocytosis-derived cell toxicity in SKBR3 cells with EC50 values ranging from 0.61-2.14 nM.

The lead panel antibodies also exhibited endocytosis-derived cell cytotoxicity in a breast tumor cell line T47D which endogenously expresses Nectin-4 (data not shown).

TABLE 10

| Endocytosis of anti-Nectin-4 antibodies | | |
|---|---|---|
| Antibody | Nectin-4-CHO EC50 (nM) | SKBR3 EC50 (nM) |
| N4_mAb 1 | 0.36 | 2.14 |
| N4_mAb 2 | 0.56 | 0.74 |
| N4_mAb 3 | 0.53 | 0.63 |
| N4_mAb 4 | 0.63 | 1.58 |
| N4_mAb 5 | 0.45 | 0.85 |
| N4_mAb 6 | 0.44 | 1.78 |
| N4_mAb 7 | 0.21 | 0.61 |
| N4_mAb 8 | 0.43 | 0.99 |
| PC1 | 0.33 | 0.39 |

Example 9: Kinetics of Antibody Internalization and Nectin-4 Protein Level

The kinetics of the internalization of selected anti-Nectin-4 antibodies and Nectin-4 protein level were measured in T47D cells. Briefly, indicated antibodies were labeled by Alexa Flour 488 using a labeling kit (Thermo Fisher, cat #A20181). Labelled antibodies were incubated with T47D cells at 37° C. for 0, 1, 4, and 24 hours. At each time point, cells were transferred to 4° C., and unlabelled antibodies were added for binding to membrane Nectin-4 protein. Cells were then fixed, and an Alexa Flour 647-labelled secondary antibody was added. The plate was then imaged by Cytation 5 (BioTek) for both dyes (green and red).

FIG. 5A shows the internalization kinetics of the selected anti-Nectin-4 antibodies. All four antibodies showed time-dependent internalization from 0 hr to 24 hr. At the same time points the level of membrane Nectin-4 was quantified and the results are shown in FIG. 5B. Among the antibodies, N4_mAb 2 showed faster internalization but also caused membrane Nectin-4 depletion. The other three antibodies did not show significant effect on cell surface Nectin-4 protein level.

Example 10: Antibody-Dependent Cellular Cytotoxicity (ADCC) in Tumor Cells Endogenously Expressing Nectin-4

The ADCC activity of the anti-Nectin-4 antibodies was measured by a bioluminescence assay. Briefly, anti-Nectin-4 antibodies were serially diluted in assay buffer containing RPMI+4% low IgG FBS and added to a mixture of individual target cell line (either T47D or SKBR3) and ADCC effector cells. The ADCC effector cells are Jurkat cells expressing CD16a which were activated upon recognition of the Fc portion of the bound Nectin-4 antibodies. The activation of the effector cells was detected using a Promega bioluminescence assay following the manufacturer's instruction (Promega, cat #E6130).

As shown in FIG. 6A, ADCC activity was only observed for N4_mAb 4 on T47D cells. None of the other antibodies including PC1 showed ADCC activity. On SKBR3 cells N4_mAb 4 also showed strong ADCC activity while N4 mAb 2 showed very mild activity and all other antibodies did not exhibit ADCC activity (FIG. 6B)

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein can be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

It is to be understood that the embodiments of the disclosure disclosed herein are illustrative of the principles of the present disclosure. Other modifications that can be employed are within the scope of the disclosure. Thus, by way of example, but not of limitation, alternative configurations of the present disclosure can be utilized in accordance with the teachings herein. Accordingly, the present disclosure is not limited to that precisely as shown and described.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary only, with the true scope and spirit of the disclosure being indicated by the following claims. All references, patents, and patent applications referred to in this application are herein incorporated by reference in their entirety.

What is claimed is:

1. An anti-Nectin-4 antibody or an antigen-binding fragment thereof comprising a variable heavy (VH) region and a variable light (VL) region, wherein the VH region and the VL region comprise a set of CDRs selected from:

(a) VH: CDR1: SEQ ID NO: 17, CDR2: SEQ ID NO: 18, CDR3: SEQ ID NO: 19; VL: CDR1: SEQ ID NO: 20, CDR2: SEQ ID NO: 21, CDR3: SEQ ID NO: 22;

(b) VH: CDR1: SEQ ID NO: 23, CDR2: SEQ ID NO: 24, CDR3: SEQ ID NO: 25; VL: CDR1: SEQ ID NO: 26, CDR2: SEQ ID NO: 27, CDR3: SEQ ID NO: 28;

(c) VH: CDR1: SEQ ID NO: 29, CDR2: SEQ ID NO: 30, CDR3: SEQ ID NO: 31; VL: CDR1: SEQ ID NO: 32, CDR2: SEQ ID NO: 33, CDR3: SEQ ID NO: 34;
(d) VH: CDR1: SEQ ID NO: 35 CDR2: SEQ ID NO: 36, CDR3: SEQ ID NO: 37; VL: CDR1: SEQ ID NO: 38, CDR2: SEQ ID NO: 39, CDR3: SEQ ID NO: 40;
(e) VH: CDR1: SEQ ID NO: 41, CDR2: SEQ ID NO: 42, CDR3: SEQ ID NO: 43; VL: CDR1: SEQ ID NO: 44, CDR2: SEQ ID NO: 45, CDR3: SEQ ID NO: 46;
(f) VH: CDR1: SEQ ID NO: 47, CDR2: SEQ ID NO: 48, CDR3: SEQ ID NO: 49; VL: CDR1: SEQ ID NO: 50, CDR2: SEQ ID NO: 51, CDR3: SEQ ID NO: 52;
(g) VH: CDR1: SEQ ID NO: 47, CDR2: SEQ ID NO: 53, CDR3: SEQ ID NO: 54; VL: CDR1: SEQ ID NO: 55, CDR2: SEQ ID NO: 56, CDR3: SEQ ID NO: 52; or
(h) VH: CDR1: SEQ ID NO: 57, CDR2: SEQ ID NO: 58, CDR3: SEQ ID NO: 59; VL: CDR1: SEQ ID NO: 50, CDR2: SEQ ID NO: 51, CDR3: SEQ ID NO: 60.

2. The anti-Nectin-4 antibody or antigen-binding fragment thereof of claim 1, wherein the antibody comprises:
(a) a heavy chain variable region having a sequence set forth in SEQ ID NO: 1 and a light chain variable region having a sequence set forth in SEQ ID NO: 2;
(b) a heavy chain variable region having a sequence set forth in SEQ ID NO: 3 and a light chain variable region having a sequence set forth in SEQ ID NO: 4;
(c) a heavy chain variable region having a sequence set forth in SEQ ID NO: 5 and a light chain variable region having a sequence set forth in SEQ ID NO: 6;
(d) a heavy chain variable region having a sequence set forth in SEQ ID NO: 7 and a light chain variable region having a sequence set forth in SEQ ID NO: 8;
(e) a heavy chain variable region having a sequence set forth in SEQ ID NO: 9 and a light chain variable region having a sequence set forth in SEQ ID NO: 10;
(f) a heavy chain variable region having a sequence set forth in SEQ ID NO: 11 and a light chain variable region having a sequence set forth in SEQ ID NO: 12;
(g) a heavy chain variable region having a sequence set forth in SEQ ID NO: 13 and a light chain variable region having a sequence set forth in SEQ ID NO: 14; or
(h) a heavy chain variable region having a sequence set forth in SEQ ID NO: 15 and a light chain variable region having a sequence set forth in SEQ ID NO: 16.

3. The anti-Nectin-4 antibody or antigen-binding fragment thereof of claim 1, wherein the antibody is a murine antibody.

4. The anti-Nectin-4 antibody or antigen-binding fragment thereof of claim 1, wherein the antibody is a chimeric antibody.

5. The anti-Nectin-4 antibody or antigen-binding fragment thereof of claim 1, wherein the antibody is a humanized antibody.

6. The anti-Nectin-4 antibody or antigen-binding fragment thereof according to claim 1, wherein the antibody or antigen-binding fragment thereof is conjugated to a cytotoxic agent.

7. The anti-Nectin-4 antibody or antigen-binding fragment thereof of claim 1, which is a full-length antibody.

8. The anti-Nectin-4 antibody or antigen-binding fragment thereof of claim 1, which is an antibody fragment.

9. The anti-Nectin-4 antibody or antigen-binding fragment thereof of claim 8, wherein the antibody fragment is selected from the group consisting of: Fab, Fab', F(ab')2, Fd, Fv, scFv and scFv-Fc fragment, a single-chain antibody, a minibody, and a diabody.

10. The anti-Nectin-4 antibody or antigen-binding fragment thereof of claim 1, wherein the antibody or antigen-binding fragment thereof binds to human Nectin-4.

11. A pharmaceutical composition comprising an antibody or antigen-binding fragment thereof according to claim 1 and a pharmaceutically acceptable carrier.

12. A method of modulating an immune system in a subject in need thereof by inhibiting binding of Nectin-4 to Nectin-1, the method comprising administering to the subject in need thereof a pharmaceutical composition according to claim 11.

13. A method of modulating an immune system in a subject in need thereof by inhibiting binding of Nectin-4 to TIGIT, the method comprising administering to the subject in need thereof a pharmaceutical composition according to claim 11.

14. A method of treating a Nectin-4 expressing cancer in a subject in need thereof, the method comprising administering to the subject in need thereof a pharmaceutical composition according to claim 11.

15. A method of diagnosing a cancer in a subject, the method comprising contacting a biological sample with an antibody or antigen-binding fragment thereof according to claim 1.

16. An isolated polynucleotide comprising a sequence encoding an anti-Nectin-4 antibody or antigen-binding fragment thereof according to claim 1.

17. An isolated polynucleotide according to claim 16, encoding an amino acid sequence as set forth in any one of SEQ ID NOS: 1 to 16.

18. A vector comprising a polynucleotide according to claim 17.

19. A host cell comprising a polynucleotide according to claim 17.

20. A method for the production of an anti-Nectin-4 antibody or antigen-binding fragment thereof according to claim 1, the method comprising culturing the host cell of claim 19.

* * * * *

```
SEQUENCE LISTING

<160> NUMBER OF SEQ ID NOS: 65

<210> SEQ ID NO 1
<211> LENGTH: 118
<212> TYPE: PRT
<213> ORGANISM: Artificial Sequence
<220> FEATURE:
<223> OTHER INFORMATION: Synthetic Sequence_N4_mAb 1_VH

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val Asn Trp Val Arg Gln Pro Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Ile Ser Lys Ser Gln Val Phe Phe
65                  70                  75                  80

Lys Met Asn Ser Leu Gln Ala Asp Asp Thr Ala Lys Tyr Tyr Cys Ala
                85                  90                  95

Arg Glu Gly Tyr Asp Gly Tyr Ala Met Asp Tyr Trp Gly Gln Gly Thr
            100                 105                 110

Ser Val Thr Val Ser Ser
        115


<210> SEQ ID NO 2
<211> LENGTH: 107
<212> TYPE: PRT
<213> ORGANISM: Artificial Sequence
<220> FEATURE:
<223> OTHER INFORMATION: Synthetic Sequence_N4_mAb 1_VL

<400> SEQUENCE: 2

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Phe Ser Ser
            20                  25                  30

Leu Ala Trp Tyr Gln Gln Lys Gln Gly Lys Ser Pro Gln Leu Leu Val
        35                  40                  45
```

```
Tyr Gly Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Trp Cys Gln His Phe Trp Gly Asn Pro Trp
                85                  90                  95

Thr Phe Gly Gly Gly Thr Lys Leu Glu Ile Lys
            100                 105


<210> SEQ ID NO 3
<211> LENGTH: 118
<212> TYPE: PRT
<213> ORGANISM: Artificial Sequence
<220> FEATURE:
<223> OTHER INFORMATION: Synthetic Sequence_N4_mAb 2_VH

<400> SEQUENCE: 3

Gln Val Gln Leu Lys Gln Ser Gly Pro Asn Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Ala His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Ser Ile Thr Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Lys Ile Gly Tyr Asp Gly Tyr Ala Met Asp Asn Trp Gly Gln Gly Thr
            100                 105                 110

Ser Val Thr Val Ser Ser
        115


<210> SEQ ID NO 4
<211> LENGTH: 107
<212> TYPE: PRT
<213> ORGANISM: Artificial Sequence
<220> FEATURE:
<223> OTHER INFORMATION: Synthetic Sequence_N4_ mAb 2_VH

<400> SEQUENCE: 4

Asp Phe Gln Val Thr Gln Ser Pro Ala Ser Leu Ser Ala Ser Val Gly
1               5                   10                  15

Glu Thr Val Thr Ile Thr Cys Arg Thr Ser Glu Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Ser Pro Trp
                85                  90                  95

Thr Phe Gly Gly Gly Thr Lys Leu Glu Ile Lys
            100                 105


<210> SEQ ID NO 5
```

```
<211> LENGTH: 120
<212> TYPE: PRT
<213> ORGANISM: Artificial Sequence
<220> FEATURE:
<223> OTHER INFORMATION: Synthetic Sequence_N4_mAb 3_VH

<400> SEQUENCE: 5

Glu Val Gln Leu Gln Gln Ser Gly Ala Glu Leu Val Lys Pro Gly Ala
1               5                   10                  15

Ser Val Lys Leu Ser Cys Thr Val Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Ile Ala Asp Lys Ala Ser Asn Thr Ala Tyr
65                  70                  75                  80

Leu Gln Leu Ser Ser Leu Thr Ser Glu Asp Ala Ala Val Tyr Tyr Cys
                85                  90                  95

Ala His Tyr Tyr Gly Ser Ser Tyr Phe Ala Met Asp Cys Trp Gly Gln
            100                 105                 110

Gly Thr Ser Val Thr Val Ser Ser
        115                 120


<210> SEQ ID NO 6
<211> LENGTH: 107
<212> TYPE: PRT
<213> ORGANISM: Artificial Sequence
<220> FEATURE:
<223> OTHER INFORMATION: Synthetic Sequence_N4_mAb 3_VL

<400> SEQUENCE: 6

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Thr
65                  70                  75                  80

Glu Asp Leu Ala Leu Tyr Tyr Cys Gln Gln His Tyr Ser Thr Pro Leu
                85                  90                  95

Thr Phe Gly Ala Gly Thr Lys Leu Glu Leu Lys
            100                 105


<210> SEQ ID NO 7
<211> LENGTH: 121
<212> TYPE: PRT
<213> ORGANISM: Artificial Sequence
<220> FEATURE:
<223> OTHER INFORMATION: Synthetic Sequence_N4_mAb 4_VH

<400> SEQUENCE: 7

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Ala
            20                  25                  30
```

```
Tyr Asn Trp His Trp Ile Arg Gln Phe Pro Gly Asn Lys Leu Glu Trp
        35                  40                  45

Met Gly Tyr Ile His Tyr Ser Gly Arg Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Leu Thr Thr Glu Asp Thr Ala Thr Tyr Tyr Cys
                85                  90                  95

Ala Arg Trp Ile Thr Thr Ala Thr Gly Trp Tyr Leu Asp Val Trp Gly
            100                 105                 110

Ala Gly Thr Thr Val Thr Val Ser Ser
        115                 120


<210> SEQ ID NO 8
<211> LENGTH: 111
<212> TYPE: PRT
<213> ORGANISM: Artificial Sequence
<220> FEATURE:
<223> OTHER INFORMATION: Synthetic Sequence_N4_mAb 4_VL

<400> SEQUENCE: 8

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Ala Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
            100                 105                 110


<210> SEQ ID NO 9
<211> LENGTH: 120
<212> TYPE: PRT
<213> ORGANISM: Artificial Sequence
<220> FEATURE:
<223> OTHER INFORMATION: Synthetic Sequence_N4_mAb 5_VH

<400> SEQUENCE: 9

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly His
            20                  25                  30

Tyr Met His Trp Val Lys Gln Ser His Gly Lys Ser Leu Glu Trp Ile
        35                  40                  45

Gly Arg Val Asn Pro Asn Asn Gly Gly Ser Ser Tyr Asn Gln Lys Phe
    50                  55                  60

Lys Asp Lys Ala Ile Leu Thr Val Asp Lys Ser Ser Thr Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Pro Leu Gly Gly Ser Tyr Gly Phe Ala Tyr Trp Gly Gln
            100                 105                 110
```

```
Gly Thr Leu Val Thr Val Ser Ala
        115                 120


<210> SEQ ID NO 10
<211> LENGTH: 111
<212> TYPE: PRT
<213> ORGANISM: Artificial Sequence
<220> FEATURE:
<223> OTHER INFORMATION: Synthetic Sequence_N4_mAb 5_VL

<400> SEQUENCE: 10

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Thr Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Met Lys
            100                 105                 110


<210> SEQ ID NO 11
<211> LENGTH: 116
<212> TYPE: PRT
<213> ORGANISM: Artificial Sequence
<220> FEATURE:
<223> OTHER INFORMATION: Synthetic Sequence_N4_mAb 6_VH

<400> SEQUENCE: 11

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Thr Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Thr Glu Asn Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Leu Tyr Tyr Phe Asp Phe Trp Gly Gln Gly Thr Thr Leu
            100                 105                 110

Thr Val Ser Ser
        115


<210> SEQ ID NO 12
<211> LENGTH: 107
<212> TYPE: PRT
<213> ORGANISM: Artificial Sequence
<220> FEATURE:
<223> OTHER INFORMATION: Synthetic Sequence_N4_mAb 6_VL

<400> SEQUENCE: 12
```

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Asn Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Asp Thr Gly Val Pro Asp Arg Phe Thr Gly
    50                  55                  60

Ser Gly Phe Gly Thr Asp Phe Thr Phe Thr Ile Ser Ser Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105


<210> SEQ ID NO 13
<211> LENGTH: 116
<212> TYPE: PRT
<213> ORGANISM: Artificial Sequence
<220> FEATURE:
<223> OTHER INFORMATION: Synthetic Sequence_N4_mAb 7_VH

<400> SEQUENCE: 13

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Thr Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Ala Gly Ile Lys Ser Asn Glu Lys Phe
    50                  55                  60

Lys Gly Lys Thr Thr Leu Thr Ala Asp Lys Ser Ser Ser Thr Ala Tyr
65                  70                  75                  80

Met Leu Leu Ser Ser Leu Thr Ser Glu Asp Ser Ala Ile Tyr Phe Cys
                85                  90                  95

Ala Arg Gly Val Tyr Phe Phe Asp Tyr Trp Gly Gln Gly Thr Thr Leu
            100                 105                 110

Thr Val Ser Ser
        115


<210> SEQ ID NO 14
<211> LENGTH: 107
<212> TYPE: PRT
<213> ORGANISM: Artificial Sequence
<220> FEATURE:
<223> OTHER INFORMATION: Synthetic Sequence_N4_mAb 7_VL

<400> SEQUENCE: 14

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Asn Asn Asp
            20                  25                  30

Val Ser Trp Phe Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Tyr Gly Thr Asp Phe Thr Phe Thr Ile Thr Thr Val Gln Ala
65                  70                  75                  80
```

```
Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105


<210> SEQ ID NO 15
<211> LENGTH: 116
<212> TYPE: PRT
<213> ORGANISM: Artificial Sequence
<220> FEATURE:
<223> OTHER INFORMATION: Synthetic Sequence_N4_mAb 8_VH

<400> SEQUENCE: 15

Gln Val Gln Leu Gln Gln Ser Gly Pro Val Leu Val Lys Pro Gly Ala
1               5                   10                  15

Ser Val Arg Ile Ser Cys Lys Ala Ser Gly Tyr Thr Phe Thr Ser Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Asn Phe
    50                  55                  60

Arg Asp Lys Ala Thr Leu Thr Ala Asp Lys Ser Ser Ser Thr Ser Tyr
65                  70                  75                  80

Met Gln Leu Ser Ser Leu Thr Ser Glu Asp Ser Ala Val Tyr Phe Cys
                85                  90                  95

Ala Arg Gly Ile Tyr Tyr Phe Asp Tyr Trp Gly Gln Gly Thr Thr Leu
            100                 105                 110

Thr Val Ser Ser
        115


<210> SEQ ID NO 16
<211> LENGTH: 107
<212> TYPE: PRT
<213> ORGANISM: Artificial Sequence
<220> FEATURE:
<223> OTHER INFORMATION: Synthetic Sequence_N4_mAb 8_VL

<400> SEQUENCE: 16

Ile Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Asn Asn Asp
            20                  25                  30

Val Ala Trp Tyr Gln Glu Lys Pro Gly Gln Ser Pro Lys Leu Leu Ile
        35                  40                  45

Tyr Tyr Ala Ser Asn Arg Asp Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys His Gln Asp Tyr Ser Ser Pro Phe
                85                  90                  95

Thr Phe Gly Ser Gly Thr Lys Leu Glu Ile Lys
            100                 105


<210> SEQ ID NO 17
<211> LENGTH: 5
<212> TYPE: PRT
<213> ORGANISM: Artificial Sequence
<220> FEATURE:
<223> OTHER INFORMATION: Synthetic Sequence_N4_mAb 1_VH
```

<400> SEQUENCE: 17

Asn Tyr Gly Val Asn
1 5

<210> SEQ ID NO 18
<211> LENGTH: 16
<212> TYPE: PRT
<213> ORGANISM: Artificial Sequence
<220> FEATURE:
<223> OTHER INFORMATION: Synthetic Sequence_N4_mAb 1_VH

<400> SEQUENCE: 18

Val Ile Trp Ser Gly Gly Ser Thr Asp Tyr Asn Ala Ala Phe Ile Ser
1 5 10 15

<210> SEQ ID NO 19
<211> LENGTH: 10
<212> TYPE: PRT
<213> ORGANISM: Artificial Sequence
<220> FEATURE:
<223> OTHER INFORMATION: Synthetic Sequence_N4_mAb 1_VH

<400> SEQUENCE: 19

Glu Gly Tyr Asp Gly Tyr Ala Met Asp Tyr
1 5 10

<210> SEQ ID NO 20
<211> LENGTH: 11
<212> TYPE: PRT
<213> ORGANISM: Artificial Sequence
<220> FEATURE:
<223> OTHER INFORMATION: Synthetic Sequence_N4_mAb 1_VL

<400> SEQUENCE: 20

Arg Ala Ser Glu Asn Ile Phe Ser Ser Leu Ala
1 5 10

<210> SEQ ID NO 21
<211> LENGTH: 7
<212> TYPE: PRT
<213> ORGANISM: Artificial Sequence
<220> FEATURE:
<223> OTHER INFORMATION: Synthetic Sequence_N4_mAb 1_VL

<400> SEQUENCE: 21

Gly Ala Thr Asn Leu Ala Asp
1 5

<210> SEQ ID NO 22
<211> LENGTH: 9
<212> TYPE: PRT
<213> ORGANISM: Artificial Sequence
<220> FEATURE:
<223> OTHER INFORMATION: Synthetic Sequence_N4_mAb 1_VL

<400> SEQUENCE: 22

Gln His Phe Trp Gly Asn Pro Trp Thr
1 5

<210> SEQ ID NO 23
<211> LENGTH: 5
<212> TYPE: PRT
<213> ORGANISM: Artificial Sequence
<220> FEATURE:
<223> OTHER INFORMATION: Synthetic Sequence_N4_mAb 2_VH

<400> SEQUENCE: 23

Thr Tyr Gly Ala His
1 5

<210> SEQ ID NO 24
<211> LENGTH: 16
<212> TYPE: PRT
<213> ORGANISM: Artificial Sequence
<220> FEATURE:
<223> OTHER INFORMATION: Synthetic Sequence_N4_mAb 2_VH

<400> SEQUENCE: 24

Val Ile Trp Arg Gly Gly Ser Thr Asp Tyr Asn Ala Ala Phe Met Ser
1 5 10 15

<210> SEQ ID NO 25
<211> LENGTH: 10
<212> TYPE: PRT
<213> ORGANISM: Artificial Sequence
<220> FEATURE:
<223> OTHER INFORMATION: Synthetic Sequence_N4_mAb 2_VH

<400> SEQUENCE: 25

Ile Gly Tyr Asp Gly Tyr Ala Met Asp Asn
1 5 10

<210> SEQ ID NO 26
<211> LENGTH: 11
<212> TYPE: PRT
<213> ORGANISM: Artificial Sequence
<220> FEATURE:
<223> OTHER INFORMATION: Synthetic Sequence_N4_ mAb 2_VH

<400> SEQUENCE: 26

Arg Thr Ser Glu Asn Ile His Asn Tyr Leu Ala
1 5 10

<210> SEQ ID NO 27
<211> LENGTH: 7
<212> TYPE: PRT
<213> ORGANISM: Artificial Sequence
<220> FEATURE:
<223> OTHER INFORMATION: Synthetic Sequence_N4_ mAb 2_VH

<400> SEQUENCE: 27

Asn Ala Lys Thr Leu Ala Asp
1 5

<210> SEQ ID NO 28
<211> LENGTH: 9
<212> TYPE: PRT
<213> ORGANISM: Artificial Sequence
<220> FEATURE:
<223> OTHER INFORMATION: Synthetic Sequence_N4_ mAb 2_VH

<400> SEQUENCE: 28

Gln His Phe Trp Ser Ser Pro Trp Thr
1 5

<210> SEQ ID NO 29
<211> LENGTH: 5
<212> TYPE: PRT
<213> ORGANISM: Artificial Sequence
<220> FEATURE:
<223> OTHER INFORMATION: Synthetic Sequence_N4_mAb 3_VH

<400> SEQUENCE: 29

Asp Thr Tyr Met His
1 5

<210> SEQ ID NO 30
<211> LENGTH: 17
<212> TYPE: PRT
<213> ORGANISM: Artificial Sequence
<220> FEATURE:
<223> OTHER INFORMATION: Synthetic Sequence_N4_mAb 3_VH

<400> SEQUENCE: 30

Arg Ile Asp Pro Ala Asn Gly Asn Thr Lys Tyr Asp Pro Lys Phe Gln
1 5 10 15

Gly

<210> SEQ ID NO 31
<211> LENGTH: 11
<212> TYPE: PRT
<213> ORGANISM: Artificial Sequence
<220> FEATURE:
<223> OTHER INFORMATION: Synthetic Sequence_N4_mAb 3_VH

<400> SEQUENCE: 31

Tyr Tyr Gly Ser Ser Tyr Phe Ala Met Asp Cys
1 5 10

<210> SEQ ID NO 32
<211> LENGTH: 11
<212> TYPE: PRT
<213> ORGANISM: Artificial Sequence
<220> FEATURE:
<223> OTHER INFORMATION: Synthetic Sequence_N4_mAb 3_VL

<400> SEQUENCE: 32

Lys Ala Ser Gln Asp Val Ser Thr Ala Val Ala
1 5 10

<210> SEQ ID NO 33
<211> LENGTH: 7
<212> TYPE: PRT
<213> ORGANISM: Artificial Sequence
<220> FEATURE:
<223> OTHER INFORMATION: Synthetic Sequence_N4_mAb 3_VL

<400> SEQUENCE: 33

Trp Ala Ser Thr Arg His Thr
1 5

<210> SEQ ID NO 34
<211> LENGTH: 9
<212> TYPE: PRT
<213> ORGANISM: Artificial Sequence
<220> FEATURE:
<223> OTHER INFORMATION: Synthetic Sequence_N4_mAb 3_VL

<400> SEQUENCE: 34

Gln Gln His Tyr Ser Thr Pro Leu Thr
1 5

<210> SEQ ID NO 35
<211> LENGTH: 6
<212> TYPE: PRT
<213> ORGANISM: Artificial Sequence
<220> FEATURE:
<223> OTHER INFORMATION: Synthetic Sequence_N4_mAb 4_VH

<400> SEQUENCE: 35

Ser Ala Tyr Asn Trp His
1 5

<210> SEQ ID NO 36
<211> LENGTH: 16
<212> TYPE: PRT
<213> ORGANISM: Artificial Sequence
<220> FEATURE:
<223> OTHER INFORMATION: Synthetic Sequence_N4_mAb 4_VH

<400> SEQUENCE: 36

Tyr Ile His Tyr Ser Gly Arg Thr Asn Tyr Asn Pro Ser Leu Lys Ser
1 5 10 15

<210> SEQ ID NO 37
<211> LENGTH: 12
<212> TYPE: PRT
<213> ORGANISM: Artificial Sequence
<220> FEATURE:
<223> OTHER INFORMATION: Synthetic Sequence_N4_mAb 4_VH

<400> SEQUENCE: 37

Trp Ile Thr Thr Ala Thr Gly Trp Tyr Leu Asp Val
1 5 10

<210> SEQ ID NO 38
<211> LENGTH: 15
<212> TYPE: PRT
<213> ORGANISM: Artificial Sequence
<220> FEATURE:
<223> OTHER INFORMATION: Synthetic Sequence_N4_mAb 4_VL

<400> SEQUENCE: 38

Arg Ala Ser Glu Ser Val Ala Asn Tyr Gly Ile Ser Phe Met Asn
1 5 10 15

<210> SEQ ID NO 39
<211> LENGTH: 7
<212> TYPE: PRT
<213> ORGANISM: Artificial Sequence
<220> FEATURE:
<223> OTHER INFORMATION: Synthetic Sequence_N4_mAb 4_VL

<400> SEQUENCE: 39

Ala Ala Ser Asn Gln Gly Ser
1 5

<210> SEQ ID NO 40
<211> LENGTH: 9
<212> TYPE: PRT
<213> ORGANISM: Artificial Sequence
<220> FEATURE:
<223> OTHER INFORMATION: Synthetic Sequence_N4_mAb 4_VL

<400> SEQUENCE: 40

Gln Gln Ser Lys Glu Val Pro Trp Thr
1 5

<210> SEQ ID NO 41
<211> LENGTH: 5
<212> TYPE: PRT
<213> ORGANISM: Artificial Sequence
<220> FEATURE:
<223> OTHER INFORMATION: Synthetic Sequence_N4_mAb 5_VH

<400> SEQUENCE: 41

Gly His Tyr Met His
1 5

<210> SEQ ID NO 42
<211> LENGTH: 17
<212> TYPE: PRT
<213> ORGANISM: Artificial Sequence
<220> FEATURE:
<223> OTHER INFORMATION: Synthetic Sequence_N4_mAb 5_VH

<400> SEQUENCE: 42

Arg Val Asn Pro Asn Asn Gly Gly Ser Ser Tyr Asn Gln Lys Phe Lys
1 5 10 15

Asp

<210> SEQ ID NO 43
<211> LENGTH: 11
<212> TYPE: PRT
<213> ORGANISM: Artificial Sequence
<220> FEATURE:
<223> OTHER INFORMATION: Synthetic Sequence_N4_mAb 5_VH

<400> SEQUENCE: 43

Asp Pro Leu Gly Gly Ser Tyr Gly Phe Ala Tyr
1 5 10

<210> SEQ ID NO 44
<211> LENGTH: 15
<212> TYPE: PRT
<213> ORGANISM: Artificial Sequence
<220> FEATURE:
<223> OTHER INFORMATION: Synthetic Sequence_N4_mAb 5_VL

<400> SEQUENCE: 44

Arg Ala Ser Gln Ser Val Thr Thr Ser Ser Tyr Ser Tyr Met His
1 5 10 15

<210> SEQ ID NO 45
<211> LENGTH: 7
<212> TYPE: PRT
<213> ORGANISM: Artificial Sequence
<220> FEATURE:
<223> OTHER INFORMATION: Synthetic Sequence_N4_mAb 5_VL

<400> SEQUENCE: 45

Tyr Ala Ser Asn Leu Glu Ser
1 5

<210> SEQ ID NO 46
<211> LENGTH: 9
<212> TYPE: PRT
<213> ORGANISM: Artificial Sequence
<220> FEATURE:
<223> OTHER INFORMATION: Synthetic Sequence_N4_mAb 5_VL

<400> SEQUENCE: 46

Gln His Ser Trp Glu Ile Pro Tyr Thr
1 5

<210> SEQ ID NO 47
<211> LENGTH: 5
<212> TYPE: PRT
<213> ORGANISM: Artificial Sequence
<220> FEATURE:
<223> OTHER INFORMATION: Synthetic Sequence_N4_mAb 6_VH

<400> SEQUENCE: 47

Thr Tyr Tyr Ile His
1 5

<210> SEQ ID NO 48
<211> LENGTH: 17
<212> TYPE: PRT
<213> ORGANISM: Artificial Sequence
<220> FEATURE:
<223> OTHER INFORMATION: Synthetic Sequence_N4_mAb 6_VH

<400> SEQUENCE: 48

Trp Ile Tyr Pro Gly Asn Val Asn Thr Lys Tyr Thr Glu Asn Phe Lys
1 5 10 15

Asp

<210> SEQ ID NO 49
<211> LENGTH: 7
<212> TYPE: PRT
<213> ORGANISM: Artificial Sequence
<220> FEATURE:
<223> OTHER INFORMATION: Synthetic Sequence_N4_mAb 6_VH

<400> SEQUENCE: 49

Gly Leu Tyr Tyr Phe Asp Phe
1 5

<210> SEQ ID NO 50
<211> LENGTH: 11
<212> TYPE: PRT
<213> ORGANISM: Artificial Sequence
<220> FEATURE:
<223> OTHER INFORMATION: Synthetic Sequence_N4_mAb 6_VL

<400> SEQUENCE: 50

Lys Ala Ser Gln Ser Val Asn Asn Asp Val Ala
1 5 10

<210> SEQ ID NO 51
<211> LENGTH: 7
<212> TYPE: PRT
<213> ORGANISM: Artificial Sequence
<220> FEATURE:
<223> OTHER INFORMATION: Synthetic Sequence_N4_mAb 6_VL

<400> SEQUENCE: 51

Tyr Ala Ser Asn Arg Asp Thr
1 5

<210> SEQ ID NO 52
<211> LENGTH: 9
<212> TYPE: PRT
<213> ORGANISM: Artificial Sequence
<220> FEATURE:
<223> OTHER INFORMATION: Synthetic Sequence_N4_mAb 6_VL

<400> SEQUENCE: 52

Gln Gln Asp Tyr Ser Ser Pro Tyr Thr
1 5

<210> SEQ ID NO 53
<211> LENGTH: 17
<212> TYPE: PRT
<213> ORGANISM: Artificial Sequence
<220> FEATURE:
<223> OTHER INFORMATION: Synthetic Sequence_N4_mAb 7_VH

```
<400> SEQUENCE: 53

Trp Ile Tyr Pro Gly Asn Ala Gly Ile Lys Ser Asn Glu Lys Phe Lys
1               5                   10                  15

Gly


<210> SEQ ID NO 54
<211> LENGTH: 7
<212> TYPE: PRT
<213> ORGANISM: Artificial Sequence
<220> FEATURE:
<223> OTHER INFORMATION: Synthetic Sequence_N4_mAb 7_VH

<400> SEQUENCE: 54

Gly Val Tyr Phe Phe Asp Tyr
1               5


<210> SEQ ID NO 55
<211> LENGTH: 11
<212> TYPE: PRT
<213> ORGANISM: Artificial Sequence
<220> FEATURE:
<223> OTHER INFORMATION: Synthetic Sequence_N4_mAb 7_VL

<400> SEQUENCE: 55

Lys Ala Ser Gln Ser Val Asn Asn Asp Val Ser
1               5                   10


<210> SEQ ID NO 56
<211> LENGTH: 7
<212> TYPE: PRT
<213> ORGANISM: Artificial Sequence
<220> FEATURE:
<223> OTHER INFORMATION: Synthetic Sequence_N4_mAb 7_VL

<400> SEQUENCE: 56

Tyr Ala Ser Asn Arg Tyr Thr
1               5


<210> SEQ ID NO 57
<211> LENGTH: 5
<212> TYPE: PRT
<213> ORGANISM: Artificial Sequence
<220> FEATURE:
<223> OTHER INFORMATION: Synthetic Sequence_N4_mAb 8_VH

<400> SEQUENCE: 57

Ser Tyr Tyr Ile His
1               5


<210> SEQ ID NO 58
<211> LENGTH: 17
<212> TYPE: PRT
<213> ORGANISM: Artificial Sequence
<220> FEATURE:
<223> OTHER INFORMATION: Synthetic Sequence_N4_mAb 8_VH

<400> SEQUENCE: 58

Trp Ile Tyr Pro Gly Asn Val Asn Thr Lys Tyr Asn Glu Asn Phe Arg
1               5                   10                  15

Asp


<210> SEQ ID NO 59
<211> LENGTH: 7
<212> TYPE: PRT
```

```
<213> ORGANISM: Artificial Sequence
<220> FEATURE:
<223> OTHER INFORMATION: Synthetic Sequence_N4_mAb 8_VH

<400> SEQUENCE: 59

Gly Ile Tyr Tyr Phe Asp Tyr
1               5


<210> SEQ ID NO 60
<211> LENGTH: 9
<212> TYPE: PRT
<213> ORGANISM: Artificial Sequence
<220> FEATURE:
<223> OTHER INFORMATION: Synthetic Sequence_N4_mAb 8_VL

<400> SEQUENCE: 60

His Gln Asp Tyr Ser Ser Pro Phe Thr
1               5


<210> SEQ ID NO 61
<211> LENGTH: 510
<212> TYPE: PRT
<213> ORGANISM: Homo sapiens

<400> SEQUENCE: 61

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
            20                  25                  30

Glu Leu Glu Thr Ser Asp Val Val Thr Val Val Leu Gly Gln Asp Ala
        35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
        115                 120                 125

Val Ser Thr Phe Pro Ala Gly Ser Phe Gln Ala Arg Leu Arg Leu Arg
    130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
    210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Ile Gly Arg Glu Gly Ala Met Leu Lys Cys Leu Ser
```

```
            260                 265                 270

Glu Gly Gln Pro Pro Pro Ser Tyr Asn Trp Thr Arg Leu Asp Gly Pro
        275                 280                 285

Leu Pro Ser Gly Val Arg Val Asp Gly Asp Thr Leu Gly Phe Pro Pro
    290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
                325                 330                 335

Glu Asp Ser Gly Lys Gln Val Asp Leu Val Ser Ala Ser Val Val Val
            340                 345                 350

Val Gly Val Ile Ala Ala Leu Leu Phe Cys Leu Leu Val Val Val Val
        355                 360                 365

Val Leu Met Ser Arg Tyr His Arg Arg Lys Ala Gln Gln Met Thr Gln
    370                 375                 380

Lys Tyr Glu Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
                405                 410                 415

Gly Leu Arg Ala Glu Gly His Pro Asp Ser Leu Lys Asp Asn Ser Ser
            420                 425                 430

Cys Ser Val Met Ser Glu Glu Pro Glu Gly Arg Ser Tyr Ser Thr Leu
        435                 440                 445

Thr Thr Val Arg Glu Ile Glu Thr Gln Thr Glu Leu Leu Ser Pro Gly
    450                 455                 460

Ser Gly Arg Ala Glu Glu Glu Glu Asp Gln Asp Glu Gly Ile Lys Gln
465                 470                 475                 480

Ala Met Asn His Phe Val Gln Glu Asn Gly Thr Leu Arg Ala Lys Pro
                485                 490                 495

Thr Gly Asn Gly Ile Tyr Ile Asn Gly Arg Gly His Leu Val
            500                 505                 510


<210> SEQ ID NO 62
<211> LENGTH: 510
<212> TYPE: PRT
<213> ORGANISM: Macaca fascicularis

<400> SEQUENCE: 62

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
            20                  25                  30

Glu Leu Glu Thr Ser Asp Val Val Thr Val Val Leu Gly Gln Asp Ala
        35                  40                  45

Lys Leu Pro Cys Phe Tyr Arg Gly Asp Ser Gly Glu Gln Val Gly Gln
    50                  55                  60

Val Ala Trp Ala Arg Ala Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
        115                 120                 125
```

```
Val Ser Thr Phe Pro Ala Gly Ser Phe Gln Ala Arg Leu Arg Leu Arg
    130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
    210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Val Gly Arg Glu Gly Ala Met Leu Lys Cys Leu Ser
            260                 265                 270

Glu Gly Gln Pro Pro Pro Ser Tyr Asn Trp Thr Arg Leu Asp Gly Pro
        275                 280                 285

Leu Pro Ser Gly Val Arg Val Asp Gly Asp Thr Leu Gly Phe Pro Pro
    290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
                325                 330                 335

Glu Asp Ser Gly Lys Gln Val Asp Leu Val Ser Ala Ser Val Val Val
            340                 345                 350

Val Gly Val Ile Ala Ala Leu Leu Phe Cys Leu Leu Val Val Val Val
        355                 360                 365

Val Leu Met Ser Arg Tyr His Arg Arg Lys Ala Gln Gln Met Thr Gln
    370                 375                 380

Lys Tyr Glu Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
                405                 410                 415

Gly Leu Arg Ala Glu Gly His Pro Asp Ser Leu Lys Asp Asn Ser Ser
            420                 425                 430

Cys Ser Val Met Ser Glu Glu Pro Glu Gly Arg Ser Tyr Ser Thr Leu
        435                 440                 445

Thr Thr Val Arg Glu Ile Glu Thr Gln Thr Glu Leu Leu Ser Pro Gly
    450                 455                 460

Ser Gly Arg Thr Glu Glu Glu Glu Asp Gln Asp Glu Gly Ile Lys Gln
465                 470                 475                 480

Ala Met Asn His Phe Val Gln Glu Asn Gly Thr Leu Arg Ala Lys Pro
                485                 490                 495

Thr Gly Asn Gly Ile Tyr Ile Asn Gly Arg Gly His Leu Val
            500                 505                 510


<210> SEQ ID NO 63
<211> LENGTH: 508
<212> TYPE: PRT
<213> ORGANISM: Rattus norvegicus

<400> SEQUENCE: 63
```

```
Met Pro Leu Ser Leu Gly Ala Glu Met Trp Gly Pro Glu Ala Trp Leu
1               5                   10                  15

Leu Leu Leu Phe Leu Ala Ser Phe Thr Gly Arg Tyr Ser Ala Gly Glu
            20                  25                  30

Leu Glu Thr Ser Asp Leu Val Thr Val Val Leu Gly Gln Asp Ala Lys
        35                  40                  45

Leu Pro Cys Phe Tyr Arg Gly Asp Pro Asp Glu Gln Val Gly Gln Val
    50                  55                  60

Ala Trp Ala Arg Val Asp Pro Asn Glu Gly Thr Arg Glu Leu Ala Leu
65                  70                  75                  80

Leu His Ser Lys Tyr Gly Leu His Val Ser Pro Ala Tyr Glu Asp Arg
                85                  90                  95

Val Glu Gln Pro Pro Pro Pro Arg Asp Pro Leu Asp Gly Ser Ile Leu
            100                 105                 110

Leu Arg Asn Ala Val Gln Ala Asp Glu Gly Glu Tyr Glu Cys Arg Val
        115                 120                 125

Ser Thr Phe Pro Ala Gly Ser Phe Gln Ala Arg Met Arg Leu Arg Val
    130                 135                 140

Leu Val Pro Pro Leu Pro Ser Leu Asn Pro Gly Pro Pro Leu Glu Glu
145                 150                 155                 160

Gly Gln Gly Leu Thr Leu Ala Ala Ser Cys Thr Ala Glu Gly Ser Pro
                165                 170                 175

Ala Pro Ser Val Thr Trp Asp Thr Glu Val Lys Gly Thr Gln Ser Ser
            180                 185                 190

Arg Ser Phe Lys His Ser Arg Ser Ala Ala Val Thr Ser Glu Phe His
        195                 200                 205

Leu Val Pro Ser Arg Ser Met Asn Gly Gln Pro Leu Thr Cys Val Val
    210                 215                 220

Ser His Pro Gly Leu Leu Gln Asp Gln Arg Ile Thr His Thr Leu Gln
225                 230                 235                 240

Val Ala Phe Leu Ala Glu Ala Ser Val Arg Gly Leu Glu Asp Gln Asn
                245                 250                 255

Leu Trp His Val Gly Arg Glu Gly Ala Thr Leu Lys Cys Leu Ser Glu
            260                 265                 270

Gly Gln Pro Pro Pro Lys Tyr Asn Trp Thr Arg Leu Asp Gly Pro Leu
        275                 280                 285

Pro Ser Gly Val Arg Val Lys Gly Asp Thr Leu Gly Phe Pro Pro Leu
    290                 295                 300

Thr Thr Glu His Ser Gly Val Tyr Val Cys His Val Ser Asn Glu Leu
305                 310                 315                 320

Ser Ser Arg Ala Ser Gln Val Thr Val Glu Val Leu Asp Pro Glu Asp
                325                 330                 335

Pro Gly Lys Gln Val Asp Leu Val Ser Ala Ser Val Val Val Val Gly
            340                 345                 350

Val Ile Ala Ala Leu Leu Phe Cys Leu Leu Val Val Val Val Val Leu
        355                 360                 365

Met Ser Arg Tyr His Arg Arg Lys Ala Gln Gln Met Thr Gln Lys Tyr
    370                 375                 380

Glu Glu Glu Leu Thr Leu Thr Arg Glu Asn Ser Ile Arg Arg Leu His
385                 390                 395                 400

Ser His His Thr Asp Pro Arg Ser Gln Pro Glu Glu Ser Val Gly Leu
                405                 410                 415
```

```
Arg Ala Glu Gly His Pro Asp Ser Leu Lys Asp Asn Ser Ser Cys Ser
            420                 425                 430

Val Met Ser Glu Glu Pro Glu Gly Arg Ser Tyr Ser Thr Leu Thr Thr
        435                 440                 445

Val Arg Glu Ile Glu Thr Gln Thr Glu Leu Leu Ser Pro Gly Ser Gly
    450                 455                 460

Arg Thr Glu Glu Glu Asp Asp Gln Asp Glu Gly Ile Lys Gln Ala Met
465                 470                 475                 480

Asn His Phe Val Gln Glu Asn Gly Thr Leu Arg Ala Lys Pro Thr Gly
                485                 490                 495

Asn Gly Ile Tyr Ile Asn Gly Arg Gly His Leu Val
            500                 505


<210> SEQ ID NO 64
<211> LENGTH: 508
<212> TYPE: PRT
<213> ORGANISM: Mus musculus

<400> SEQUENCE: 64

Met Pro Leu Ser Leu Gly Ala Glu Met Trp Gly Pro Glu Ala Trp Leu
1               5                   10                  15

Arg Leu Leu Phe Leu Ala Ser Phe Thr Gly Gln Tyr Ser Ala Gly Glu
            20                  25                  30

Leu Glu Thr Ser Asp Val Val Thr Val Val Leu Gly Gln Asp Ala Lys
        35                  40                  45

Leu Pro Cys Phe Tyr Arg Gly Asp Pro Asp Glu Gln Val Gly Gln Val
    50                  55                  60

Ala Trp Ala Arg Val Asp Pro Asn Glu Gly Ile Arg Glu Leu Ala Leu
65                  70                  75                  80

Leu His Ser Lys Tyr Gly Leu His Val Asn Pro Ala Tyr Glu Asp Arg
                85                  90                  95

Val Glu Gln Pro Pro Pro Pro Arg Asp Pro Leu Asp Gly Ser Val Leu
            100                 105                 110

Leu Arg Asn Ala Val Gln Ala Asp Glu Gly Glu Tyr Glu Cys Arg Val
        115                 120                 125

Ser Thr Phe Pro Ala Gly Ser Phe Gln Ala Arg Met Arg Leu Arg Val
    130                 135                 140

Leu Val Pro Pro Leu Pro Ser Leu Asn Pro Gly Pro Pro Leu Glu Glu
145                 150                 155                 160

Gly Gln Gly Leu Thr Leu Ala Ala Ser Cys Thr Ala Glu Gly Ser Pro
                165                 170                 175

Ala Pro Ser Val Thr Trp Asp Thr Glu Val Lys Gly Thr Gln Ser Ser
            180                 185                 190

Arg Ser Phe Thr His Pro Arg Ser Ala Ala Val Thr Ser Glu Phe His
        195                 200                 205

Leu Val Pro Ser Arg Ser Met Asn Gly Gln Pro Leu Thr Cys Val Val
    210                 215                 220

Ser His Pro Gly Leu Leu Gln Asp Arg Arg Ile Thr His Thr Leu Gln
225                 230                 235                 240

Val Ala Phe Leu Ala Glu Ala Ser Val Arg Gly Leu Glu Asp Gln Asn
                245                 250                 255

Leu Trp Gln Val Gly Arg Glu Gly Ala Thr Leu Lys Cys Leu Ser Glu
            260                 265                 270

Gly Gln Pro Pro Pro Lys Tyr Asn Trp Thr Arg Leu Asp Gly Pro Leu
        275                 280                 285
```

```
Pro Ser Gly Val Arg Val Lys Gly Asp Thr Leu Gly Phe Pro Pro Leu
    290                 295                 300

Thr Thr Glu His Ser Gly Val Tyr Val Cys His Val Ser Asn Glu Leu
305                 310                 315                 320

Ser Ser Arg Asp Ser Gln Val Thr Val Glu Val Leu Asp Pro Glu Asp
                325                 330                 335

Pro Gly Lys Gln Val Asp Leu Val Ser Ala Ser Val Ile Ile Val Gly
            340                 345                 350

Val Ile Ala Ala Leu Leu Phe Cys Leu Leu Val Val Val Val Val Leu
        355                 360                 365

Met Ser Arg Tyr His Arg Arg Lys Ala Gln Gln Met Thr Gln Lys Tyr
    370                 375                 380

Glu Glu Glu Leu Thr Leu Thr Arg Glu Asn Ser Ile Arg Arg Leu His
385                 390                 395                 400

Ser His His Ser Asp Pro Arg Ser Gln Pro Glu Glu Ser Val Gly Leu
                405                 410                 415

Arg Ala Glu Gly His Pro Asp Ser Leu Lys Asp Asn Ser Ser Cys Ser
            420                 425                 430

Val Met Ser Glu Glu Pro Glu Gly Arg Ser Tyr Ser Thr Leu Thr Thr
        435                 440                 445

Val Arg Glu Ile Glu Thr Gln Thr Glu Leu Leu Ser Pro Gly Ser Gly
    450                 455                 460

Arg Thr Glu Glu Asp Asp Gln Asp Glu Gly Ile Lys Gln Ala Met
465                 470                 475                 480

Asn His Phe Val Gln Glu Asn Gly Thr Leu Arg Ala Lys Pro Thr Gly
                485                 490                 495

Asn Gly Ile Tyr Ile Asn Gly Arg Gly His Leu Val
            500                 505


<210> SEQ ID NO 65
<211> LENGTH: 517
<212> TYPE: PRT
<213> ORGANISM: Homo sapiens

<400> SEQUENCE: 65

Met Ala Arg Met Gly Leu Ala Gly Ala Ala Gly Arg Trp Trp Gly Leu
1               5                   10                  15

Ala Leu Gly Leu Thr Ala Phe Phe Leu Pro Gly Val His Ser Gln Val
            20                  25                  30

Val Gln Val Asn Asp Ser Met Tyr Gly Phe Ile Gly Thr Asp Val Val
        35                  40                  45

Leu His Cys Ser Phe Ala Asn Pro Leu Pro Ser Val Lys Ile Thr Gln
    50                  55                  60

Val Thr Trp Gln Lys Ser Thr Asn Gly Ser Lys Gln Asn Val Ala Ile
65                  70                  75                  80

Tyr Asn Pro Ser Met Gly Val Ser Val Leu Ala Pro Tyr Arg Glu Arg
                85                  90                  95

Val Glu Phe Leu Arg Pro Ser Phe Thr Asp Gly Thr Ile Arg Leu Ser
            100                 105                 110

Arg Leu Glu Leu Glu Asp Glu Gly Val Tyr Ile Cys Glu Phe Ala Thr
        115                 120                 125

Phe Pro Thr Gly Asn Arg Glu Ser Gln Leu Asn Leu Thr Val Met Ala
    130                 135                 140

Lys Pro Thr Asn Trp Ile Glu Gly Thr Gln Ala Val Leu Arg Ala Lys
```

-continued

```
145                 150                 155                 160

Lys Gly Gln Asp Asp Lys Val Leu Val Ala Thr Cys Thr Ser Ala Asn
                165                 170                 175

Gly Lys Pro Pro Ser Val Val Ser Trp Glu Thr Arg Leu Lys Gly Glu
            180                 185                 190

Ala Glu Tyr Gln Glu Ile Arg Asn Pro Asn Gly Thr Val Thr Val Ile
        195                 200                 205

Ser Arg Tyr Arg Leu Val Pro Ser Arg Glu Ala His Gln Gln Ser Leu
    210                 215                 220

Ala Cys Ile Val Asn Tyr His Met Asp Arg Phe Lys Glu Ser Leu Thr
225                 230                 235                 240

Leu Asn Val Gln Tyr Glu Pro Glu Val Thr Ile Glu Gly Phe Asp Gly
                245                 250                 255

Asn Trp Tyr Leu Gln Arg Met Asp Val Lys Leu Thr Cys Lys Ala Asp
            260                 265                 270

Ala Asn Pro Pro Ala Thr Glu Tyr His Trp Thr Thr Leu Asn Gly Ser
        275                 280                 285

Leu Pro Lys Gly Val Glu Ala Gln Asn Arg Thr Leu Phe Phe Lys Gly
    290                 295                 300

Pro Ile Asn Tyr Ser Leu Ala Gly Thr Tyr Ile Cys Glu Ala Thr Asn
305                 310                 315                 320

Pro Ile Gly Thr Arg Ser Gly Gln Val Glu Val Asn Ile Thr Glu Phe
                325                 330                 335

Pro Tyr Thr Pro Ser Pro Pro Glu His Gly Arg Arg Ala Gly Pro Val
            340                 345                 350

Pro Thr Ala Ile Ile Gly Gly Val Ala Gly Ser Ile Leu Leu Val Leu
        355                 360                 365

Ile Val Val Gly Gly Ile Val Val Ala Leu Arg Arg Arg Arg His Thr
    370                 375                 380

Phe Lys Gly Asp Tyr Ser Thr Lys Lys His Val Tyr Gly Asn Gly Tyr
385                 390                 395                 400

Ser Lys Ala Gly Ile Pro Gln His His Pro Pro Met Ala Gln Asn Leu
                405                 410                 415

Gln Tyr Pro Asp Asp Ser Asp Asp Glu Lys Lys Ala Gly Pro Leu Gly
            420                 425                 430

Gly Ser Ser Tyr Glu Glu Glu Glu Glu Glu Glu Glu Gly Gly Gly Gly
        435                 440                 445

Gly Glu Arg Lys Val Gly Gly Pro His Pro Lys Tyr Asp Glu Asp Ala
    450                 455                 460

Lys Arg Pro Tyr Phe Thr Val Asp Glu Ala Glu Ala Arg Gln Asp Gly
465                 470                 475                 480

Tyr Gly Asp Arg Thr Leu Gly Tyr Gln Tyr Asp Pro Glu Gln Leu Asp
                485                 490                 495

Leu Ala Glu Asn Met Val Ser Gln Asn Asp Gly Ser Phe Ile Ser Lys
            500                 505                 510

Lys Glu Trp Tyr Val
        515
```